United States Patent
Patel et al.

(10) Patent No.: US 10,986,465 B2
(45) Date of Patent: *Apr. 20, 2021

(54) AUTOMATED DETECTION AND CONFIGURATION OF WEARABLE DEVICES BASED ON ON-BODY STATUS, LOCATION, AND/OR ORIENTATION

(71) Applicant: Medidata Solutions, Inc., New York, NY (US)

(72) Inventors: Shyamal Patel, Somerville, MA (US); Ryan S. McGinnis, Cambridge, MA (US); Aadithya Prakash, Lexington, MA (US); Roozbeh Ghaffari, Cambridge, MA (US); Milan Raj, Cambridge, MA (US); Ikaro Silva, Brighton, MA (US); Elise Jortberg, Windham, NH (US)

(73) Assignee: MEDIDATA SOLUTIONS, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/660,496

(22) Filed: Oct. 22, 2019

(65) Prior Publication Data

US 2020/0296543 A1 Sep. 17, 2020

Related U.S. Application Data

(63) Continuation of application No. 15/048,576, filed on Feb. 19, 2016, now Pat. No. 10,477,354.

(Continued)

(51) Int. Cl.
*H04W 4/02* (2018.01)
*G16H 40/63* (2018.01)
(Continued)

(52) U.S. Cl.
CPC .............. *H04W 4/027* (2013.01); *A61B 5/01* (2013.01); *A61B 5/1114* (2013.01);
(Continued)

(58) Field of Classification Search
CPC ...... G06F 1/163; G08C 2201/32; G08C 17/02
See application file for complete search history.

(56) References Cited

U.S. PATENT DOCUMENTS

| 3,207,694 A | 9/1965 | Gogek |
| 3,716,861 A | 2/1973 | Root |
| (Continued) | | |

FOREIGN PATENT DOCUMENTS

| CN | 101084038 A | 12/2007 |
| CN | 202068986 U | 12/2011 |
| (Continued) | | |

OTHER PUBLICATIONS

U.S. Appl. No. 14/588,765, filed Jan. 2, 2015, S. Lee et al., Integrated Devices for Low Power Quantitative Measurements.

(Continued)

*Primary Examiner* — Changhyun Yi
(74) *Attorney, Agent, or Firm* — Nixon Peabody LLP

(57) ABSTRACT

An electronic device worn on a user includes one or more accelerometers. The one or more accelerometers generate acceleration information based on acceleration experienced by the electronic device. The electronic device further includes a processor and one or more associated memories, and the one or more associate memories include computer program code executable by the processor. The processor, configured by the computer program code, causes the electronic device to process the acceleration information to extract features from the acceleration information. The processor, configured by the computer program code, further (Continued)

causes the electronic device to process the features to determine the location of the electronic device on the user.

18 Claims, 17 Drawing Sheets

Related U.S. Application Data

(60) Provisional application No. 62/171,414, filed on Jun. 5, 2015, provisional application No. 62/118,843, filed on Feb. 20, 2015.

(51) Int. Cl.
*A61B 5/00* (2006.01)
*A61B 5/01* (2006.01)
*A61B 5/11* (2006.01)
*G01K 13/00* (2021.01)
*G01P 15/08* (2006.01)
*H04B 1/3827* (2015.01)
*H04W 64/00* (2009.01)
*G01K 13/20* (2021.01)

(52) U.S. Cl.
CPC .......... *A61B 5/6801* (2013.01); *G01K 13/20* (2021.01); *G01P 15/08* (2013.01); *G16H 40/63* (2018.01); *H04B 1/385* (2013.01); *H04W 64/006* (2013.01); *A61B 2562/0219* (2013.01)

(56) References Cited

U.S. PATENT DOCUMENTS

| | | |
|---|---|---|
| 3,805,427 A | 4/1974 | Epstein |
| 3,838,240 A | 9/1974 | Schelhorn |
| 3,892,905 A | 7/1975 | Albert |
| 4,136,162 A | 1/1979 | Fuchs |
| 4,278,474 A | 7/1981 | Blakeslee |
| 4,304,235 A | 12/1981 | Kaufman |
| 4,416,288 A | 11/1983 | Freeman |
| 4,658,153 A | 4/1987 | Brosh |
| 4,766,670 A | 8/1988 | Gazdik |
| 4,911,169 A | 3/1990 | Ferrari |
| 4,968,137 A | 11/1990 | Yount |
| 5,059,424 A | 10/1991 | Cartmell |
| 5,064,576 A | 11/1991 | Suto |
| 5,272,375 A | 12/1993 | Belopolsky |
| 5,278,627 A | 1/1994 | Aoyagi |
| 5,306,917 A | 4/1994 | Black |
| 5,326,521 A | 7/1994 | East |
| 5,331,966 A | 7/1994 | Bennett |
| 5,360,987 A | 11/1994 | Shibib |
| 5,413,592 A | 5/1995 | Schroeppel |
| 5,471,982 A | 5/1995 | Edwards |
| 5,454,270 A | 10/1995 | Brown |
| 5,491,651 A | 2/1996 | Janic |
| 5,567,975 A | 10/1996 | Walsh |
| 5,580,794 A | 12/1996 | Allen |
| 5,617,870 A | 4/1997 | Hastings |
| 5,676,144 A | 10/1997 | Schoendorfer |
| 5,811,790 A | 9/1998 | Endo |
| 5,817,008 A | 10/1998 | Rafert |
| 5,907,477 A | 5/1999 | Tuttle |
| 6,063,046 A | 5/2000 | Allum |
| 6,220,916 B1 | 4/2001 | Bart |
| 6,265,090 B1 | 7/2001 | Nishide |
| 6,270,872 B1 | 8/2001 | Cline |
| 6,282,960 B1 | 9/2001 | Samuels |
| 6,343,514 B1 | 2/2002 | Smith |
| 6,387,052 B1 | 5/2002 | Quinn |
| 6,403,397 B1 | 6/2002 | Katz |
| 6,410,971 B1 | 6/2002 | Otey |
| 6,421,016 B1 | 7/2002 | Phillips |
| 6,450,026 B1 | 9/2002 | Desarnaud |
| 6,455,931 B1 | 9/2002 | Hamilton |
| 6,479,395 B1 | 11/2002 | Smith |
| 6,567,158 B1 | 5/2003 | Falcial |
| 6,626,940 B2 | 9/2003 | Crowley |
| 6,628,987 B1 | 9/2003 | Hill |
| 6,641,860 B1 | 11/2003 | Kaiserman |
| 6,775,906 B1 | 8/2004 | Silverbrook |
| 6,784,844 B1 | 8/2004 | Boakes |
| 6,825,539 B2 | 11/2004 | Tai |
| 6,937,900 B1 | 8/2005 | Pianca |
| 6,965,160 B2 | 11/2005 | Cobbley |
| 6,987,314 B1 | 1/2006 | Yoshida |
| 7,259,030 B2 | 8/2007 | Daniels |
| 7,265,298 B2 | 9/2007 | Maghribi |
| 7,302,751 B2 | 12/2007 | Hamburgen |
| 7,337,012 B2 | 2/2008 | Maghribi |
| 7,487,587 B2 | 2/2009 | Vanfleteren |
| 7,491,892 B2 | 2/2009 | Wagner |
| 7,521,292 B2 | 4/2009 | Rogers |
| 7,557,367 B2 | 7/2009 | Rogers |
| 7,618,260 B2 | 11/2009 | Daniel |
| 7,622,367 B1 | 11/2009 | Nuzzo |
| 7,727,228 B2 | 6/2010 | Abboud |
| 7,739,791 B2 | 6/2010 | Brandenburg |
| 7,759,167 B2 | 7/2010 | Vanfleteren |
| 7,815,095 B2 | 10/2010 | Fujisawa |
| 7,960,246 B2 | 6/2011 | Flamand |
| 7,982,296 B2 | 7/2011 | Nuzzo |
| 8,097,926 B2 | 1/2012 | De Graff |
| 8,198,621 B2 | 6/2012 | Rogers |
| 8,207,473 B2 | 6/2012 | Axisa |
| 8,217,381 B2 | 7/2012 | Rogers |
| 8,332,053 B1 | 12/2012 | Patterson |
| 8,372,726 B2 | 2/2013 | De Graff |
| 8,389,862 B2 | 3/2013 | Arora |
| 8,431,828 B2 | 4/2013 | Vanfleteren |
| 8,440,546 B2 | 5/2013 | Nuzzo |
| 8,536,667 B2 | 9/2013 | De Graff |
| 8,552,299 B2 | 10/2013 | Rogers |
| 8,609,471 B2 | 12/2013 | Xu |
| 8,618,656 B2 | 12/2013 | Oh |
| 8,664,699 B2 | 3/2014 | Nuzzo |
| 8,679,888 B2 | 3/2014 | Rogers |
| 8,729,524 B2 | 5/2014 | Rogers |
| 8,754,396 B2 | 6/2014 | Rogers |
| 8,865,489 B2 | 10/2014 | Rogers |
| 8,886,334 B2 | 11/2014 | Ghaffari |
| 8,905,772 B2 | 12/2014 | Rogers |
| 9,012,784 B2 | 4/2015 | Arora |
| 9,082,025 B2 | 7/2015 | Fastert |
| 9,105,555 B2 | 8/2015 | Rogers |
| 9,105,782 B2 | 8/2015 | Rogers |
| 9,107,592 B2 | 8/2015 | Litt |
| 9,119,533 B2 | 9/2015 | Ghaffari |
| 9,123,614 B2 | 9/2015 | Graff |
| 9,133,024 B2 | 9/2015 | Phan |
| 9,159,635 B2 | 10/2015 | Elolampi |
| 9,168,094 B2 | 10/2015 | Lee |
| 9,171,794 B2 | 10/2015 | Rafferty |
| 9,186,060 B2 | 11/2015 | De Graff |
| 9,226,402 B2 | 12/2015 | Hsu |
| 9,247,637 B2 | 1/2016 | Hsu |
| 9,289,132 B2 | 3/2016 | Ghaffari |
| 9,295,842 B2 | 3/2016 | Ghaffari |
| 9,320,907 B2 | 4/2016 | Bogie |
| 9,324,733 B2 | 4/2016 | Rogers |
| 9,372,123 B2 | 6/2016 | Li |
| 9,408,305 B2 | 8/2016 | Hsu |
| 9,420,953 B2 | 8/2016 | Litt |
| 9,450,043 B2 | 9/2016 | Nuzzo |
| 9,515,025 B2 | 12/2016 | Rogers |
| 9,516,758 B2 | 12/2016 | Arora |
| 9,545,216 B2 | 1/2017 | D'Angelo |
| 9,545,285 B2 | 1/2017 | Ghaffari |
| 9,554,850 B2 | 1/2017 | Lee |
| 9,579,040 B2 | 2/2017 | Rafferty |
| 9,583,428 B2 | 2/2017 | Rafferty |
| D781,270 S | 3/2017 | Li |

(56) References Cited

U.S. PATENT DOCUMENTS

| | | |
|---|---|---|
| 9,622,680 B2 | 4/2017 | Ghaffari |
| 9,629,586 B2 | 4/2017 | Ghaffari |
| 9,647,171 B2 | 5/2017 | Rogers |
| 9,655,560 B2 | 5/2017 | Ghaffari |
| 9,662,069 B2 | 5/2017 | De Graff |
| 9,702,839 B2 | 7/2017 | Ghaffari |
| 9,704,908 B2 | 7/2017 | Graff |
| 9,706,647 B2 | 7/2017 | Hsu |
| 9,723,122 B2 | 8/2017 | Ghaffari |
| 9,723,711 B2 | 8/2017 | Elolampi |
| 9,750,421 B2 | 9/2017 | Ghaffari |
| 9,757,050 B2 | 9/2017 | Ghaffari |
| 9,761,444 B2 | 9/2017 | Nuzzo |
| 9,768,086 B2 | 9/2017 | Nuzzo |
| 9,801,557 B2 | 10/2017 | Ghaffari |
| 9,844,145 B2 | 10/2017 | Hsu |
| 9,810,623 B2 | 11/2017 | Ghaffari |
| 9,833,190 B2 | 12/2017 | Ghaffari |
| 9,839,367 B2 | 12/2017 | Litt |
| 9,846,829 B2 | 12/2017 | Fastert |
| 9,894,757 B2 | 2/2018 | Arora |
| 9,899,330 B2 | 2/2018 | Dalal |
| 9,949,691 B2 | 4/2018 | Huppert |
| 10,032,709 B2 | 7/2018 | Rafferty |
| D825,537 S | 8/2018 | Li |
| 10,064,269 B2 | 8/2018 | Rogers |
| 10,186,546 B2 | 1/2019 | De Graff |
| 10,258,282 B2 | 4/2019 | Huppert |
| 10,277,386 B2 | 4/2019 | Raj |
| 10,296,819 B2 | 5/2019 | Fastert |
| 10,297,572 B2 | 5/2019 | Dalal |
| 10,300,371 B2 | 5/2019 | Ghaffari |
| 10,325,951 B2 | 6/2019 | Graff |
| 10,332,563 B2 | 6/2019 | Lee |
| 10,334,724 B2 | 6/2019 | Hsu |
| 10,374,072 B2 | 8/2019 | Nuzzo |
| 10,383,219 B2 | 8/2019 | Arora |
| 10,398,343 B2 | 9/2019 | Murphy |
| 10,410,962 B2 | 9/2019 | McMahon |
| 10,447,347 B2 | 10/2019 | Raj |
| 10,467,926 B2 | 11/2019 | Ghaffari |
| 10,477,354 B2 * | 11/2019 | Patel ................ H04W 64/006 |
| 10,482,743 B2 | 11/2019 | Li |
| 10,485,118 B2 | 11/2019 | Elolampi |
| 10,532,211 B2 | 1/2020 | Ghaffari |
| 10,567,152 B2 | 2/2020 | Raj |
| 10,653,332 B2 | 5/2020 | McGrane |
| 2001/0012918 A1 | 8/2001 | Swanson |
| 2001/0021867 A1 | 9/2001 | Kordis |
| 2001/0043513 A1 | 11/2001 | Grupp |
| 2002/0000813 A1 | 1/2002 | Hirono |
| 2002/0026127 A1 | 2/2002 | Balbierz |
| 2002/0060633 A1 | 5/2002 | Crisco, III |
| 2002/0077534 A1 | 6/2002 | Durousseau |
| 2002/0079572 A1 | 6/2002 | Khan |
| 2002/0082515 A1 | 6/2002 | Campbell |
| 2002/0094701 A1 | 7/2002 | Biegelsen |
| 2002/0107436 A1 | 8/2002 | Barton |
| 2002/0113739 A1 | 8/2002 | Howard |
| 2002/0128700 A1 | 9/2002 | Cross, Jr. |
| 2002/0145467 A1 | 10/2002 | Minch |
| 2002/0151934 A1 | 10/2002 | Levine |
| 2002/0158330 A1 | 10/2002 | Moon |
| 2002/0173730 A1 | 11/2002 | Pottgen |
| 2002/0193724 A1 | 12/2002 | Stebbings |
| 2003/0017848 A1 | 1/2003 | Engstrom |
| 2003/0045025 A1 | 3/2003 | Coyle |
| 2003/0097165 A1 | 5/2003 | Krulevitch |
| 2003/0120271 A1 | 6/2003 | Burnside |
| 2003/0162507 A1 | 8/2003 | Vatt |
| 2003/0214408 A1 | 11/2003 | Grajales |
| 2003/0227116 A1 | 12/2003 | Halik |
| 2003/0236455 A1 | 12/2003 | Swanson |
| 2004/0006264 A1 | 1/2004 | Mojarradi |
| 2004/0085469 A1 | 5/2004 | Johnson |
| 2004/0092806 A1 | 5/2004 | Sagon |
| 2004/0106334 A1 | 6/2004 | Suzuki |
| 2004/0118831 A1 | 6/2004 | Martin |
| 2004/0135094 A1 | 7/2004 | Niigaki |
| 2004/0138558 A1 | 7/2004 | Dunki-Jacobs |
| 2004/0149921 A1 | 8/2004 | Smyk |
| 2004/0178466 A1 | 9/2004 | Merrill |
| 2004/0192082 A1 | 9/2004 | Wagner |
| 2004/0201134 A1 | 10/2004 | Kawai |
| 2004/0203486 A1 | 10/2004 | Shepherd |
| 2004/0221370 A1 | 11/2004 | Hannula |
| 2004/0238819 A1 | 12/2004 | Maghribi |
| 2004/0243204 A1 | 12/2004 | Maghribi |
| 2005/0021103 A1 | 1/2005 | DiLorenzo |
| 2005/0029680 A1 | 2/2005 | Jung |
| 2005/0030408 A1 | 2/2005 | Ito |
| 2005/0065486 A1 | 3/2005 | Fattman |
| 2005/0067293 A1 | 3/2005 | Naito |
| 2005/0070778 A1 | 3/2005 | Lackey |
| 2005/0096513 A1 | 5/2005 | Ozguz |
| 2005/0113744 A1 | 5/2005 | Donoghue |
| 2005/0139683 A1 | 6/2005 | Yi |
| 2005/0171524 A1 | 8/2005 | Stern |
| 2005/0203366 A1 | 9/2005 | Donoghue |
| 2005/0204811 A1 | 9/2005 | Neff |
| 2005/0248312 A1 | 11/2005 | Cao |
| 2005/0261617 A1 | 11/2005 | Hall |
| 2005/0258050 A1 | 12/2005 | Bruce |
| 2005/0285262 A1 | 12/2005 | Knapp |
| 2006/0003709 A1 | 1/2006 | Wood |
| 2006/0009700 A1 | 1/2006 | Brumfield |
| 2006/0038182 A1 | 2/2006 | Rogers |
| 2006/0071349 A1 | 4/2006 | Tokushige |
| 2006/0084394 A1 | 4/2006 | Engstrom |
| 2006/0106321 A1 | 5/2006 | Lewinsky |
| 2006/0122298 A1 | 6/2006 | Menon |
| 2006/0128346 A1 | 6/2006 | Yasui |
| 2006/0154398 A1 | 7/2006 | Qing |
| 2006/0160560 A1 | 7/2006 | Josenhans |
| 2006/0235314 A1 | 10/2006 | Migliuolo |
| 2006/0248946 A1 | 11/2006 | Howell |
| 2006/0257945 A1 | 11/2006 | Masters |
| 2006/0264767 A1 | 11/2006 | Shennib |
| 2006/0270135 A1 | 11/2006 | Chrysler |
| 2006/0276702 A1 | 12/2006 | McGinnis |
| 2006/0286785 A1 | 12/2006 | Rogers |
| 2007/0027374 A1 | 2/2007 | Wihlborg |
| 2007/0027514 A1 | 2/2007 | Gerber |
| 2007/0031283 A1 | 2/2007 | Davis |
| 2007/0069894 A1 | 3/2007 | Lee |
| 2007/0083079 A1 | 4/2007 | Lee |
| 2007/0108389 A1 | 5/2007 | Makela |
| 2007/0113399 A1 | 5/2007 | Kumar |
| 2007/0123756 A1 | 5/2007 | Kitajima |
| 2007/0139451 A1 | 6/2007 | Somasiri |
| 2007/0151358 A1 | 7/2007 | Chien |
| 2007/0179373 A1 | 8/2007 | Pronovost |
| 2007/0190880 A1 | 8/2007 | Dubrow |
| 2007/0196957 A1 | 8/2007 | Akutagawa |
| 2007/0215890 A1 | 9/2007 | Harbers |
| 2007/0270672 A1 | 11/2007 | Hayter |
| 2007/0270674 A1 | 11/2007 | Kane |
| 2008/0036097 A1 | 2/2008 | Ito |
| 2008/0046080 A1 | 2/2008 | Vanden Bulcke |
| 2008/0074383 A1 | 3/2008 | Dean |
| 2008/0091089 A1 | 4/2008 | Guillory |
| 2008/0096620 A1 | 4/2008 | Lee |
| 2008/0139894 A1 | 6/2008 | Szydlo-Moore |
| 2008/0157235 A1 | 7/2008 | Rogers |
| 2008/0185534 A1 | 8/2008 | Simon |
| 2008/0188912 A1 | 8/2008 | Stone |
| 2008/0190202 A1 | 8/2008 | Kulach |
| 2008/0193749 A1 | 8/2008 | Thompson |
| 2008/0200973 A1 | 8/2008 | Mallozzi |
| 2008/0204021 A1 | 8/2008 | Leussler |
| 2008/0211087 A1 | 9/2008 | Mueller-Hipper |
| 2008/0237840 A1 | 10/2008 | Alcoe |
| 2008/0259576 A1 | 10/2008 | Johnson |
| 2008/0262381 A1 | 10/2008 | Kolen |

(56) References Cited

U.S. PATENT DOCUMENTS

| | | |
|---|---|---|
| 2008/0275327 A1 | 11/2008 | Faarbaek |
| 2008/0287167 A1 | 11/2008 | Caine |
| 2008/0297350 A1 | 12/2008 | Iwasa |
| 2008/0300559 A1 | 12/2008 | Gustafson |
| 2008/0309807 A1 | 12/2008 | Kinoshita |
| 2008/0313552 A1 | 12/2008 | Buehler |
| 2009/0000377 A1 | 1/2009 | Shipps |
| 2009/0001550 A1 | 1/2009 | Li |
| 2009/0015560 A1 | 1/2009 | Robinson |
| 2009/0017884 A1 | 1/2009 | Rotschild |
| 2009/0048556 A1 | 2/2009 | Durand |
| 2009/0076363 A1 | 3/2009 | Bly |
| 2009/0088750 A1 | 4/2009 | Hushka |
| 2009/0107704 A1 | 4/2009 | Vanfleteren |
| 2009/0154736 A1 | 6/2009 | Lee |
| 2009/0184254 A1 | 7/2009 | Miura |
| 2009/0204168 A1 | 8/2009 | Kallmeyer |
| 2009/0215385 A1 | 8/2009 | Waters |
| 2009/0225751 A1 | 9/2009 | Koenck |
| 2009/0261828 A1 | 10/2009 | Nordmeyer-Massner |
| 2009/0270170 A1 | 10/2009 | Patton |
| 2009/0273909 A1 | 11/2009 | Shin |
| 2009/0283891 A1 | 11/2009 | Dekker |
| 2009/0291508 A1 | 11/2009 | Babu |
| 2009/0294803 A1 | 12/2009 | Nuzzo |
| 2009/0317639 A1 | 12/2009 | Axisa |
| 2009/0322480 A1 | 12/2009 | Benedict |
| 2010/0002402 A1 | 1/2010 | Rogers |
| 2010/0030167 A1 | 2/2010 | Thirstrup |
| 2010/0036211 A1 | 2/2010 | La Rue |
| 2010/0041966 A1 | 2/2010 | Kang |
| 2010/0059863 A1 | 3/2010 | Rogers |
| 2010/0072577 A1 | 3/2010 | Nuzzo |
| 2010/0073669 A1 | 3/2010 | Colvin |
| 2010/0087782 A1 | 4/2010 | Ghaffari |
| 2010/0090781 A1 | 4/2010 | Yamamoto |
| 2010/0090824 A1 | 4/2010 | Rowell |
| 2010/0116526 A1 | 5/2010 | Arora |
| 2010/0117660 A1 | 5/2010 | Douglas |
| 2010/0234716 A1 | 9/2010 | Engel |
| 2010/0245011 A1 | 9/2010 | Chatzopoulos |
| 2010/0254092 A1 | 10/2010 | Dong |
| 2010/0271191 A1 | 10/2010 | De Graff |
| 2010/0298895 A1 | 11/2010 | Ghaffari |
| 2010/0317132 A1 | 12/2010 | Rogers |
| 2010/0321161 A1 | 12/2010 | Isabell |
| 2010/0327387 A1 | 12/2010 | Kasai |
| 2011/0011179 A1 | 1/2011 | Gustafsson |
| 2011/0019370 A1 | 1/2011 | Koh |
| 2011/0019371 A1 | 1/2011 | Koh |
| 2011/0034760 A1 | 2/2011 | Brynelsen |
| 2011/0034912 A1 | 2/2011 | De Graff |
| 2011/0051384 A1 | 3/2011 | Kriechbaum |
| 2011/0054583 A1 | 3/2011 | Litt |
| 2011/0066044 A1 | 3/2011 | Moon |
| 2011/0071603 A1 | 3/2011 | Moore |
| 2011/0098583 A1 | 4/2011 | Pandia |
| 2011/0101789 A1 | 5/2011 | Salter |
| 2011/0121822 A1 | 5/2011 | Parsche |
| 2011/0136436 A1 | 6/2011 | Hoyt |
| 2011/0140856 A1 | 6/2011 | Downie |
| 2011/0140897 A1 | 6/2011 | Purks |
| 2011/0148349 A1 | 6/2011 | Kim |
| 2011/0175735 A1 | 7/2011 | Forster |
| 2011/0184320 A1 | 7/2011 | Shipps |
| 2011/0185611 A1 | 8/2011 | Adams |
| 2011/0193105 A1 | 8/2011 | Lerman |
| 2011/0213559 A1 | 9/2011 | Pollack |
| 2011/0215931 A1 | 9/2011 | Callsen |
| 2011/0218756 A1 | 9/2011 | Callsen |
| 2011/0218757 A1 | 9/2011 | Callsen |
| 2011/0220890 A1 | 9/2011 | Nuzzo |
| 2011/0221580 A1 | 9/2011 | Marsanne |
| 2011/0222375 A1 | 9/2011 | Tsubata |
| 2011/0263950 A1 | 10/2011 | Larson |
| 2011/0270049 A1 | 11/2011 | Katra |
| 2011/0277813 A1 | 11/2011 | Rogers |
| 2011/0284268 A1 | 11/2011 | Palaniswamy |
| 2011/0306851 A1 | 12/2011 | Wang |
| 2011/0317737 A1 | 12/2011 | Klewer |
| 2012/0016258 A1 | 1/2012 | Webster |
| 2012/0028575 A1 | 2/2012 | Chen |
| 2012/0051005 A1 | 3/2012 | Vanfleteren |
| 2012/0052268 A1 | 3/2012 | Axisa |
| 2012/0059235 A1 | 3/2012 | Davies |
| 2012/0065937 A1 | 3/2012 | De Graff |
| 2012/0068848 A1 | 3/2012 | Campbell |
| 2012/0074546 A1 | 3/2012 | Chong |
| 2012/0077441 A1 | 3/2012 | Howard |
| 2012/0087216 A1 | 4/2012 | Keung |
| 2012/0091594 A1 | 4/2012 | Landesberger |
| 2012/0092178 A1 | 4/2012 | Callsen |
| 2012/0092222 A1 | 4/2012 | Kato |
| 2012/0101413 A1 | 4/2012 | Beetel |
| 2012/0101538 A1 | 4/2012 | Ballakur |
| 2012/0108012 A1 | 5/2012 | Yasuda |
| 2012/0116382 A1 | 5/2012 | Ku |
| 2012/0126418 A1 | 5/2012 | Feng |
| 2012/0150072 A1 | 6/2012 | Revol-Cavalier |
| 2012/0150074 A1 | 6/2012 | Yanev |
| 2012/0150453 A1 | 6/2012 | Benzel |
| 2012/0157804 A1 | 6/2012 | Rogers |
| 2012/0165759 A1 | 6/2012 | Rogers |
| 2012/0172697 A1 | 7/2012 | Urman |
| 2012/0178367 A1 | 7/2012 | Matsumoto |
| 2012/0179075 A1 | 7/2012 | Perry |
| 2012/0206097 A1 | 8/2012 | Scar |
| 2012/0215127 A1 | 8/2012 | Shikida |
| 2012/0220835 A1 | 8/2012 | Chung |
| 2012/0245444 A1 | 9/2012 | Otis |
| 2012/0256308 A1 | 10/2012 | Helin |
| 2012/0256492 A1 | 10/2012 | Song |
| 2012/0314382 A1 | 12/2012 | Wesselmann |
| 2012/0316455 A1 | 12/2012 | Rahman |
| 2012/0327608 A1 | 12/2012 | Rogers |
| 2013/0035751 A1 | 2/2013 | Shalev |
| 2013/0041235 A1 | 2/2013 | Rogers |
| 2013/0044215 A1 | 2/2013 | Rothkopf |
| 2013/0066365 A1 | 3/2013 | Belson |
| 2013/0079693 A1 | 3/2013 | Ranky |
| 2013/0085552 A1 | 4/2013 | Mandel |
| 2013/0099358 A1 | 4/2013 | Elolampi |
| 2013/0100618 A1 | 4/2013 | Rogers |
| 2013/0116520 A1 | 5/2013 | Roham |
| 2013/0118255 A1 | 5/2013 | Callsen |
| 2013/0123587 A1 | 5/2013 | Sarrafzadeh |
| 2013/0131660 A1 | 5/2013 | Monson |
| 2013/0147063 A1 | 6/2013 | Park |
| 2013/0185003 A1 | 7/2013 | Carbeck |
| 2013/0192356 A1 | 8/2013 | De Graff |
| 2013/0197319 A1 | 8/2013 | Monty |
| 2013/0200268 A1 | 8/2013 | Rafferty |
| 2013/0211761 A1 | 8/2013 | Brandsma |
| 2013/0214300 A1 | 8/2013 | Lerman |
| 2013/0215467 A1 | 8/2013 | Fein |
| 2013/0237150 A1 | 9/2013 | Royston |
| 2013/0245387 A1 | 9/2013 | Patel |
| 2013/0245388 A1 | 9/2013 | Rafferty |
| 2013/0253285 A1 | 9/2013 | Bly |
| 2013/0261415 A1 | 10/2013 | Ashe |
| 2013/0261464 A1 | 10/2013 | Singh |
| 2013/0285836 A1 | 10/2013 | Proud |
| 2013/0313713 A1 | 11/2013 | Arora |
| 2013/0316442 A1 | 11/2013 | Meurville |
| 2013/0316487 A1 | 11/2013 | De Graff |
| 2013/0316645 A1 | 11/2013 | Li |
| 2013/0320503 A1 | 12/2013 | Nuzzo |
| 2013/0321373 A1 | 12/2013 | Yoshizumi |
| 2013/0325357 A1 | 12/2013 | Walerow |
| 2013/0328219 A1 | 12/2013 | Chau |
| 2013/0331914 A1 | 12/2013 | Lee |
| 2013/0335011 A1 | 12/2013 | Bohringer |
| 2014/0001058 A1 | 1/2014 | Ghaffari |
| 2014/0002242 A1 | 1/2014 | Fenkanyn |

(56) References Cited

U.S. PATENT DOCUMENTS

| | | |
|---|---|---|
| 2014/0012160 A1 | 1/2014 | Ghaffari |
| 2014/0012242 A1 | 1/2014 | Lee |
| 2014/0022746 A1 | 1/2014 | Hsu |
| 2014/0039290 A1 | 2/2014 | De Graff |
| 2014/0081100 A1 | 3/2014 | Muhsin |
| 2014/0097944 A1 | 4/2014 | Fastert |
| 2014/0108842 A1 | 4/2014 | Frank |
| 2014/0110859 A1 | 4/2014 | Rafferty |
| 2014/0125458 A1 | 5/2014 | Bachman |
| 2014/0140020 A1 | 5/2014 | Rogers |
| 2014/0188426 A1 | 7/2014 | Fastert |
| 2014/0191236 A1 | 7/2014 | Nuzzo |
| 2014/0206976 A1 | 7/2014 | Thompson |
| 2014/0216524 A1 | 8/2014 | Rogers |
| 2014/0257427 A1 | 9/2014 | Marnfeldt |
| 2014/0275835 A1 | 9/2014 | Lamego |
| 2014/0303452 A1 | 10/2014 | Ghaffari |
| 2014/0303520 A1 | 10/2014 | Telfort |
| 2014/0303680 A1 | 10/2014 | Donnelly |
| 2014/0308930 A1 | 10/2014 | Tran |
| 2014/0316191 A1 | 10/2014 | De Zambotti |
| 2014/0316192 A1 | 10/2014 | de Zamboti |
| 2014/0318699 A1* | 10/2014 | Longinotti-Buitoni ........ A61B 5/6805 156/247 |
| 2014/0340857 A1 | 11/2014 | Hsu |
| 2014/0342174 A1 | 11/2014 | Tominaga |
| 2014/0350883 A1 | 11/2014 | Carter |
| 2014/0371547 A1 | 12/2014 | Gartenberg |
| 2014/0371823 A1 | 12/2014 | Mashiach |
| 2014/0374872 A1 | 12/2014 | Rogers |
| 2014/0375465 A1 | 12/2014 | Fenuccio |
| 2015/0001462 A1 | 1/2015 | Rogers |
| 2015/0019135 A1 | 1/2015 | Kacyvenski |
| 2015/0025394 A1 | 1/2015 | Hong |
| 2015/0035743 A1 | 2/2015 | Rosener |
| 2015/0100135 A1 | 4/2015 | Ives |
| 2015/0116814 A1 | 4/2015 | Takakura |
| 2015/0126878 A1 | 5/2015 | An |
| 2015/0145676 A1 | 5/2015 | Adhikari |
| 2015/0150505 A1 | 6/2015 | Kaskoun |
| 2015/0164377 A1 | 6/2015 | Nathan |
| 2015/0178806 A1 | 6/2015 | Nuzzo |
| 2015/0181700 A1 | 6/2015 | Rogers |
| 2015/0194817 A1 | 7/2015 | Lee |
| 2015/0237711 A1 | 8/2015 | Rogers |
| 2015/0241288 A1 | 8/2015 | Keen |
| 2015/0248833 A1 | 9/2015 | Arne |
| 2015/0272652 A1 | 10/2015 | Ghaffari |
| 2015/0335254 A1 | 11/2015 | Fastert |
| 2015/0359469 A1 | 12/2015 | Jacobs |
| 2015/0371511 A1 | 12/2015 | Miller |
| 2015/0373487 A1 | 12/2015 | Miller |
| 2016/0006123 A1 | 1/2016 | Li |
| 2016/0015962 A1 | 1/2016 | Shokoueinejad Maragheh |
| 2016/0037478 A1 | 2/2016 | Skaaksrud |
| 2016/0049824 A1 | 2/2016 | Stein |
| 2016/0058380 A1 | 3/2016 | Lee |
| 2016/0066854 A1 | 3/2016 | Mei |
| 2016/0081563 A1 | 3/2016 | Wiard |
| 2016/0086909 A1 | 3/2016 | Garlock |
| 2016/0095652 A1 | 4/2016 | Lee |
| 2016/0099214 A1 | 4/2016 | Dalal |
| 2016/0099227 A1 | 4/2016 | Dalal |
| 2016/0111353 A1 | 4/2016 | Rafferty |
| 2016/0135740 A1 | 5/2016 | Ghaffari |
| 2016/0178251 A1 | 6/2016 | Johnson |
| 2016/0213262 A1 | 7/2016 | Ghaffari |
| 2016/0213424 A1 | 7/2016 | Ghaffari |
| 2016/0228640 A1 | 8/2016 | Pindado |
| 2016/0240061 A1 | 8/2016 | Li |
| 2016/0249174 A1 | 8/2016 | Patel |
| 2016/0256070 A1 | 9/2016 | Murphy |
| 2016/0271290 A1 | 9/2016 | Humayun |
| 2016/0284544 A1 | 9/2016 | Nuzzo |
| 2016/0287177 A1 | 10/2016 | Huppert |
| 2016/0293794 A1 | 10/2016 | Nuzzo |
| 2016/0309594 A1 | 10/2016 | Hsu |
| 2016/0322283 A1 | 11/2016 | McMahon |
| 2016/0338646 A1 | 11/2016 | Lee |
| 2016/0361015 A1 | 12/2016 | Wang |
| 2016/0371957 A1 | 12/2016 | Ghaffari |
| 2016/0381789 A1 | 12/2016 | Rogers |
| 2017/0049397 A1 | 2/2017 | Sun |
| 2017/0071491 A1 | 3/2017 | Litt |
| 2017/0079588 A1 | 3/2017 | Ghaffari |
| 2017/0079589 A1 | 3/2017 | Ghaffari |
| 2017/0083312 A1 | 3/2017 | Pindado |
| 2017/0086747 A1 | 3/2017 | Ghaffari |
| 2017/0086748 A1 | 3/2017 | Ghaffari |
| 2017/0086749 A1 | 3/2017 | Ghaffari |
| 2017/0105795 A1 | 4/2017 | Lee |
| 2017/0110417 A1 | 4/2017 | Arora |
| 2017/0164865 A1 | 6/2017 | Rafferty |
| 2017/0164866 A1 | 6/2017 | Rafferty |
| 2017/0181659 A1 | 6/2017 | Rafferty |
| 2017/0186727 A1 | 6/2017 | Dalal |
| 2017/0188942 A1 | 7/2017 | Ghaffari |
| 2017/0200670 A1 | 7/2017 | Rafferty |
| 2017/0200679 A1 | 7/2017 | Rogers |
| 2017/0200707 A1 | 7/2017 | Rogers |
| 2017/0244285 A1 | 8/2017 | Raj |
| 2017/0296114 A1 | 10/2017 | Ghaffari |
| 2017/0331524 A1 | 11/2017 | Aranyosi |
| 2017/0340236 A1 | 11/2017 | Ghaffari |
| 2018/0076336 A1 | 3/2018 | Graff |
| 2018/0098732 A1* | 4/2018 | Williamson ......... A61B 5/4833 |
| 2018/0111353 A1 | 4/2018 | Huppert |
| 2018/0192918 A1 | 7/2018 | Ives |
| 2018/0199884 A1 | 7/2018 | Huppert |
| 2018/0293472 A1 | 10/2018 | Fastert |
| 2018/0302980 A1 | 10/2018 | Arora |
| 2018/0302988 A1 | 10/2018 | Hsu |
| 2018/0308799 A1 | 10/2018 | Dalal |
| 2019/0154723 A1 | 5/2019 | Kacyvenski |
| 2019/0265168 A1 | 8/2019 | Huppert |
| 2019/0314192 A1 | 10/2019 | Raj |
| 2019/0365263 A1 | 12/2019 | Raj |
| 2020/0060618 A1 | 2/2020 | Davis |

FOREIGN PATENT DOCUMENTS

| | | |
|---|---|---|
| CN | 102772246 A | 11/2012 |
| CN | 103165478 A | 6/2013 |
| CN | 103313671 A | 9/2013 |
| CN | 103619590 A | 3/2014 |
| DE | 10 2006 011 596 A1 | 9/2007 |
| DE | 10 2006 051 745 A1 | 5/2008 |
| DE | 10 2007 046 886 A1 | 4/2009 |
| DE | 10 2008 044 902 A1 | 3/2010 |
| EP | 0526855 A1 | 2/1993 |
| EP | 0585670 A2 | 3/1994 |
| EP | 0779059 A1 | 6/1997 |
| EP | 0952542 A1 | 10/1999 |
| EP | 1100296 A1 | 5/2001 |
| EP | 1188157 A1 | 3/2002 |
| EP | 1671581 A1 | 6/2006 |
| EP | 1808124 A2 | 7/2007 |
| EP | 2259062 A2 | 12/2010 |
| EP | 2498196 A2 | 9/2012 |
| EP | 2541995 A1 | 1/2013 |
| JP | H 04-290489 A | 10/1992 |
| JP | 05-087511 A | 4/1993 |
| JP | H 05-102228 A | 4/1993 |
| JP | 9-201338 A | 8/1997 |
| JP | H10-155753 A | 6/1998 |
| JP | 2001-156278 A | 6/2001 |
| JP | 03-218797 B2 | 10/2001 |
| JP | 2002-90479 A | 3/2002 |
| JP | 2002-263185 A | 9/2002 |
| JP | 2003-046291 A | 2/2003 |
| JP | 2005-052212 A | 3/2005 |
| JP | 2006-520657 A | 9/2006 |
| JP | 2006-523127 A | 10/2006 |

(56) References Cited

FOREIGN PATENT DOCUMENTS

| | | |
|---|---|---|
| JP | 2007-042829 A | 2/2007 |
| JP | 2007-502136 A | 2/2007 |
| JP | 2008-194323 A | 8/2008 |
| JP | 2009-150590 A | 7/2009 |
| JP | 2009-158839 A | 7/2009 |
| JP | 2009-170173 A | 7/2009 |
| JP | 2011-082050 A | 4/2011 |
| JP | 2011-103914 A | 6/2011 |
| JP | 2011-122732 A | 6/2011 |
| JP | 2012-134272 A | 7/2012 |
| JP | 2012-515436 A | 7/2012 |
| JP | 2013-089959 A | 5/2013 |
| JP | 2013-128060 A | 6/2013 |
| JP | 2013-130384 A | 7/2013 |
| JP | 2013-536592 A | 9/2013 |
| WO | WO 1999/038211 A2 | 7/1999 |
| WO | WO 1999/059646 A1 | 11/1999 |
| WO | WO 2000/079497 A1 | 12/2000 |
| WO | WO 2002/17362 A2 | 2/2002 |
| WO | WO 2002/047162 A2 | 6/2002 |
| WO | WO 2003/021679 A2 | 3/2003 |
| WO | WO 2004/084720 A2 | 10/2004 |
| WO | WO 2005/083546 A1 | 9/2005 |
| WO | WO 2005/122285 A2 | 12/2005 |
| WO | WO 2006/013573 A2 | 2/2006 |
| WO | WO 2007/003019 A2 | 1/2007 |
| WO | WO 2007/024983 A2 | 3/2007 |
| WO | WO 2007/116344 A1 | 10/2007 |
| WO | WO 2007/136726 A2 | 11/2007 |
| WO | WO 2008/030960 A2 | 3/2008 |
| WO | WO 2008/055212 A2 | 5/2008 |
| WO | WO 2008/069682 A1 | 6/2008 |
| WO | WO 2008/143635 A1 | 11/2008 |
| WO | WO 2009/008892 A1 | 1/2009 |
| WO | WO 2009/036260 A1 | 3/2009 |
| WO | WO 2009/111641 A1 | 9/2009 |
| WO | WO 2009/114689 A1 | 9/2009 |
| WO | WO 2009/135070 A1 | 11/2009 |
| WO | WO 2010/029966 A1 | 3/2010 |
| WO | WO 2010/036807 A1 | 4/2010 |
| WO | WO 2010/042653 A1 | 4/2010 |
| WO | WO 2010/042957 A2 | 4/2010 |
| WO | WO 2010/046883 A1 | 4/2010 |
| WO | WO 2010/056857 A2 | 5/2010 |
| WO | WO 2010/081137 A2 | 7/2010 |
| WO | WO 2010/082993 A2 | 7/2010 |
| WO | WO 2010/102310 A2 | 9/2010 |
| WO | WO 2010/132552 A1 | 11/2010 |
| WO | WO 2011/003181 A1 | 1/2011 |
| WO | WO 2011/041727 A1 | 4/2011 |
| WO | WO 2011/084450 A1 | 7/2011 |
| WO | WO 2011/084709 A2 | 7/2011 |
| WO | WO 2011/124898 A1 | 10/2011 |
| WO | WO 2011/127331 A2 | 10/2011 |
| WO | WO 2012/094264 A2 | 7/2012 |
| WO | WO 2012/125494 A2 | 9/2012 |
| WO | WO 2012/166686 A2 | 12/2012 |
| WO | WO 2013/010171 A1 | 1/2013 |
| WO | WO 2013/022853 A1 | 2/2013 |
| WO | WO 2013/033724 A1 | 3/2013 |
| WO | WO 2013/034987 A3 | 3/2013 |
| WO | WO 2013/049716 A1 | 4/2013 |
| WO | WO 2013/052919 A2 | 4/2013 |
| WO | WO 2013/059671 A1 | 4/2013 |
| WO | WO 2013/063634 A1 | 5/2013 |
| WO | WO 2013/144738 A2 | 10/2013 |
| WO | WO 2013/144866 A1 | 10/2013 |
| WO | WO 2013/170032 A2 | 11/2013 |
| WO | WO 2014/007871 A1 | 1/2014 |
| WO | WO 2014/058473 A1 | 4/2014 |
| WO | WO 2014/059032 A1 | 4/2014 |
| WO | WO 2014/106041 A1 | 7/2014 |
| WO | WO 2014/110176 A1 | 7/2014 |
| WO | WO 2014/124044 A1 | 8/2014 |
| WO | WO 2014/124049 A2 | 8/2014 |
| WO | WO 2014/130928 A2 | 8/2014 |
| WO | WO 2014/130931 A1 | 8/2014 |
| WO | WO 2014/179343 A1 | 11/2014 |
| WO | WO 2014/186467 A2 | 11/2014 |
| WO | WO 2014/197443 A1 | 12/2014 |
| WO | WO 2014/205434 A2 | 12/2014 |
| WO | WO 2015/021039 A1 | 2/2015 |
| WO | WO 2015/054312 A1 | 4/2015 |
| WO | WO 2015/077559 A1 | 5/2015 |
| WO | WO 2015/080991 A1 | 6/2015 |
| WO | WO 2015/102951 A2 | 7/2015 |
| WO | WO 2015/103483 A1 | 7/2015 |
| WO | WO 2015/103580 A2 | 7/2015 |
| WO | WO 2015/120330 A1 | 8/2015 |
| WO | WO 2015/127458 A1 | 8/2015 |
| WO | WO 2015/134588 A1 | 9/2015 |
| WO | WO 2015/138712 A1 | 9/2015 |
| WO | WO 2015/145471 A1 | 10/2015 |
| WO | WO 2015/159280 A1 | 10/2015 |
| WO | WO 2016/010983 A1 | 1/2016 |
| WO | WO 2016/025430 A1 | 2/2016 |
| WO | WO 2016/025468 A2 | 2/2016 |
| WO | WO 2016/048888 A1 | 3/2016 |
| WO | WO 2016/054512 A1 | 4/2016 |
| WO | WO 2016/057318 A1 | 4/2016 |
| WO | WO 2016/081244 A1 | 5/2016 |
| WO | WO 2016/0127050 A1 | 8/2016 |
| WO | WO 2016/134306 A1 | 8/2016 |
| WO | WO 2016-140961 A1 | 9/2016 |
| WO | WO 2016/205385 A1 | 12/2016 |
| WO | WO 2017/015000 A1 | 1/2017 |
| WO | WO 2017/059215 A1 | 4/2017 |
| WO | WO 2017/062508 A1 | 4/2017 |
| WO | WO 2017/184705 A1 | 10/2017 |
| WO | WO 2018/013569 A1 | 1/2018 |
| WO | WO 2018/013656 A1 | 1/2018 |
| WO | WO 2018/057911 A1 | 3/2018 |
| WO | WO 2018/081778 A1 | 5/2018 |
| WO | WO 2018/085336 A1 | 5/2018 |
| WO | WO 2018/093751 A1 | 5/2018 |
| WO | WO 2018/119193 A1 | 6/2018 |
| WO | WO 2018/136462 A1 | 7/2018 |
| WO | WO 2018/208523 A1 | 11/2018 |

OTHER PUBLICATIONS

U.S. Appl. No. 14/859,680, filed Sep. 21, 2015, D. Garlock, Methods and Apparatuses for Shaping and Looping Bonding Wires That Serve as Stretchable and Bendable Interconnects.
U.S. Appl. No. 15/016,937, filed Feb. 5, 2016, Jesus Pindado et al., Method and System for Interacting with an Environment.
U.S. Appl. No. 15/057,762, filed Mar. 1, 2016, Brian Murphy et al., Perspiration Sensor.
U.S. Appl. No. 15/160,631, filed May 20, 2016, Lee et al., Ultra-Thin Wearable Sensing Device.
U.S. Appl. No. 15/183,513, filed Jun. 15, 2016, Wang et al., Moisture Wicking Adhesives for Skin Mounted Devices.
U.S. Appl. No. 15/189,461, filed Jun. 22, 2016, Ghaffari et al., Method and System for Structural Health Monitoring.
U.S. Appl. No. 15/208,444, filed Jul. 12, 2016, McGrane et al., Conductive Stiffener, Method of Making a Conductive Stiffener, and Conductive Adhesive and Encapsulation Layers.
U.S. Appl. No. 15/238,488, filed Aug. 16, 2016, Sun et al., Wearable Heat Flux Devices and Methods of Use.
U.S. Appl. No. 15/272,816, filed Sep. 22, 2016, Pindado et al., Method and System for Crowd-Sourced Algorithm Development.
U.S. Appl. No. 15/281,960, filed Sep. 30, 2016, Ghaffari et al., Method and System for Interacting with a Virtual Environment.
U.S. Appl. No. 15/286,129, filed Oct. 5, 2016, Ghaffari et al., Method and System for Neuromodulation and Stimulation.
U.S. Appl. No. 15/369,627, filed Dec. 5, 2016, Ghaffari et al., Cardiac Catheter Employing Conformal Electronics for Mapping.
U.S. Appl. No. 15/369,668, filed Dec. 5, 2016, Ghaffari et al., Cardiac Catheter Employing Conformal Electronics for Mapping.
U.S. Appl. No. 15/373,159, filed Dec. 8, 2016, Ghaffari et al., Catheter Balloon Methods and Apparatus Employing Sensing Elements.

(56) References Cited

OTHER PUBLICATIONS

U.S. Appl. No. 15/373,162, filed Dec. 8, 2016, Ghaffari et al., Catheter Balloon Methods and Apparatus Employing Sensing Elements.
U.S. Appl. No. 15/373,165, filed Dec. 8, 2016, Ghaffari et al., Catheter Balloon Methods and Apparatus Employing Sensing Elements.
U.S. Appl. No. 15/405,166, filed Jan. 12, 2017, Rafferty et al., Electronics for Detection of a Condition of Tissue.
U.S. Appl. No. 15/413,218, filed Jan. 23, 2017, Rafferty et al, Electronics for Detection of a Condition of Tissue.
U.S. Appl. No. 15/433,873, filed Feb. 15, 2017, Rafferty et al., Electronics for Detection of a Condition of Tissue.
U.S. Appl. No. 15/437,967, filed Feb. 21, 2017, Raj et al., System, Device, and Method for Coupled Hub and Sensor Node On-Body Acquisition of Sensor Information.
U.S. Appl. No. 15/457,852, filed Mar. 13, 2017, Dalal et al., Discrete Flexible Interconnects for Modules of Integrated Circuits.
U.S. Appl. No. 15/464,006, filed Mar. 20, 2017, Ghaffari et al., Systems, Methods, and Devices Using Stretchable or Flexible Electronics for Medical Applications.
U.S. Appl. No. 15/491,379, filed Apr. 19, 2017, Ghaffari et al., Method and System for Measuring Perspiration.
U.S. Appl. No. 15/498,941, filed Apr. 27, 2017, De Graff et al., Systems, Methods, and Devices Having Stretchable Integrated Circuitry for Sensing and Delivering Therapy.
U.S. Appl. No. 15/526,375, filed May 12, 2017, Aranyosi et al., System, Device, and Method for Electronic Device Activation.
U.S. Appl. No. 15/614,469, filed Jun. 5, 2017, Hsu et al., Conformal Electronics Including Nested Serpentine Interconnects.
U.S. Appl. No. 15/661,172, filed Jul. 27, 2017, Ghaffari et al., Catheter Balloon Employing Force Sensing Elements.
U.S. Appl. No. 15/806,162, filed Nov. 7, 2017, Hsu et al., Strain Isolation Structures for Stretchable Electronics.
U.S. Appl. No. 15/850,129, filed Dec. 21, 2017, Arora et al., Extremely Stretchable Electronics.
U.S. Appl. No. 15/850,523, filed Dec. 21, 2017, Huppert et al., Buffered Adhesive Structures for Wearable Patches.
U.S. Appl. No. 15/869,371, filed Jan. 12, 2018, Ives, Utility Gear Including Conformal Sensors.
U.S. Appl. No. 15/875,556, filed Jan. 19, 2018, Kacyvenski et al., Motion Sensor and Analysis.
U.S. Appl. No. 16/212,154, filed Dec. 6, 2018, De Graff et al., Systems, Methods, and Devices Having Stretchable Integrated Circuitry for Sensing and Delivering Therapy.
U.S. Appl. No. 16/297,032, filed Mar. 8, 2019, Huppert et al., Conformal Sensor Systems for Sensing and Analysis of Cardiac Activity.
U.S. Appl. No. 16/385,364, filed Apr. 16, 2019, Wang, Moisture Wicking Adhesives for Skin-Mounted Devices.
U.S. Appl. No. 16/399,325, filed Apr. 30, 2019, Ghaffari et al., Method and System for Interacting with a Virtual Environment.
U.S. Appl. No. 16/346,588, filed May 1, 2019, Huppert et al., Materials and Methods for the Quantification of a Fluid.
U.S. Appl. No. 16/478,798, filed Jul. 17, 2019, Raj et al., Digital Stethoscope Using Mechano-Acoustic Sensor Suite.
U.S. Appl. No. 16/519,781, filed Jul. 23, 2019, McMahon et al, Encapsulated Conformal Electronic Systems and Devices, and Methods of Making and Using the Same.
U.S. Appl. No. 16/576,218, filed Sep. 19, 2019, Ghaffari et al., Conformal Sensor Systems for Sensing and Analysis.
U.S. Appl. No. 16/600,189, filed Oct. 11, 2019, Elolampi et al., Multi-Part Flexible Encapsulation Housing for Electronic Devices.
U.S. Appl. No. 16/612,330, filed Nov. 8, 2019, Raj et al., Optical Flow Simulators and Methods of Using the Same.
Carvalhal et al., "Electrochemical Detection in a Paper-Based Separation Device", Analytical Chemistry, vol. 82, No. 3, (1162-1165) (4 pages) (Jan. 7, 2010).

Demura et al., "Immobilization of Glucose Oxidase with *Bombyx mori* Silk Fibroin by Only Stretching Treatment and its Application to Glucose Sensor," Biotechnology and Bioengineering, vol. 33, 598-603 (6 pages) (1989).
Ellerbee el al., "Quantifying Colorimetric Assays in Paper-Based Microfluidic Devices by Measuring the Transmission of Light through Paper," Analytical Chemistry, vol. 81, No. 20 8447-8452, (6 pages) (Oct. 15, 2009).
Halsted, "Ligature and Suture Material," Journal of the American Medical Association, vol. LX, No. 15, 1119-1126, (8 pages) (Apr. 12, 1913).
Kim et al., "Complementary Metal Oxide Silicon Integrated Circuits Incorporating Monolithically Integrated Stretchable Wavy Interconnects," Applied Physics Letters, vol. 93, 044102-044102.3 (3 pages) (Jul. 31, 2008).
Kim et al., "Dissolvable Films of Silk Fibroin for Ultrathin Conformal Bio-Integrated Electronics," Nature, 1-8 (8 pages) (Apr. 18, 2010).
Kim et al., "Materials and Noncoplanar Mesh Designs for Integrated Circuits with Linear Elastic Responses to Extreme Mechanical Deformations," PNAS, vol. 105, No. 48, 18675-18680 (6 pages) (Dec. 2, 2008).
Kim et al., "Stretchable and Foldable Silicon Integrated Circuits," Science, vol. 320, 507-511 (5 pages) (Apr. 25, 2008).
Kim et al., "Electrowetting on Paper for Electronic Paper Display," ACS Applied Materials & Interfaces, vol. 2, No. 11, (3318-3323) (6 pages) (Nov. 24, 2010).
Ko et al., "A Hemispherical Electronic Eye Camera Based on Compressible Silicon Optoelectronics," Nature, vol. 454, 748-753 (6 pages) (Aug. 7, 2008).
Lawrence et al., "Bioactive Silk Protein Biomaterial Systems for Optical Devices," Biomacromolecules, vol. 9, 1214-1220 (7 pages) (Nov. 4, 2008).
Meitl et al., "Transfer Printing by Kinetic Control of Adhesion to an Elastomeric Stamp," Nature, vol. 5, 33-38 (6 pages) (Jan. 2006).
Omenetto et al., "A New Route for Silk," Nature Photonics, vol. 2, 641-643 (3 pages) (Nov. 2008).
Omenetto et al., "New Opportunities for an Ancient Material," Science, vol. 29, 528-531 (5 pages) (Jul. 30, 2010).
Siegel et al., "Foldable Printed Circuit Boards on Paper Substrates," Advanced Functional Materials, vol. 20, No. 1, 28-35, (8 pages) (Jan. 8, 2010).
Tsukada et al., "Structural Changes of Silk Fibroin Membranes Induced by Immersion in Methanol Aqueous Solutions," Journal of Polymer Science, vol. 32, 961-968 (8 pages) (1994).
Wang et al., "Controlled Release From Multilayer Silk Biomaterial Coatings to Modulate Vascular Cell Responses" Biomaterials, 29, 894-903 (10 pages) (Nov. 28, 2008).
Wikipedia, "Ball bonding" article [online]. Cited in PCT/US2015/051210 search report dated Mar. 1, 2016 with the following information "Jun. 15, 2011 [retrieved on Nov. 11, 2015}. Retrieved Dec. 2018, 29 from the Internet: <URL: https://web.archive.org/web/20110615221003/hltp://en.wikipedia.org/wiki/Ball_bonding>., entire document, especially para 1, 4, 5, 6," 2 pages, last page says ("last modified on May 11, 2011").
Bossuyt et al., "Stretchable Electronics Technology for Large Area Applications: Fabrication and Mechanical Characterizations", vol. 3, pp. 229-235 (7 pages) (Feb. 2013).
Jones et al., "Stretchable Interconnects for Elastic Electronic Surfaces". vol. 93, pp. 1459-1467 (9 pages) (Aug. 2005).
Lin et al., "Design and Fabrication of Large-Area, Redundant, Stretchable Interconnect Meshes Using Excimer Laser Photoablation and In Situ Masking", (10 pages) (Aug. 2010).
Kim et al., "A Biaxial Stretchable Interconnect With Liquid-Alloy-Covered Joints on Elastomeric Substrate", vol. 18, pp. 138-146 (9 pages) (Feb. 2009).
Kinkeldi et al., "Encapsulation for Flexible Electronic Devices", IEE Electron Device Letters, 32(12):1743-5 (2011).
Hsu et al., "Epidermal electronics: Skin sweat patch", Microsystems, Packaging, Assembly and Circuits Technology Conference (IMPACT), 2012 7th International. IEEE, 2012.
Siegel et al.,"Foldable printed circuit boards on paper substrates", Advanced Functional Materials, 20:28-35 (2010).

(56) References Cited

OTHER PUBLICATIONS

Ellerbee et al.,"Quantifying colorimetric assays in paper-based microfluidic devices by measuring the transmission of light through paper", Anal. Chem.,81(20):8447-52 (2009).
Wehner et al.; "A Lightweight Soft Exosuit for Gait Assistance"; IEEE International Conference on Robotics and Automation (ICRA), May 6-10, 2013. Retrieved from https://micro.seas.harvard.edu/papers/Wehner_ICRA13.pdf (8 pages).
Cauwe et al., "Flexible and Stretchable Circuit Technologies for Space Applications," 5$^{th}$ Electronic Materials, Processes and Packaging for Space, May 20-22, 2014 (18 pages).
Hild, "Surface Energy of Plastics," Dec. 16, 2009. Retrieved from https://www.tstar.com/blog/bid/33845/surface-enery-of-plastics (3 pages).
Hodge et al., "A Microcolorimetric Method for the Determination of Chloride," Microchemical Journal, vol. 7, Issue 3, Sep. 30, 1963, pp. 326-330 (5 pages).
Bonifacio et al., "An improved flow system for chloride determination in natural waters exploiting solid-phase reactor and long pathlength spectrophotometry," Talanta, vol. 72, Issue 2, Apr. 30, 2007, pp. 663-667 (5 pages).
Meyer et al., "The Effect of Gelatin Cross-Linking on the Bioequivalence of Hard and Soft Gelatin Acetaminophen Capsules," Pharmaceutical Research, vol. 17, No. 8, Aug. 31, 2000, pp. 962-966 (5 pages).
Bang et al.; "The Smart House for Older Persons and Persons With Disabilities: Structure, Technology Arrangements, and Perspectives"; IEEE Transactions on Neural Systems and Rehabilitation Engineering, IEEE Service Center, New York, New York; vol. 12, No. 2, pp. 228-250; Jun. 1, 2004; XP011113818; ISSN: 1534-4320 (23 pages).
Duan et al.; "High Performance thin-film transistors using semiconductor nanowires and nanoribbons"; Nature, vol. 425, pp. 274-278; Sep. 2003 (5 pages).
J. Kim et al.; "Miniaturized Flexible Electronic Systems with Wireless Power and Near-Field Communication Capabilities"; Advanced Function Materials, 2015, vol. 25, pp. 4761-4767; XP55420377 (7 pages).
V. Curto et al.; "Wearable Micro-Fluidic pH Sweat Sensing Device Based on Colorimetric Imaging Technologies"; 15th International Conference on Miniaturized Systems for Chemistry and Life Sciences, Oct. 2, 2011; pp. 577-579; XP55525572 (3 pages).
J. Kim et al.; "Epidermal Electronics with Advanced Capabilities in Near-Field Communication"; Small, vol. 11, No. 8, pp. 906-912; Feb. 1, 2015; XP055632692 (7 pages).
Lin Hao et al.; "Noninvasive and Continuous Blood Pressure Monitoring Using Wearable Body Sensor Networks"; IEEE Intelligent Systems, IEEE, US, vol. 30, No. 6, pp. 38-48; Sep. 23, 2015; XP011589366 (11 pages).
J. Franco et al.; "Continuous, Non-invasive and Cuff-free Blood Pressure Monitoring System"; Andean Region International Conference, 2012 VI, IEEE, Nov. 7, 2012; pp. 31-34; XP032419437 (4 pages).
International Search Report, PCT/US2016/018757, dated Jun. 30, 2016 (4 pages).
Written Opinion of the International Searching Authority, PCT/US2016/018757, dated Jun. 30, 2016 (16 pages).
Extended European Search Report, EP 16753182.1, dated Jun. 9, 2018 (18 pages).
U.S. Appl. No. 12/968,637, filed Dec. 15, 2010, J. Rogers, High-Speed, High-Resolution Electrophysiology In-Vivo Using Conformal Electronics.
U.S. Appl. No. 13/492,636, filed Jun. 8, 2012, J. Rogers, Flexible and Stretchable Electronic Systems for Epidermal Electronics.
U.S. Appl. No. 14/521,319, filed Oct. 22, 2014, J. Rogers, Stretchable and Foldable Electronic Devices.
U.S. Appl. No. 14/706,733, filed May 7, 2015, J. Rogers, Stretchable and Foldable Electronic Devices.
U.S. Appl. No. 15/084,112, filed Mar. 29, 2016, J. Rogers, Controlled Buckling Structures in Semiconductor Interconnects and Nanomembranes for Stretchable Electronics.
U.S. Appl. No. 15/339,338, filed Oct. 31, 2016, J. Rogers, A Stretchable Form of Single Crystal Silicon for High Performance Electronics on Rubber.
U.S. Appl. No. 15/470,780, filed Mar. 27, 2017, J. Rogers, Printed Assemblies of Ultrathin, Microscale Inorganic Light Emitting Diodes for Deformable and Semitransparent Displays.
U.S. Appl. No. 15/805,674, filed Nov. 7, 2017, Litt et al., Flexible and Scalable Arrays for Recording and Modulating Physiologic Activity.
U.S. Appl. No. 16/448,988, filed Jun. 21, 2019, Dahl-young et al., Methods and Devices for Fabricating and Assembling Printable Semiconductor Elements.

\* cited by examiner

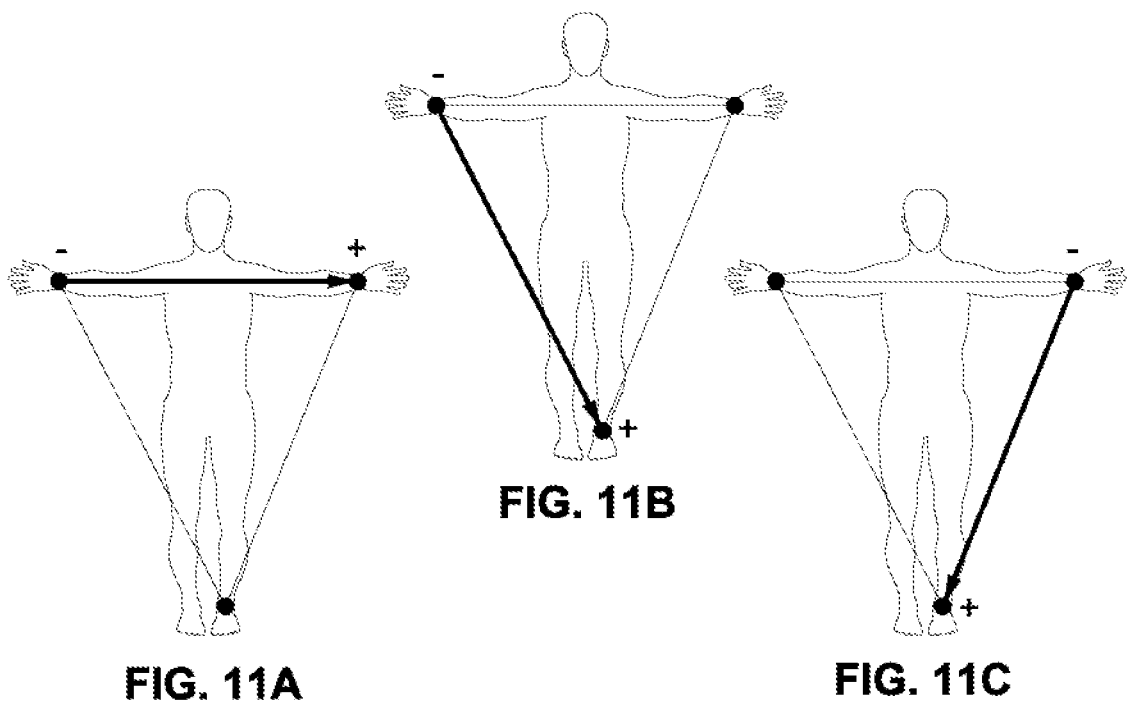
FIG. 11A  FIG. 11B  FIG. 11C
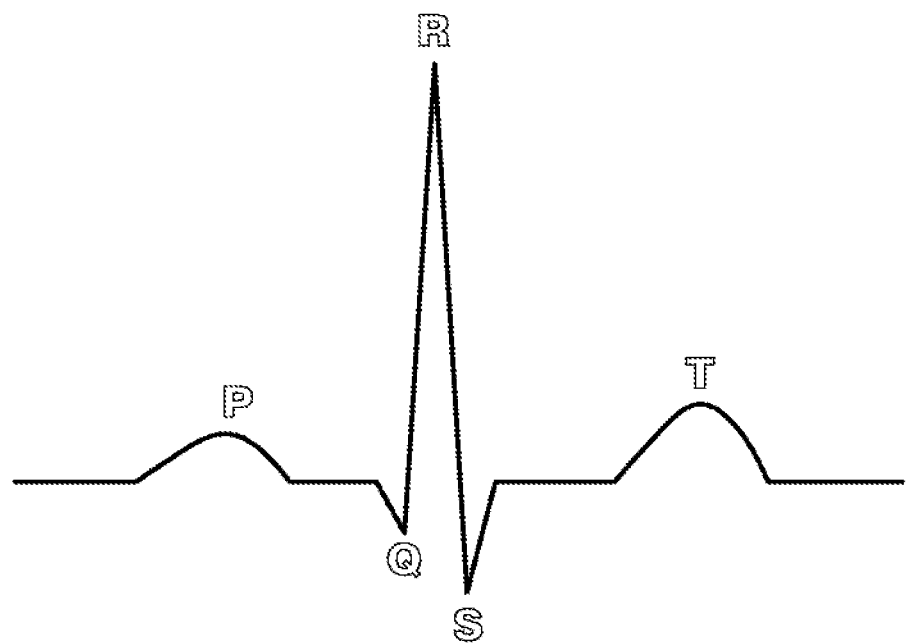
FIG. 12

AUTOMATED DETECTION AND CONFIGURATION OF WEARABLE DEVICES BASED ON ON-BODY STATUS, LOCATION, AND/OR ORIENTATION

CROSS-REFERENCE TO RELATED APPLICATIONS

This application is a continuation of U.S. application Ser. No. 15/048,576, entitled "AUTOMATED DETECTION AND CONFIGURATION OF WEARABLE DEVICES BASED ON ON-BODY STATUS, LOCATION, AND/OR ORIENTATION," filed Feb. 19, 2016, now allowed, which claims the benefit of U.S. Provisional Application No. 62/118,843, entitled "AUTOMATED DETECTION OF ON-BODY LOCATION OF A WEARABLE DEVICE," filed Feb. 20, 2015, and U.S. Provisional Application No. 62/171,414, entitled "AUTOMATED DETECTION OF ON-BODY STATUS AND LOCATION OF A WEARABLE DEVICE," filed Jun. 5, 2015, each of which is hereby incorporated by reference herein in its entirety, including drawings.

TECHNICAL FIELD

The present disclosure relates generally to sensors. More particularly, aspects of this disclosure relate to sensors wearable on a body, such as a human body.

BACKGROUND

Integrated circuits (ICs) are the cornerstone of the information age and the foundation of today's information technology industries. The integrated circuit, a.k.a. "chip" or "microchip," is a set of interconnected electronic components, such as transistors, capacitors, and resistors, which are etched or imprinted onto a semiconducting material, such as silicon or germanium. Integrated circuits take on various forms including, as some non-limiting examples, microprocessors, amplifiers, Flash memories, application specific integrated circuits (ASICs), static random access memories (SRAMs), digital signal processors (DSPs), dynamic random access memories (DRAMs), erasable programmable read only memories (EPROMs), and programmable logic. Integrated circuits are used in innumerable products, including computers (e.g., personal, laptop and tablet computers), smartphones, flat-screen televisions, medical instruments, telecommunication and networking equipment, airplanes, watercraft and automobiles.

Advances in integrated circuit technology and microchip manufacturing have led to a steady decrease in chip size and an increase in circuit density and circuit performance. The scale of semiconductor integration has advanced to the point where a single semiconductor chip can hold tens of millions to over a billion devices in a space smaller than a U.S. penny. Moreover, the width of each conducting line in a modern microchip can be made as small as a fraction of a nanometer. The operating speed and overall performance of a semiconductor chip (e.g., clock speed and signal net switching speeds) has concomitantly increased with the level of integration. To keep pace with increases in on-chip circuit switching frequency and circuit density, semiconductor packages currently offer higher pin counts, greater power dissipation, more protection, and higher speeds than packages of just a few years ago.

The advances in integrated circuits have led to related advances within other fields. One such field is sensors. Advances in integrated circuits have allowed sensors to become smaller and more efficient, while simultaneously becoming more capable of performing complex operations. Other advances in the field of sensors and circuitry in general have led to wearable circuitry, a.k.a. "wearable devices" or "wearable systems." Within the medical field, as an example, wearable devices have given rise to new methods of acquiring, analyzing, and diagnosing medical issues with patients, by having the patient wear a sensor that monitors specific characteristics. Related to the medical field, other wearable devices have been created within the sports and recreational fields for the purpose of monitoring physical activity and fitness. For example, a user may don a wearable device, such as a wearable running coach, to measure the distance traveled during an activity (e.g., running, walking, etc.), and measure the kinematics of the user's motion during the activity.

However, current wearable devices rely on a user to select whether the device is coupled to or decoupled from the body (e.g., determine on-body status) and to select the location and/or orientation of the device on the body. Current wearable devices also rely on a user to enter such location and/or orientation information into the device and/or a system associated with reading and processing the information provided by the wearable device (e.g., mobile device associated with the wearable device). This on-body status, location, and orientation information is useful for the device (or system) to configure its operation appropriately. Alternatively, current wearable devices are limited to deriving generic metrics that are not location and/or orientation dependent. These shortcomings of current wearable devices introduce burdens on the user and a possibility for making mistakes, such as incorrectly placing and/or orientating the wearable device or incorrectly entering the location and/or orientation of the wearable device. These shortcomings prevent a seamless experience of using a wearable device and limit the functionality.

SUMMARY

According to some embodiments, an electronic device worn on a user includes one or more sensors (e.g., accelerometers, skin temperature sensors). For example, the electronic device can include one or more accelerometers that are configured to generate acceleration information based on acceleration experienced by the electronic apparatus. The electronic apparatus further includes a processor and one or more associated memories, and one or more memories can include computer program code executable by the processor. The processor, configured by the computer program code, causes the electronic device to process the acceleration information to extract features from the acceleration information. The processor can use the features to determine the location of the electronic device on the user, particularly without user input.

In yet another aspect of the present concepts, a method is directed to determining a location of a wearable device on a user as a function of sensor data and without user input. The method includes generating sensor information (e.g., acceleration information) based on environmental conditions (e.g., acceleration) experienced by the wearable device. The generated acceleration information is then processed to extract features from the acceleration information. The one or more features are then processed to determine the location of the wearable device (or sensor) on the user, without user input.

According to further aspects of the present concepts, an electronic device worn on a user that includes one or more accelerometers is disclosed. The one or more accelerometers are configured to generate acceleration information based on acceleration experienced by the electronic device during a first period of time or for a set of sensor data points. The electronic device further includes a processor and one or more associated memories, and at least one of the memories can include computer program code. The processor, according to the computer program code, can be configured to control the electronic device and cause the electronic device to extract features from the acceleration information. The features characterize the acceleration information during the first period of time. The processor can be further configured to cause the electronic device to determine the location of the wearable device (or sensor) on the user as one of a plurality of predefined locations based on the features. Further, the processor can be configured by the computer program code to cause the electronic device to configure the functionality of the device based on the detected location and, optionally, one or more location-specific metrics associated with the one of the plurality of predefined locations.

In accordance with another aspect of the present concepts, a method is directed to configuring a wearable device based on the wearable device determining its location on a user as a function of sensor information without input from the user. The method can include determining acceleration information during a first period of time (or for a set of sensor data points) based on one or more accelerometers included within the wearable device. One or more features are then extracted from the acceleration information, in which the one or more features characterize the acceleration information during the first period. The location of the wearable device is then determined as one of a plurality of predefined locations based on the one or more features. The wearable device is then configured based on the location and, optionally, one or more location-specific metrics associated with the one of the plurality of predefined locations.

According to further aspects of the present concepts, a wearable electronic device is disclosed. The wearable electronic device can be adhered to the body by an adhesive or positioned against the body by straps or clothing. The electronic device can include a temperature sensor configured to measure temperature information associated with the electronic device. The electronic device also includes a processor and one or more associated memories. The one or more associated memories include computer program code executable by the processor. The processor can be configured by the computer program code to cause the electronic device to process the temperature information to determine a temperature, a change in temperature, a rate of change in temperature, or a combination thereof, and determine an on-body status of the electronic device on the user based on the temperature, the change in temperature, the rate of the change in temperature, or a combination thereof.

In accordance with another aspect of the present concepts, a method is directed to determining a status of an electronic device. The method includes measuring temperature information associated with the electronic device based on a temperature sensor that forms a part of the electronic device, processing the temperature information to determine a temperature, a change in temperature, a rate of change in temperature, or a combination thereof, and determining an on-body status of the electronic device based, at least in part, on the temperature, the change in temperature, the rate of change in temperature, or a combination thereof. For example, the temperature sensor of the electronic device can be positioned against the body and used to determine the temperature of that portion of body (e.g., skin temperature).

According to yet another aspect of the present concepts, a method is directed to configuring a wearable device. The method includes generating acceleration information based on acceleration experienced by one or more motion sensors within the wearable device. The method further includes measuring temperature information experienced by the wearable device based on a temperature sensor within the wearable device. The method also includes determining an on-body status of the wearable device based on the acceleration information, the temperature information, or a combination thereof. The method additionally includes configuring functionality of the wearable device based, at least in part, on the on-body status.

According to additional aspects, an electronic device worn on a user includes one or more accelerometers and temperature sensors configured to generate acceleration information and temperature information based on acceleration and skin temperature experienced by the electronic device. The electronic device further includes a processor and memory, the memory including computer program code. The memory and the computer program code are configured to, with the processor, cause the electronic device to process the acceleration and skin temperature information to extract features from the acceleration information. The memory and the computer program code are further configured to, with the processor, cause the electronic device to process the features to determine a location of the electronic device on the user.

According to another aspect, an electronic device worn on a user is disclosed. The electronic device includes at least two electrical contacts configured to detect an electrical signal at the surface of the user. In particular, the electrical signal is an electrocardiogram signal. The device further includes an accelerometer configured to generate acceleration information experienced by the at least two electrical contacts, a processor, and one or more associated memories. The one or more associated memories include computer program code executable by the processor which causes the electronic device to acquire the electrical signal at the surface of the user through the at least two electrical contacts. The computer program code executable by the processor further causes the electronic device to process the acceleration information generated by the accelerometer to determine an orientation of the at least two electrical contacts relative to the user, and determine which limb lead electrocardiogram signal the electrical signal represents based on the orientation.

Further aspects of the present disclosure include a sensor system worn on a surface of a user. The sensor system includes at least three wearable devices located at three different locations on the surface. Each wearable device includes a pair of electrical contacts configured to detect an electrical signal at the surface; the electrical signal being specifically an electrocardiogram signal. Each wearable device also includes an accelerometer configured to generate acceleration information experienced by the wearable device. The system further includes a processor and one or more associated memories. The one or more associated memories include computer program code executable by the processor that causes the processor to cause the three pairs of electrical contacts to acquire electrical signals, each electrical signal being from one of the three different locations at the surface of the user. The computer program code executable by the processor further causes the processor to process the acceleration information generated by the three accelerometers to determine orientations of the three pairs of electrical contacts relative to the user. The computer program code executable by the processor further causes the processor to assign limb leads to the electrical signals based on the orientations of the three pairs of electrical contacts.

Additional aspects include a method of classifying an electrical signal within an electrocardiography process. The method includes attaching a wearable device to a surface of a user. The wearable device includes a pair of electrical contacts configured to detect an electrical signal at the surface of the user. Specifically, the electrical signal is an electrocardiogram signal. The wearable device further includes an accelerometer configured to generate acceleration information experienced by the pair of electrical contacts. The method further includes detecting the electrical signal at the surface of the user with the pair of electrical contacts. The method further includes determining an orientation of the pair of electrical contacts relative to the user based on the acceleration information, and determining whether the electrical signal represents a Lead I, Lead II, or Lead III electrocardiogram signal based on the orientation.

The above summary is not intended to represent each embodiment or every aspect of the present disclosure. Rather, the foregoing summary merely provides an exemplification of some of the novel aspects and features set forth herein. The above features and advantages, and other features and advantages of the present disclosure, will be readily apparent from the following detailed description of representative embodiments and modes for carrying out the present invention when taken in connection with the accompanying drawings and the appended claims.

BRIEF DESCRIPTION OF THE DRAWINGS

The disclosure will be better understood from the following description of exemplary embodiments together with reference to the accompanying drawings, in which:

FIG. 11A shows the electrode arrangement for detecting Lead I of the lead limbs on the human body in accord with aspects of the present disclosure;

FIG. 11B shows the electrode arrangement for detecting Lead II of the lead limbs on the human body in accord with aspects of the present disclosure;

FIG. 11C shows the electrode arrangement for detecting Lead III of the lead limbs on the human body in accord with aspects of the present disclosure;

FIG. 12 shows elements of a normal electrocardiography (ECG) tracing in accord with aspects of the present disclosure;

Figure 1:
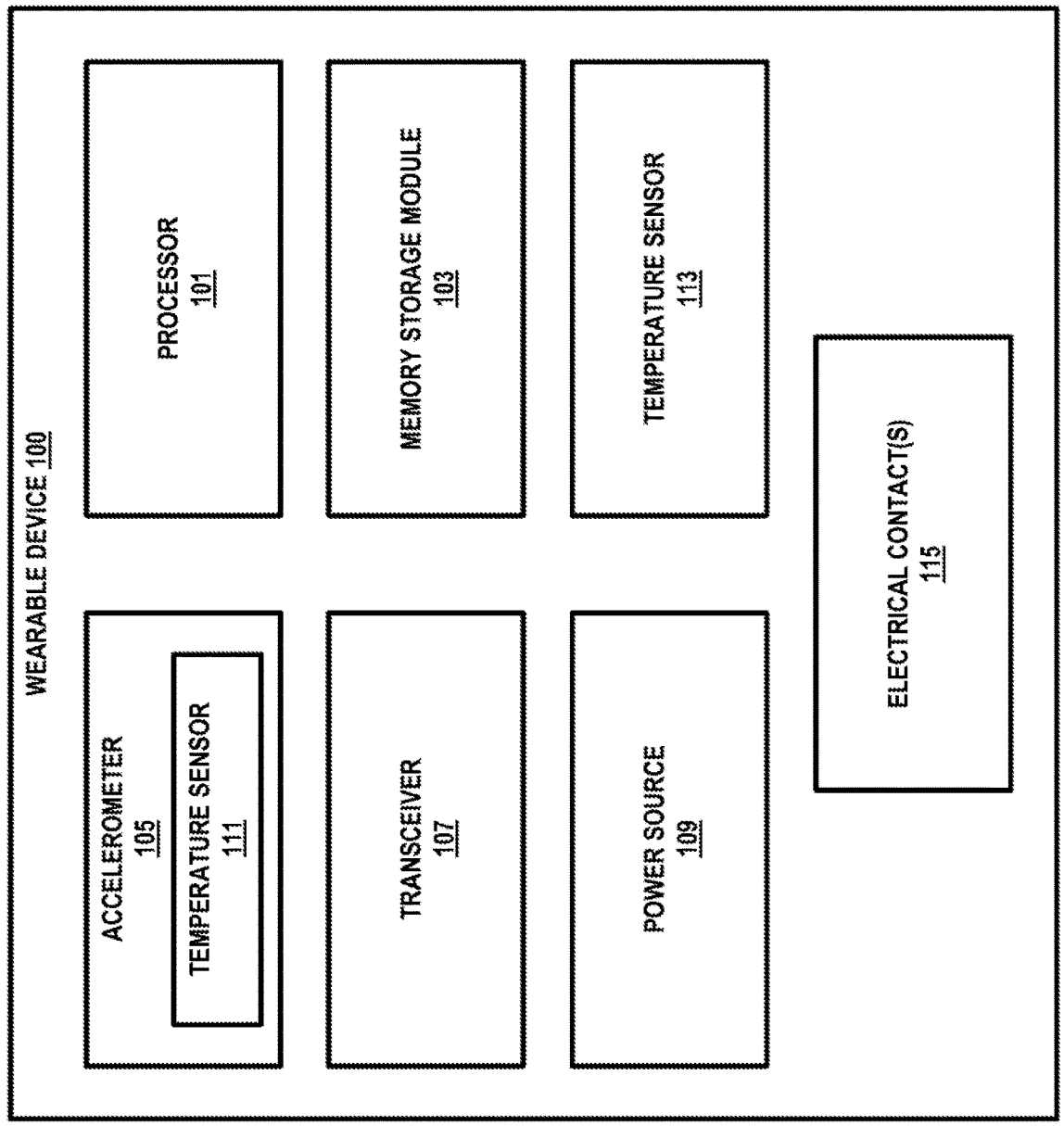
FIG. 1 illustrates a wearable device in accord with aspects of the present disclosure.

The present disclosure is susceptible to various modifications and alternative forms, and some representative embodiments have been shown by way of example in the drawings and will be described in detail herein. It should be understood, however, that the invention is not intended to be limited to the particular forms disclosed. Rather, the disclosure is to cover all modifications, equivalents, and alternatives falling within the spirit and scope of the invention as defined by the appended claims.

DETAILED DESCRIPTION OF THE ILLUSTRATED EMBODIMENTS

This disclosure is susceptible of embodiment in many different forms. There are shown in the drawings, and will herein be described in detail, representative embodiments with the understanding that the present disclosure is to be considered as an exemplification of the principles of the present disclosure and is not intended to limit the broad aspects of the disclosure to the embodiments illustrated. To that extent, elements and limitations that are disclosed, for example, in the Abstract, Summary, and Detailed Description sections, but not explicitly set forth in the claims, should not be incorporated into the claims, singly or collectively, by implication, inference, or otherwise. For purposes of the present detailed description, unless specifically disclaimed: the singular includes the plural and vice versa; and the word "including" means "including without limitation." Moreover, words of approximation, such as "about," "almost," "substantially," "approximately," and the like, can be used herein in the sense of "at, near, or nearly at," or "within 3-5% of," or "within acceptable manufacturing tolerances," or any logical combination thereof, for example.

FIG. 1 shows an example of a wearable device 100 in accord with aspects of the present disclosure. The wearable device 100 provides conformal sensing capabilities, providing mechanically transparent close contact with a surface (such as the skin or other portion of the body) to provide measurement and/or analysis of physiological information. According to some embodiments, the wearable device 100 senses, measures, or otherwise quantifies the motion of at least one body part of a user upon which the wearable device 100 is located. Additionally, or in the alternative, according to some embodiments, the wearable device 100 senses, measures, or otherwise quantifies the temperature of the environment of the wearable device 100, including, for example, the skin and/or body temperature at the location that the wearable device 100 is coupled to the body of a user. Additionally, or in the alternative, according to some embodiments, the wearable device 100 senses, measures, or otherwise quantifies other characteristics and/or parameters of the body (e.g., human or animal body) and/or surface of the body, including, for example, electrical signals associated with cardiac activity (e.g., ECG), electrical signals associated with muscle activity (e.g., electromyography (EMG)), changes in electrical potential and impedance associated with changes to the skin, electrical signals of the brain (e.g., electroencephalogram (EEG)), bioimpedance monitoring (e.g., body-mass index, stress characterization, and sweat quantification), and optically modulated sensing (e.g., photoplethysmography and pulse-wave velocity), and the like.

The wearable device 100 described herein can be formed as a patch. The patch can be flexible and stretchable, and can be formed from conformal electronics and conformal electrodes disposed in or on a flexible and/or stretchable substrate. Alternatively, the wearable device 100 may be rigid but otherwise attachable to a user. Thus, the wearable device 100 can be any device that is wearable on a user, such as coupled to the skin of the user, to provide measurement and/or analysis of physiological information of the user. For example, the wearable device can be adhered to the body by adhesive, held in place against the body by tape or straps, or held in place against the body by clothing.

In general, the wearable device 100 device of FIG. 1 can include a processor 101 and associated memory storage module 103. The wearable device 100 further includes one or more sensors, such as an accelerometer 105 and/or a temperature sensor 113. The wearable device 100 can optionally include one or more wireless transceivers, such as transceiver 107, for communicating with other devices. The wearable device 100 can also include a power source 109 that provides power for the components of the wearable device 100. In accordance with some embodiments, the wearable device 100 can be configured to draw power from a wireless connection or an electromagnetic field (e.g., an induction coil, an NFC reader device, microwaves, and light).

The processor 101 can be a controller that is configured to control the wearable device 100 and components thereof based on computer program code. Thus, the processor 101 can control the wearable device 100 to measure and quantify data indicative of temperature, motion and/or other physiological data, and/or analyze such data indicative of temperature, motion and/or other physiological data according to the principles described herein.

The memory storage module 103 can be configured to save the generated sensor data (e.g., accelerometer 105 information, temperature sensor 113 information, or other physiological information, such as ECG, EMG, etc.) or information representative of acceleration and/or temperature and/or other physiological information derived from the sensor data. Further, according to some embodiments, the memory storage module 103 can be configured to store the computer program code that controls the processor 101. In some implementations, the memory storage module 103 can be volatile and/or non-volatile memory. For example, the memory storage module 103 can include flash memory, static memory, solid state memory, removable memory cards, or any combination thereof. In certain examples, the memory storage module 103 can be removable from the wearable device 100. In some implementations, the memory storage module 103 can be local to the wearable device 100, while in other examples the memory storage module 103 can be remote from the wearable device 100. For example, the memory storage module 103 can be internal memory of a smartphone that is in wired or wireless communication with the wearable device 100, such as through radio frequency communication protocols including, for example, WiFi, Zigbee, Bluetooth®, and near-field communication (NFC), and/or optically using, for example, infrared or non-infrared LEDs. In such an example, the wearable device 100 can optionally communicate with the smartphone via an application (e.g., program) executing on the smartphone.

In some embodiments, the generated data, including the temperature information, the acceleration information, and/or the other physiological information (e.g., ECG, EMG, etc.), can be stored on the memory storage module 103 for processing at a later time. Thus, in some embodiments, the wearable device 100 can include more than one memory storage module 103, such as one volatile and one non-volatile memory storage module 103. In other examples, the memory storage module 103 can store the information indicative of motion (e.g., acceleration information), temperature information, physiological data, or analysis of such information indicative of motion, temperature, physiological data according to the principles described herein, such as storing historical acceleration information, historical temperature information, historical extracted features, and/or historical locations. The memory storage module 103 can also store time and/or date information about when the information was received from the sensor.

Although described as the processor 101 being configured according to computer program code, the functionality of the wearable device 100 can be implemented based on hardware, software, or firmware or a combination thereof. For example, the memory storage module 103 can include computer program code that can be retrieved and executed by the processor 101. The processor 101 executes the computer program code that implements the functionality discussed below with respect to determining the on-body status of the wearable device 100, the location of the wearable device 100 on a user, and configuring functionality of the wearable device 100. Alternatively, one or more other components of the wearable device 100 can be hardwired to perform some or all of the functionality.

The power source 109 can be any type of power source for an electronic device, such as, but not limited to, one or more electrochemical cells or batteries, one or more capacitors, one or more photovoltaic cells, one or more piezoelectric elements, or a combination thereof. The one or more electrochemical cells or batteries can be rechargeable or non-rechargeable. In the case of the photovoltaic cells, the cells can charge one or more electrochemical cells and/or batteries. In accordance with some embodiments, the power source 109 can be a small battery or capacitor that stores enough energy for the device to power up and execute a predefined program sequence before running out of energy, for example, an NFC sensing device. In this embodiment, when an NFC reader is placed in proximity to the NFC device, the NFC reader's electromagnetic field induces a charging current in the coil of the NFC device that enables the device to power up and execute some or all of its computer program code.

As discussed above, the wearable device 100 further includes one or more sensors, such as the accelerometer 105, the temperature sensor 113, and/or electrical contacts 115 (e.g., electrical contacts or electrodes). In accordance with some embodiments, one or more of the sensors, such as accelerometer 105 and/or electrical contacts 115, can be separate components from the wearable device 100. That is, the wearable device 100 can be connected (by wire or wirelessly) to each sensor (e.g., accelerometer 105, temperature sensor 113, electrical contacts 115). This enables the wearable device 100 to sense information at one or more locations that are remote from the wearable device 100. In accordance with some embodiments, the wearable device 100 can include one or more integral sensors in addition to one or more remote sensors.

The accelerometer 105 measures and/or generates acceleration information indicative of a motion and/or acceleration of the wearable device 100, including information indicative of a user wearing, and/or body parts of the user wearing, the wearable device 100. In accordance with one embodiment, the accelerometer 105 within the wearable device 100 includes a 3-axis accelerometer that generates acceleration information with respect to the x-axis, the y-axis, and the z-axis of the accelerometer based on the acceleration experienced by the wearable device 100. Alternatively, the wearable device 100 can include three independent accelerometers (not shown for illustrative convenience) that each generate acceleration information with respect to a single axis, such as the x-axis, the y-axis, or the z-axis of the wearable device 100. Alternatively, the wearable device 100 can include an inertial measurement unit (IMU) that measures the velocity, the orientation, and the acceleration using a combination of one or more accelerometers, gyroscopes, and magnetometers. Thus, although generally referred to herein as an accelerometer 105, the accelerometer 105 can be any motion sensing element or combination of elements that provides acceleration information.

According to some embodiments, the accelerometer 105 includes a detection range of ±4 times the force of gravity (Gs). However, the range can vary, such as being ±10 Gs or ±2 Gs. Further, the accelerometer 105 can have a sampling rate of 50 hertz (Hz) such that each second the accelerometer 105 generates 150 points of acceleration information, or 50 points within each axis. However, the sampling rate can vary, such as being 20 Hz to 100 Hz.

According to some embodiments, one or more sensors of the wearable device 100, such as the accelerometer 105, can include a built-in temperature sensor, such as the temperature sensor 111 within the accelerometer 105. For example, the temperature sensor 111 within the accelerometer 105 can be used to calibrate the accelerometer 105 over a wide temperature range and to measure the temperature of the area of the body that the accelerometer 105 is coupled to. Other temperature sensors included with other device components can also be used. Other than the accelerometer 105, and temperature sensor 111, other subcomponents or elements of the wearable device 100 can include one or more microelectromechanical system (MEMS) components within the wearable device 100 that is designed to measure motion or orientation (e.g., angular-rate gyroscope, etc.). Alternatively, or in addition, the wearable device 100 can include a discrete temperature sensor, such as the temperature sensor 113 which can be positioned in a different location from the wearable device 100. The wearable device 100 can use the temperature information detected by the temperature sensor 111 and/or the temperature sensor 113 according to various methods and processes, as discussed in greater detail below. For purposes of convenience, reference is made below to the temperature sensor 111. However, such reference is not limited to apply only to the temperature sensor 111, but applies to any one or more temperature sensors within or connected to the wearable device 100.

The electrical contacts 115 are formed of conductive material (e.g., copper, silver, gold, aluminum, etc.) and provide an interface between the wearable device 100 and the skin 106a, or the sensor node 104 and the air gap between the sensor node 104 and the skin of the user, for receiving electrical signals (e.g., ECG, EMG, etc.) from the skin. The electrical contacts 115 can include one or more electrical contacts 115, such as two electrical contacts 115. With two electrical contacts 115, one contact can be electrically configured as a positive contact and the other contact can be electrically configured as a negative contact. However, in some aspects, there may be more than two electrical contacts, such as four electrical contacts 115 (e.g., two positive and two negative electrical contacts), six electrical contacts 115, etc.

In addition to the above-described components, the wearable device 100 can include one or more additional components without departing from the spirit and scope of the present disclosure. Such components can include a display (e.g., one or more light-emitting diodes (LEDs), liquid crystal display (LCD), organic light-emitting diode (OLED)), a speaker, a microphone, a vibration motor, a barometer, a light sensor, a photoelectric sensor, or any other sensor for sensing, measuring, or otherwise quantifying parameters and/or characteristics of the body. In other embodiments of the invention, the wearable device 100 can include components for performing one or more additional sensor modalities, such as, but not limited to, hydration level measurements, conductance measurements, and/or pressure measurements. For example, the wearable device 100 can be configured to, or include one or more components that, perform any combination of these different types of sensor measurements, in addition to the accelerometer 105 and temperature sensor 111.

Referring back to the temperature sensor 111, according to some embodiments, the primary purpose of the temperature sensor 111 is for calibrating the accelerometer 105. Accordingly, the temperature sensor 111 does not rely on direct contact to an object to detect the temperature. By way of example, the temperature sensor 111 does not require direct contact to the skin of a user when coupled to the user to determine the skin temperature. For example, the skin temperature affects the temperature information generated by the wearable device 100 without direct contact between the temperature sensor 111 and the skin. Accordingly, the temperature sensor 111 can be fully encapsulated and, therefore, be waterproof for greater durability. The thermal conductivity of the encapsulating material can be selected to control the ability of the temperature sensor 111 to detect the temperature without direct contact.

Temperature information generated by the temperature sensor 111 can be used by the wearable device 100 to determine an on-body status of the wearable device 100. Detection of the on-body status allows the wearable device 100 to automatically determine when the device is or is not coupled to a user. As will be discussed in greater detail below, functionality of the wearable device 100 (e.g., the computer program executed and/or components activated) can be selected or changed based on the detected on-body status.

The wearable device 100 can use the temperature information from the temperature sensor 111 based on the relationship that exists between the detected temperature information when the wearable device 100 is coupled to the body versus when the wearable device 100 is not coupled the body. More specifically, the wearable device 100 can use the difference between ambient air temperature and the skin temperature of the user to determine on body status.

When the wearable device 100 is coupled to the body, the measured temperature is primarily influenced by the skin temperature at the coupling location. In contrast, when the wearable device 100 is not coupled to the body, the measured temperature is primarily influenced by the ambient air temperature. That is, in general, when coupled to the body of the user, the heat generated by the user's body elevates the measured temperature to greater than the ambient air temperature. For most ambient air temperatures, the skin temperature at the coupling location is greater than the ambient air temperature. Thus, the wearable device 100 being off the body versus on the body is reflected in the changes of the temperature information generated by the temperature sensor 111.

The temperature information can be used to determine an on-body state of the wearable device 100. The temperature information can be raw temperature information (e.g., un-scaled) or normalized temperature information (e.g., scaled). Such normalization can include relating the raw temperature information to a specific temperature scale, such as Celsius, Fahrenheit, etc. Further, the temperature information detected by the temperature sensor 111 can include the temperature (raw or normalized), the change in temperature, and/or the rate of change in temperature. Depending on one or more of the temperature, the change in temperature, and the rate of change in temperature, the wearable device 100 can determine the on-body state by, for example, comparing the temperature, change in temperature, or rate of change in temperature to an ambient temperature value or a predefined value (e.g., from a lookup table or a decision tree).

By way of example, and without limitation, during a first state or period, the temperature sensor 111 within the wearable device 100 may generate a detected normalized temperature of 20° C. Subsequently, the wearable device 100 may generate a detected normalized temperature of 31° C. The normalized temperatures can be used to determine the on-body status of the wearable device 100. According to some embodiments, the temperature (e.g., 31° C.) alone indicates the on-body status of the wearable device 100. One or more specific temperature values (e.g., scaled or un-scaled) can be correlated to an on-body status, such as on the body or off of the body. Accordingly, when one of the specific temperature values is reached (or a temperature change is reached), the wearable device 100 determines on-body status accordingly. Alternatively, or in addition, one or more thresholds may be previously correlated to an on-body status. Accordingly, when one of the thresholds is met, the wearable device 100 determines its on-body status accordingly. By way of example, and without limitation, a threshold may be 24° C. such that a temperature above 24° C. correlates to the wearable device 100 being on the body.

According to some embodiments, the wearable device 100 can include machine learning to, for example, modify the thresholds based on repeated usage of the wearable device 100, such that the on-body status (and/or specific locations) determined by one sensing modality (e.g., accelerometer based location) can be used to update the thresholds or indicators for use with another sensing modality (e.g., temperature). Further, according to some embodiments, specific individuals have specific heat signatures or variations in temperature with respect to location of the wearable device 100. Thus, according to some embodiments, the wearable device 100 can use historical temperature information to determine the identity of the user wearing the wearable device 100, in addition to determining the on-body status. The determination as to the identity of the wearer of the wearable device 100 can also use information from one or more of the components of the wearable device 100.

According to some embodiments, the change in temperature (e.g., 20° C. to 31° C.) indicates the on-body status of the wearable device 100. The wearable device 100 can use the change in temperature to omit false on-body statuses that are based on, for example, elevated ambient temperatures. By way of example, depending on certain locations and/or activities, the ambient air temperature's effect on the temperature sensor 111 may give a false on-body status. Accordingly, the change in temperature can be used to determine the on-body status in which a lower temperature is used as an indicator of, for example, the ambient air temperature (e.g., the wearable device 100 not coupled to the body). A change in temperature from, for example, 20° C. to 31° C. can indicate that the wearable device 100 went from being off of the body (e.g., in an ambient air environment at 20° C.) to being on the body and now registering a temperature of 31° C. (e.g., body surface temperature).

Along with the temperature information, the temperature sensor 111, or another sensor or component within the wearable device 100 (e.g., processor 101, transceiver 107, etc.), can measure time or can generate information based on a set rate (e.g., 1 measurement every three seconds). The measured time can be correlated to the temperature information. Such correlation of the time to the temperature information can be used for determining the on-body state of the wearable device 100. For example, the rate of change in temperature (e.g., 20° C. to 31° C. over the course of, for example, 30 seconds) can indicate the on-body status of the wearable device 100. Whereas, for example, the rate of change in temperature (e.g., 20° C. to 31° C. over the course of, for example, 30 minutes) can indicate the wearable device 100 is left in the sun or a hot car and this information can combined with other sensor data, such as accelerometer data, to confirm a lack of movement. Using both the change in the temperature and the time during which the change occurred to obtain the rate can further eliminate false on-body statuses, such as eliminating the ambient air temperature changing over a period of time, which could possibly provide a false on-body status.

Figure 2:
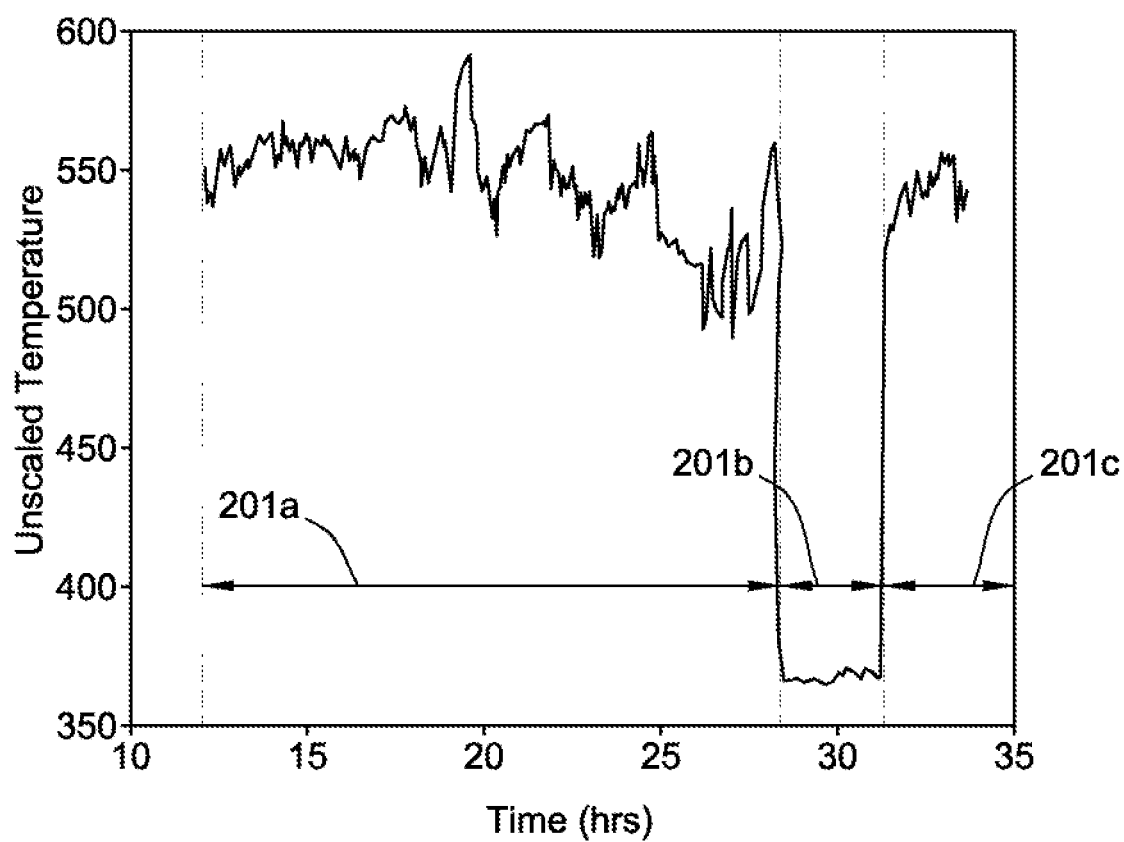
FIG. 2 illustrates a plot of temperature information detected by a wearable device versus time in accord with aspects of the present disclosure.

FIG. 2 illustrates a plot of un-scaled temperature information (y-axis) versus time (x-axis), in accord with some aspects of the present concepts. Specifically, FIG. 2 includes three time periods, time period 201a, time period 201b, and time period 201c. During time period 201a, the wearable device 100 is coupled to the body of a user. Accordingly, the un-scaled temperature information remains generally between 500 and 600. During time period 201b, the wearable device 100 is not coupled to the body. As shown in the plot, the un-scaled temperature lowers to between 350 to 400. During time period 201c, the wearable device 100 is coupled to the body. Accordingly, the un-scaled temperature information reverts back to between 500 to 600.

According to some embodiments, the un-scaled temperature measurement between 500 to 600 indicates an on-body state of the wearable device 100 being on the body. Further, the un-scaled temperature measurement between 350 to 400 indicates an on-body state of the wearable device 100 being off of the body.

According to some embodiments, if the wearable device 100 includes multiple temperature sensors, such as both the discrete temperature sensor 113 and the temperature sensor 111 of the accelerometer 105, information from the multiple temperature sensors can be combined to improve the accuracy of the temperature information. By way of example, an internal temperature sensor in an element of the wearable device 100 and/or a discrete temperature sensor can be used to determine a baseline temperature, such as to determine the ambient air temperature. A second internal temperature sensor in an element of the wearable device and/or a discrete temperature sensor can be used to determine the skin temperature if adjacent to the body of a user as compared to the first temperature sensor. For example, one temperature sensor may be located on the side of the wearable device 100 for determining the skin temperature, if coupled to the body. A second temperature sensor may be located on the opposite side of the wearable device 100. If both temperature sensors detect the same, or approximately the same, temperature, the temperature represents the ambient air temperature with the wearable device 100 not coupled to the body of a user. However, if the temperature sensor on the skin side of the wearable device 100 detects a higher temperature than the temperature sensor on the ambient air side of the wearable device, the difference in temperature indicates that the wearable device 100 is coupled to the skin of a user.

According to some embodiments, the change in the un-scaled temperature measurement from between 500 to 600 to between 350 and 400 indicates an on-body status of the wearable device 100 being off of the body (e.g., off-body state). Further, the change in the un-scaled temperature measurement from between 350 to 400 to between 500 to 600 indicates an on-body status of the wearable device 100 being on the body (e.g., on-body state).

According to some embodiments, the change in the un-scaled temperature measurement from between 500 to 600 to between 350 and 400 and over the course of a short period of time (e.g., several minutes or less) indicates an off-body state. Further, the change in the un-scaled temperature measurement from between 350 to 400 to between 500 to 600 and over the course of a short time period (e.g., several minutes or less) indicates an on-body state.

As shown in FIG. 2, the temperature detected by the temperature sensor 111 spikes to higher values in response to coupling the wearable device 100 to the skin of a user. When the wearable device 100 is removed from the skin of the user, the exact opposite phenomena occurs—the temperature sensor detects a sudden decrease in temperature. Further, as shown in FIG. 2, the sudden increase and decrease in temperature are different than the modulations in the temperature values while the wearable device 100 is coupled or is not coupled to the skin of the user. By way of example, and without limitation, such modulations can be caused by natural shifts in body temperature or by changes in the ambient air environment.

With the wearable device 100 having the ability to determine its on-body status based on temperature, the wearable device 100 can alter its functionality accordingly. Based on the temperature information indicating that the wearable device 100 is on the body (e.g., on-body state), the wearable device 100 can operate in, for example, a data collection mode with respect to the other elements and functionality of the wearable device 100. Based on the temperature information indicating that the wearable device 100 is off the body (e.g., off-body state), the wearable device 100 can operate in an idle mode or turn off. In some embodiments, a detection based on temperature that the wearable device 100 is not on the body can turn off all functionality of the wearable device except for the temperature sensor 111 to conserve resources (e.g., power). However, with the temperature sensor 111 still functioning, the wearable device 100 can transition out of idle or off mode based on the temperature information from the temperature sensor 111 indicating that the wearable device 100 is now on the body. Further, although primarily disclosed as either an on or data collection mode and an idle or off mode, any functionality of the wearable device 100 can be turned on or off, or put into an idle mode, based on the on-body state.

In addition to processing temperature information to detect the on-body status, the wearable device 100 also can process the temperature information to determine its location on the body. That is, body temperature varies relative to the distance from the body's core. At locations at or near the core, such as the torso, body temperature is the greatest. At locations distant from the core, such as the limbs, body temperature is the smallest. This relationship exists both internally and externally (e.g., skin temperature). Based on this relationship, the wearable device 100 can determine its location on the body based on differences in the magnitude of the detected temperature.

According to some embodiments, the location of the wearable device 100 on the body is determined based on a correlation between the temperature detected by the wearable device 100 off of the body and the temperature detected by the wearable device 100 on the body. The temperature detected by the wearable device 100 off of the body provides, for example, an indication of the ambient air temperature. With the ambient air temperature as a baseline, the temperature information detected by the wearable device 100 on the body can indicate the location of the wearable device.

Figure 3:
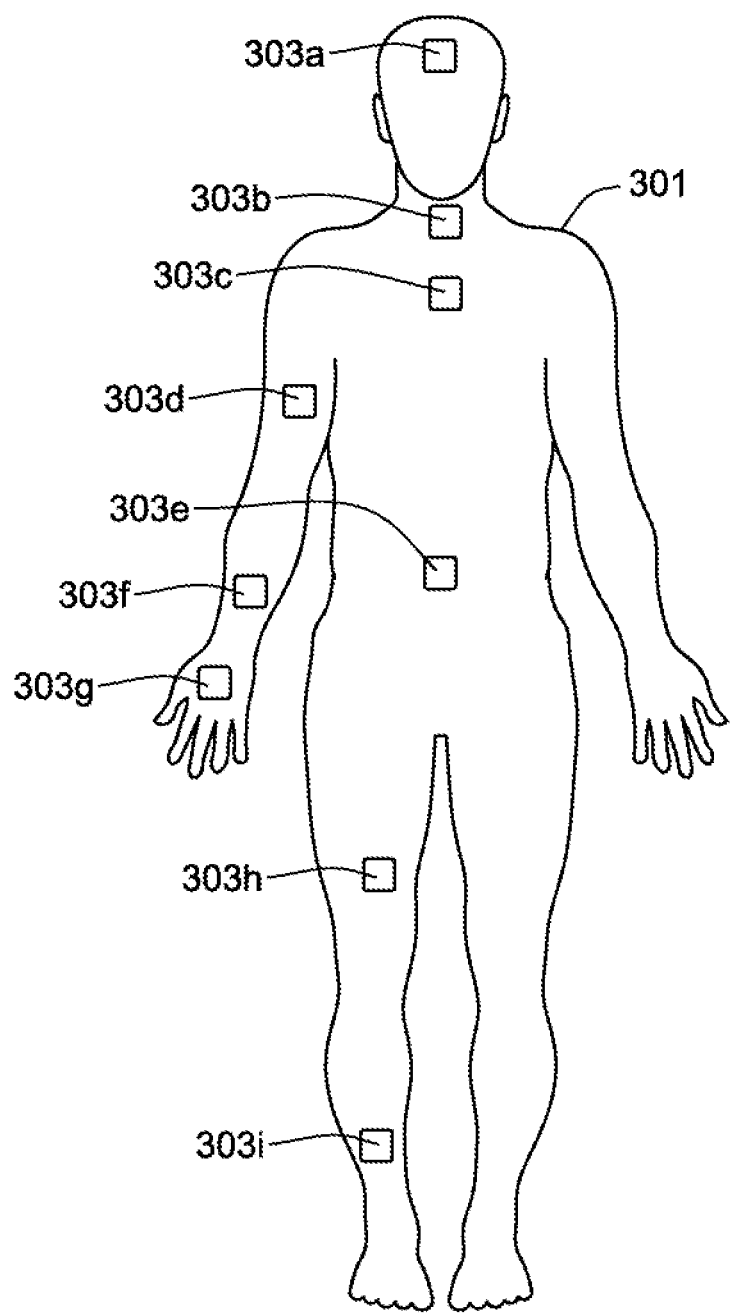
FIG. 3 illustrates exemplary locations of a wearable device on a user in accord with aspects of the present disclosure.

FIG. 3 illustrates various possible locations of the wearable device 100 on a user 301, in accord with some aspects of the present concepts. Specifically, FIG. 3 shows wearable devices 303a-303j (e.g., multiple wearable devices 100) located about the user 301. Wearable device 303a is located on the head (e.g., forehead) of user 301 and may be for monitoring various electrical characteristics of the brain. Wearable device 303b is located on the neck of the user 301 and may be for monitoring the user's heart rate. Wearable device 303c is located on the chest of the user 301 and may be for monitoring cardiac activity of the user 301. Wearable device 303d is located on the upper arm of the user 301 and may be for monitoring muscle activity of the biceps and/or triceps of the user 301. Wearable device 303e is located on the lower abdomen of the user 301 and may be for monitoring blood flow and/or posture of the user 301. Wearable device 303f is located on the lower arm of the user 301 and may be for monitoring the pulse of the user 301 during an activity, such as walking, running, swimming, etc. Wearable device 303g is located on the hand of the user 301 and may be for monitoring blood oxygen levels. Wearable device 303h is located on the upper leg of the user 301 and may be for monitoring muscle activity of the upper leg. Wearable device 303i is located on the lower leg of the user 301, such as at the ankle, and may be for monitoring foot strikes of the foot of the user 301. Wearable device 303j is located on the foot of the user 301 and may be for monitoring foot strikes of the user.

In view of the various possible locations of the wearable device 100 (e.g., wearable devices 303a-303j), the temperature information from the temperature sensor 111 may be used to determine the location of the wearable device 100 at one of the various locations. Table 1 lists exemplary temperature measurements of a wearable device 100 at some of the locations discussed in FIG. 3, in accord with some aspects of the present concepts.

TABLE 1

| Segment | 20° C. | 25° C. | 30° C. | 35° C. |
|---|---|---|---|---|
| Upper arms | 28 | 30.8 | 33.4 | 36.1 |
| Lower arms | 27.7 | 30.3 | 33.6 | 35.8 |
| Hands | 24 | 25.4 | 32.9 | 35.9 |
| Upper legs | 27.9 | 30.5 | 33.4 | 35.1 |
| Lower legs | 25.8 | 28.9 | 32.7 | 35.4 |
| Feet | 21.7 | 27.1 | 34.8 | 35.6 |
| Head/Neck | 32.9 | 33.9 | 34.8 | 35.9 |
| Trunk | 31.3 | 33 | 34.5 | 35.6 |

By way of example, and without limitation, the locations include the upper arms (e.g., wearable device 303d), the lower arms (e.g., wearable device 303f), the hands (e.g., wearable device 303g), the upper legs (e.g., wearable device 303h), the lower legs (e.g., wearable device 303i), the feet (e.g., wearable device 303j), the head or neck (e.g., wearable device 303a or 303b), and the trunk (e.g., wearable device 303e). The various ambient air temperatures are, for example, 20° C., 25° C., 30° C., and 35° C.

As shown in Table 1, segments of the body that are closer to the core are associated with higher temperature measurements. For example, the temperature at the trunk is about seven degrees higher than the temperature at the hands for an ambient air temperature of 20° C. Based on the differences in the temperature measurements at the various segments, temperature information from the temperature sensor 111 within the wearable device 100 allows the wearable device 100 to determine its location on the body (e.g., user 301).

At lower ambient temperatures, differences between temperature measurements at the various segments are more pronounced than at higher ambient temperatures. Given the average core body temperature of about 37° C., as the ambient air temperature approaches the core body temperature of 37° C., it is more difficult to distinguish between locations of the wearable device 100. Accordingly, according to some embodiments, the determination of the location of the wearable device 100 based solely on temperature may be limited to conditions in which the ambient air temperature is less than a threshold value. By way of example, and in view of the temperature measurements of Table 1, the threshold value can be 30° C. Once the location of the wearable device 100 is determined, functionality of the wearable device 100 can be configured accordingly, as is discussed in greater detail below.

The wearable device 100 can use data over a fixed time interval or a fixed number of samples to determine location of the device. Specifically, the wearable device 100 can select a set of one or more time and/or frequency domain features. Exemplary features with respect to the temperature information include, for example, mean, maximum, minimum, range, standard deviation, skewness, kurtosis, and power of the temperature signal within each time interval.

Baseline values of these features could be extracted from a training dataset of temperature values measured at various body locations during several characteristic activities completed in a range of ambient temperatures and across several subjects. Specifically, changes in some features above certain thresholds could be used to characterize state transitions (i.e., between on-body, off-body, and on-charger), and the location of the device after each state transition could be identified as the location that minimizes a normalized Euclidian distance measure characterizing the distance between the current sample and the baseline of each location in feature space. While this embodiment utilizes a k-means (or k-medians) approach for classifying device location, classification can occur using any of the modeling techniques listed herein.

Referring back to the accelerometer 105, acceleration information generated by the accelerometer 105 can be processed to determine the location of the wearable device 100 on the body of the user independent of, or in combination with, determination of the location based on the temperature information. According to some embodiments, the wearable device 100 (e.g., the processor 101) processes the acceleration information to extract features from the acceleration information. The acceleration information generated by the accelerometer 105 can be processed continuously, periodically, and/or on demand by the wearable device 100. The acceleration information can be collected over a predefined period of time or for a predefined number or set of data points. Specifically, the wearable device 100 extracts a set of one or more time and/or frequency domain features. Exemplary features with respect to the acceleration information include acceleration signal range, minimum acceleration value, maximum acceleration value, mean acceleration value, root mean square (RMS) acceleration value, signal entropy, line length, mean cross ratio, range ratio, dominant frequency, ratio of dominant frequency power to sum of power in the frequency spectrum, and spectral entropy. The specific features extracted from the acceleration information provide specific details or characteristic information about the acceleration experienced by the wearable device and user.

According to some embodiments, a feature can be based on the dominant frequency of the acceleration information and the energy of the dominant frequency. Alternatively, or in addition, a feature may be based on a range of frequencies and/or multiple dominant frequencies (e.g., top five dominate frequencies). Another feature can be based on the scale of the acceleration information, such as the difference between the largest acceleration and the smallest acceleration and/or opposite magnitude of acceleration. Another feature can be based on a range of the acceleration information, such as over the entire spectrum of acceleration information, or may be based on a subset of the entire spectrum, such as ±2 Gs where the entire spectrum of acceleration is generated across ±4 Gs. Another feature can be based on entropy of the acceleration information, such as whether the acceleration information is smooth or noisy. Another feature can be line length, which is based on the total amount of movement generated in the positive and the negative directions by integrating the rectified acceleration signal. Another feature can be the mean cross ratio, which is based on measuring how often the orientation of a body segment changes by taking the ratio of time spent above or below the mean over a fixed duration. Another feature can be range ratio, which is based on measuring the relative movement in orthogonal directions (e.g., X and Y) by taking the ratio of the range along each axis.

According to some embodiments, additional features can be used to determine the location of the wearable device 100, and these additional features may be independent of the generated acceleration information. For example, other physiological and/or biometric parameters that can be detected by the wearable device 100 and can be used to determine the location of the wearable device 100. Such physiological and/or biometric parameters can include heart rate, blood pressure, ECG signals, EMG signals, EEG signals, etc. With respect to, for example, heart rate, blood pressure, and/or ECG signals, a feature can be the ability to detect or not detect these parameters, or the strength of the signals indicating these parameters. Thus, although the present disclosure focuses primarily on acceleration information and temperature information, other physiological and/or biometric parameters generated by other components of the wearable device 100 can be used in conjunction with, or independent of, the acceleration information and/or the temperature information to determine the location of the wearable device 100 on a user.

According to the present concepts disclosed herein, wearable devices 303a-303j can be placed on the user 301 and can be automatically configured, as discussed in detail below, according to the specific location of the wearable devices 303a-303j independent from the user 301 or another user (e.g., clinician, technician, doctor, etc.) manually setting the location. The wearable devices 303a-303j can then process physiological information specific to that location based on location-specific metrics and/or by activating location-specific components, as discussed in detail below.

Figure 4:
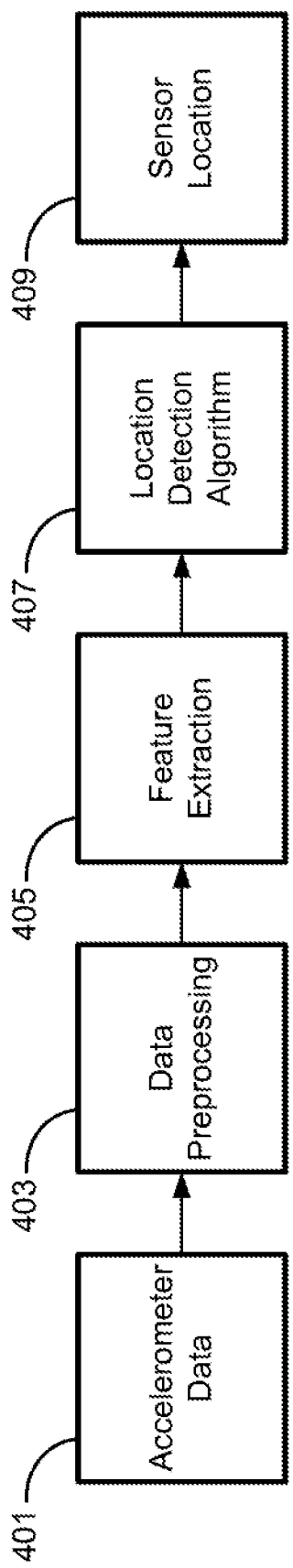
FIG. 4 illustrates a general flow diagram for determining a location of a wearable device on a user based on acceleration information in accord with aspects of the present disclosure.

FIG. 4 illustrates a general flow diagram for determining a location of a wearable device 100 on a user based on acceleration information in accord with concepts of the present disclosure. Prior to step 401, the wearable device 100 is placed on the user. The wearable device 100 may be directly affixed to the user, such as being directly affixed to the user's skin, e.g., by an adhesive, a strap or as part of a garment. According to some embodiments, the wearable device 100 can automatically determine when it is coupled to the body of a user based on processing temperature information generated by the temperature sensor 111 (or any other temperature sensor of the device), as discussed above.

At step 401, acceleration information/data is generated by the wearable device 100, such as by the accelerometer 105. The acceleration information can be considered raw acceleration information or data (e.g., data received directly from the accelerometer 105). As discussed above, such information may be generated by a system or device that includes the capability of generating 3-axis acceleration information with respect to the x-axis, the y-axis, and the z-axis.

At step 403, the wearable device 100 pre-processes the raw acceleration information or data. The pre-processing can include any signal conditioning and/or processing to prepare the acceleration information for feature extraction. Such signal conditioning can include filtering the acceleration information to remove noise and/or other artifacts, amplifying the acceleration information to increase the resolution of the input signal and/or to reduce noise, and normalization. The pre-processing can optionally further include removing the effects of gravity on the acceleration information.

By way of example, at step 403, the raw acceleration information can be first pre-processed by applying a low-pass filter with a cutoff of 12 Hz to remove high frequency noise. After applying the low-pass filter, resultant acceleration vectors about the x/y-axes, y/z-axes, z/x-axes, and the x/y/z-axes are derived according to common vector derivation techniques. In addition, or in the alternative, the acceleration information may be subject to additional and/or alternative pre-processing than the pre-processing disclosed above without departing from the spirit and scope of the present disclosure.

After pre-processing, features can be extracted from the pre-processed acceleration information at step 405. As discussed above, the features characterize the acceleration information, such as in terms of frequency, energy, and entropy. As discussed above, the types of the extracted features include acceleration signal range, minimum acceleration value, maximum acceleration value, mean acceleration value, root mean square (RMS) value, signal entropy, line length, mean cross rate, and range ration, etc.

In accordance with some embodiments of the invention, the features can be extracted in groups, also referred to as feature sets, according to, for example, time and frequency domain features such that multiple features can be used to characterize the same acceleration information. For example, as many as 36 or more features can be used to determine the location of the wearable device 100 within a single feature set. However, the number of features used to determine the location from the acceleration information within a feature set can range from one to greater than 36 and in some embodiments, 20 to 30 features for each feature set can be used. According to a feature set being extracted as a set of time domain features, acceleration information may be collected over a period of time T (or number of data points), and a feature set can be used characterize the acceleration information over the period of time T (or number of data points). By way of example, T can be three seconds such that the acceleration information represents the acceleration experienced by the accelerometer 105 and, therefore, the wearable device 100 over the three seconds. Where the acceleration information is generated at a rate of 50 hertz (Hz), as an example, a feature set can be extracted from some or all of the 150 data points for each one of the three axes. Thus, the feature set characterizes 450 data points of acceleration information. However, the value of T can be less or greater than three seconds without departing from the spirit and scope of the disclosure, such as one second, two second, five seconds, etc. And the value of T can be the same for all features, or the value of T can change over time, for example, to evaluate higher or lower activity levels or adjustable signal generation rates. Thus, for higher signal rates (e.g., to better evaluate higher activity rates) T can be increased or decreased.

According to one embodiment, feature sets can be determined based on non-overlapping periods of time T. Alternatively, feature sets may be determined based on overlapping periods of time T. For example, a feature set may be determined for a three second period, and a subsequent period may overlap with the period with respect to the acceleration information the period applies to. The overlap may be, for example, 50 percent such that a feature set covering a three second period overlaps with a previous or subsequent period by 1.5 seconds.

At step 407, the feature set is processed to determine the location of the wearable device 100. The processing performed to determine the location based on the feature set may vary, such as being based on a decision tree, nearest neighbor and Bayesian Networks, support vector machines, neural networks, Gaussian Mixture Models (GMM), and Markov chains. According to one embodiment, the feature set can be processed according to a decision tree analysis. By way of example, the decision tree can be a J48 decision tree or a C4.5 decision tree. The decision tree includes nodes and leaves. At each node, the decision tree branches based on the value of a single feature according to a threshold mechanism. By way of example, if a node represents a dominant frequency value, the decision tree may include two branches extending from the node. One branch may represent a dominant frequency of greater than a threshold value, and the other branch may represent a dominant frequency of less than or equal to the threshold value. Thus, depending on the value of the dominant frequency of the feature from the acceleration information, one or the other branch is selected or followed along the decision tree.

At the outcome of the decision tree is the location of the wearable device 100. The furthest branches on the tree represent the possible end results or locations of the wearable device 100 on the body. Thus, at step 409, at the end of processing the feature set according to the decision tree, a location of the wearable device 100 is determined.

Figure 5:
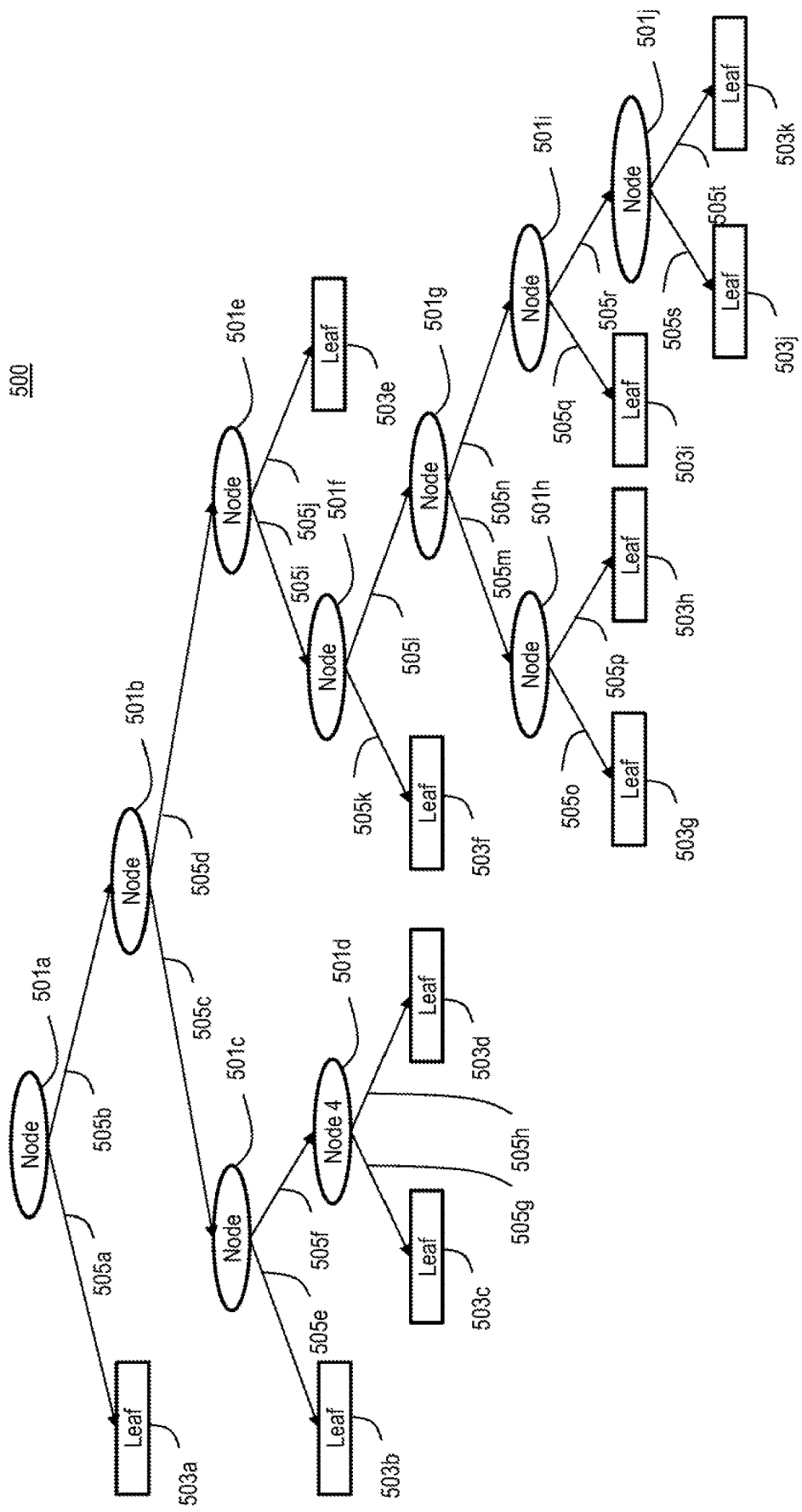
FIG. 5 illustrates an exemplary decision tree related to acceleration information in accord with aspects of the present disclosure.

FIG. 5 shows an exemplary decision tree 500, according to one embodiment. The decision tree 500 includes nodes 501a-501j and leaves 503a-503k, in which a node represents an analysis with respect to a feature, and the leaves branching from the node represent the outcomes of the analysis. By way of example, at node 501a, a determination is made with respect to the entropy of the acceleration information with respect to the y/z-axes. If the entropy is less than or equal to a threshold, branch 505a is selected and the outcome of the location of the wearable device 100 is leaf 503a, which may represent the chest of the user. If the entropy is greater than the threshold, branch 505b is selected and the decision tree 500 proceeds to node 501b.

At node 501b, the analysis may be with respect to the line length along the z/x-axes. If the line length is less than or equal to a threshold, branch 505c is selected and the decision tree 500 proceeds to node 501c. If the line length is greater than the threshold, branch 505d is selected and the decision tree proceeds to node 501e.

At node 501c, the analysis may again be with respect to the line length along the z/x-axes. If the line length is less than or equal to another threshold, different than the previous threshold, branch 505e is selected and the outcome of the location of the wearable device 100 is leaf 503b, which may represent the wrist. If the line length is greater than the additional line length threshold, branch 505f is selected and the decision tree proceeds to node 501d.

At node 501d, the analysis may be with respect to the minimum acceleration along the x/y-axes. If the minimum acceleration is less than or equal to a threshold, branch 505g is selected and the outcome of the location of the wearable device 100 is leaf 503c, which may represent the ankle. If the minimum acceleration is greater than the threshold, branch 505h is selected and the outcome of the location of the wearable device 100 is leaf 503d, which may represent the wrist.

Adverting to node 501e, at node 501e, the analysis may be with respect to the mean acceleration along the y/z-axes. If the mean acceleration is less than or equal to a threshold, branch 505i is selected and the decision tree proceeds to node 501f. If the mean acceleration is greater than the threshold, branch 505j is selected and the outcome of the location of the wearable device 100 is leaf 503e, which may represent the wrist.

At node 501f, the analysis may be with respect to the entropy along the z/x-axes. If the entropy is less than or equal to a threshold, branch 505k is selected the outcome of the location of the wearable device 100 is leaf 503f, which may represent the wrist. If the entropy is greater than the threshold, branch 505l is selected and the decision tree proceeds to node 501g.

At node 501g, the analysis may be with respect to the line length along the y/z-axes. If the line length is less than or equal to a threshold, branch 505m is selected and the decision tree proceeds to node 501h. If the line length is greater than the threshold, branch 505n is selected and the decision tree proceeds to node 501i.

At node 501h, the analysis may be with respect to the mean cross rate along the z/x-axes. If the mean cross rate is less than or equal to a threshold, branch 505o is selected and the outcome of the location of the wearable device 100 is leaf 503g, which may represent the wrist. If the mean cross rate is greater than a threshold, branch 505p is selected and the outcome of the location of the wearable device 100 is leaf 503h, which may represent the ankle.

Back at node 501i, the analysis may be with respect to the minimum acceleration along the x/y-axes. If the minimum acceleration is less than or equal to a threshold, branch 505q is selected and the outcome of the location of the wearable device 100 is leaf 503i, which may represent the ankle. If the minimum acceleration is greater than the threshold, branch 505r is selected and the decision tree proceeds to node 501j.

At node 501j, the analysis may be with respect to the mean acceleration along the z/x-axes. If the mean acceleration is less than or equal to a threshold, branch 505s is selected and the outcome of the location of the wearable device 100 is leaf 503j, which may represent the wrist. If the mean acceleration is greater than the threshold, branch 505t is selected and the outcome of the location of the wearable device 100 is leaf 503k, which may represent the ankle.

According to the foregoing example, processing the features according to the decision tree 500 yields the location of the wearable device 100 based on one or more decisions with respect to the features. Depending on the features used and the values of the features, one or more decisions are used to determine (or arrive to) the location. Although each decision discussed and illustrated with respect to FIG. 5 includes only two branches, each decision can include multiple branches and can be based on multiple ranges with respect to a feature.

The decision tree 500 illustrated in FIG. 5 can be generated based on previously collected acceleration information for various locations of the wearable device 100 on a user or a group of users. The collected acceleration information is then processed according to the techniques discussed above, including extracting feature sets from the data, and applying machine learning to determine which feature sets from the acceleration information apply to which locations of the wearable device 100 on the user. Accordingly, the decision tree 500 can be trained based on the predefined locations and previously generated acceleration information, also referred to as priori knowledge, processed according to the above-described approach.

Although discussed primarily with respect to acceleration information, according to some embodiments the decision tree 500 can be based also on temperature information or a combination of temperature and acceleration information. One or more of the initial decisions of the decision tree can be based on the temperature information. By way of example, initial decisions can be based on whether the temperature information indicates that the wearable device 100 is close to the core or remote from the core of the body. Additionally, one or more of the decisions can build on this information. Thus, if the temperature information indicates that the wearable device 100 is remote from the core (e.g., on an arm or leg), the accelerometer 105 can confirm this by determining whether low frequency acceleration signals (e.g., such as those associated with chest motion for respiration) are not present. Where respiration is detected, the device can determine (e.g., learn) that the user's core temperature is possibly lower than average.

Figure 6:
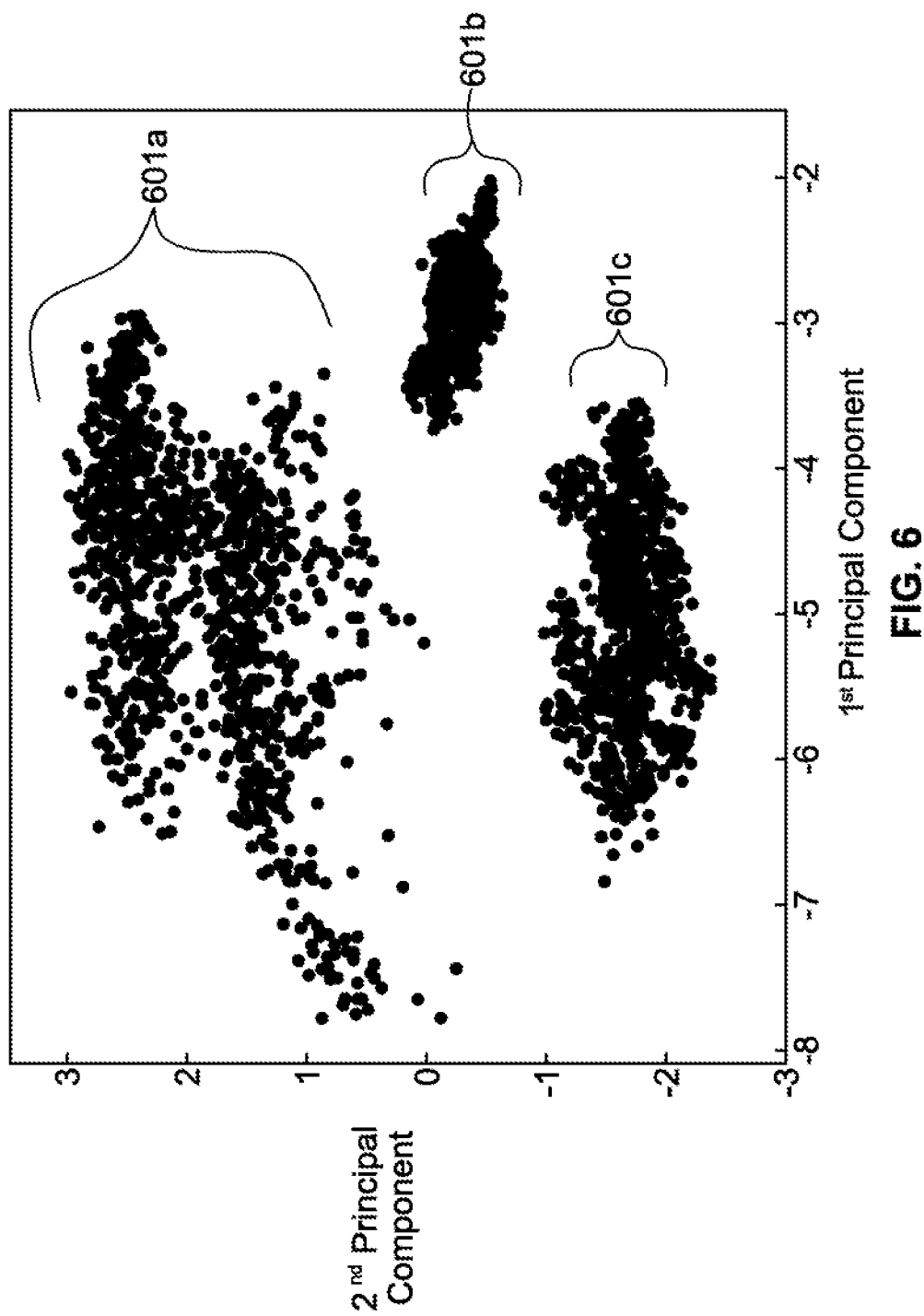
FIG. 6 illustrates an exemplary principal component analysis plot related to acceleration information in accord with aspects of the present disclosure.

FIG. 6 illustrates an exemplary principal component analysis plot that visually represents the distinction in feature sets that allows for determining the location of a wearable device 100. As shown, the x-axis can represent a first principal component and the y-axis can represent a second principal component. The plot shown in FIG. 6 represents a projection of the feature space extracted from the acceleration information according to a principal component analysis. That is, the points within groups 601a-601c represent acceleration information acquired from, for example, the accelerometer 105 within the wearable device 100 transformed into 2 dimensions according to two principal components. Each one of the principal components is a linear combination of a set of features, with the features for each principal component selected to maximize the variance of the captured acceleration information.

As discussed above, features are extracted from the acceleration information. As shown in the exemplary illustrated embodiment, the features are then transformed into one of the first principal component or the second principal component. According to the transformation, the acceleration information fits within one of the three groups 601a-601c. Based on the previously determined relationships between the first and second principal components, and the relationship of the principal components to various locations of the wearable device 100 on the user, the groups 601a-601c represent three different locations of a wearable device 100 on a user.

By way of example, group 601a can represent acceleration information acquired from a wearable device 100 located on the wrist that was transformed into the first and second principal components. Further, group 601b can represent acceleration information acquired from a wearable device 100 located on the chest that was transformed into the first and second principal components. Group 601c can represent acceleration information acquired from a wearable device 100 located on the ankle that was transformed into the first and second principal components. According to the foregoing, and as a visual representation of the approach for determining a location of a wearable device 100 based on acceleration information, subsequent data points within one of the three groups 601a-601c resulting from transforming the acceleration information into the first and second principal components indicate the location of the wearable device 100 on the user.

As discussed above, according to some embodiments, acceleration information generated by the accelerometer 105 and temperature information generated by the temperature sensor 111 or temperature sensor 113 can be used in combination to determine the on-body status, the location of the wearable device 100 on the user, or both.

A temperature-based approach at determining an on-body status, or an acceleration-based approach at determining an on-body status, may generate false indications. By way of example, a wearable device 100 left in direct sunlight may reach elevated temperatures similar to skin temperatures on the body 301. Alternatively, a wearable device 100 connected to a power source to recharge may generate heat from the process of recharging. Thus, the elevated temperatures during these conditions may result in false indications of the wearable device 100 being on the body.

Similarly, a wearable device 100 may be on a user's person but not coupled to the user's body. For example, the wearable device 100 may be in a pocket or in a container that the user is carrying. Although the wearable device 100 is not coupled to the skin of the user, the wearable device 100 may still experience acceleration measured by the accelerometer 105 that mimics acceleration experienced while coupled to the user. Thus, the acceleration may generate a false indication of the wearable device 100 being on the body.

To reduce and/or eliminate the false indications of on-body states, the wearable device 100 can use the temperature information and the acceleration information in combination.

Figure 7:
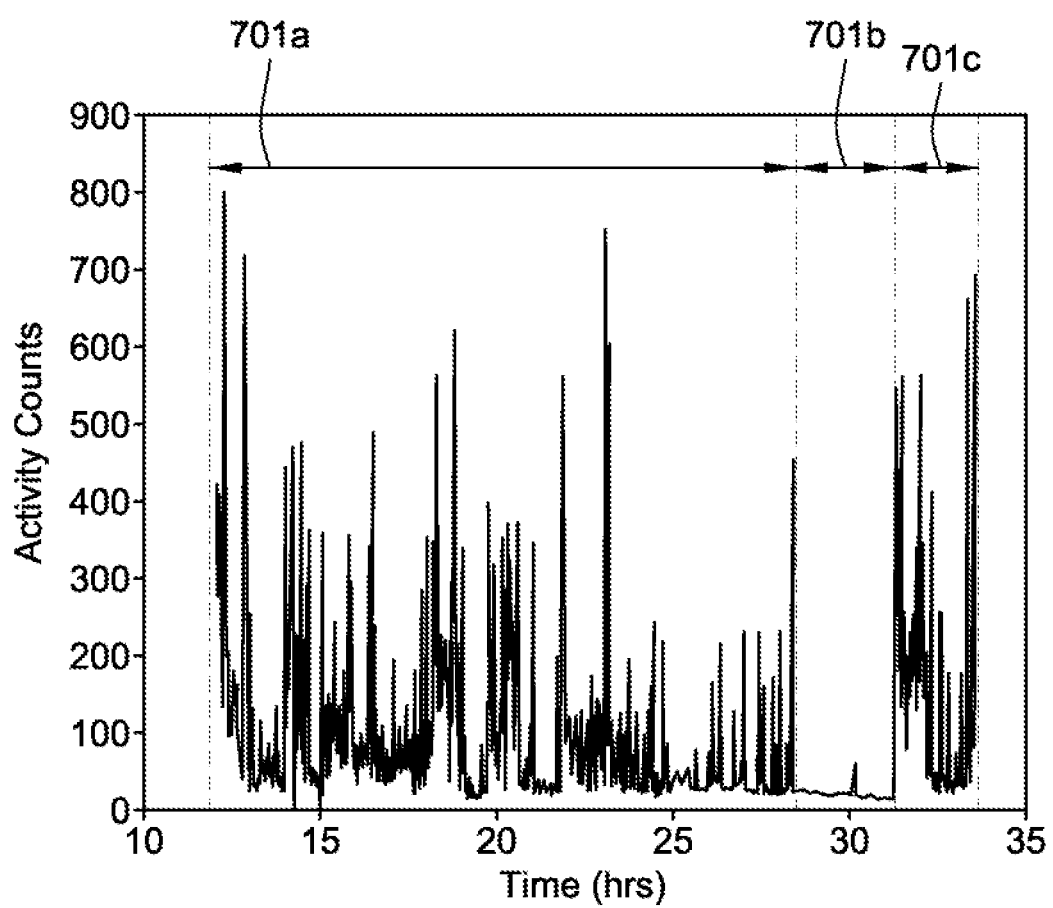
FIG. 7 illustrates an overall process flow for determining location-specific metrics to activate on a wearable device based on acceleration information in accord with aspects of the present disclosure.

FIG. 7 shows acceleration information generated by the accelerometer 105 during the same periods of time during which the temperature information was generated that is illustrated in FIG. 2, in accord with some aspects of the present concepts. More specifically, FIG. 7 is a plot of activity counts (y-axis) versus time (x-axis). FIG. 7 includes three time periods, time period 701a, time period 701b, and time period 701c. Time periods 701a, 701b, and 701c correspond to the time periods 201a, 201b, and 201c, respectively, in FIG. 2.

During time periods 701a and 701c, the wearable device 100 experienced acceleration, as shown by the activity counts. The activity counts are a proxy for the changes in acceleration measured by the accelerometer 105 during the various periods of time. Thus, if the activity counts are high, the wearable device 100 experienced large changes in acceleration. If the activity counts are low, the wearable device 100 experienced small changes in acceleration or no acceleration at all (e.g., stationary). During time period 701b, the wearable device 100 experienced little or no acceleration. Thus, the acceleration experienced by the wearable device 100 during time periods 701a and 701c agrees with the temperature information of FIG. 2 for time periods 201a and 201c indicating that the wearable device 100 is coupled to the user. Further, the lack of acceleration experienced by the wearable device 100 during time period 701b agrees with the temperature information of FIG. 2 for time period 201b indicating that the wearable device 100 is not coupled to the user.

Based on the comparison of FIGS. 2 and 7, temperature information and acceleration information can be used to discriminate states of the on-body status. By way of example, and without limitation, if instead of the information in FIGS. 2 and 7, time period 701b included acceleration information indicating that the wearable device 100 was moving, but time period 201b still indicated that the wearable device 100 was not coupled to the user based on the temperature information, the wearable device 100 can determine that it is not coupled to the user. Such a determination may not be possible based on the acceleration information alone. Similarly, if time period 201b included temperature information that indicated that the wearable device 100 was coupled to the user, but time period 701b indicated that the wearable device 100 did not experience acceleration, the wearable device 100 can determine that it is not coupled to the user. Such a determination may not be possible based on the temperature information alone.

Accordingly, the wearable device 100 can process both temperature information and acceleration information to determine its on-body status. The wearable device 100 can use other information, in addition to acceleration information and temperature information, generated by one or more components of the wearable device 100 to determine and/or verify the on-body status. By way of example, and without limitation, a voltage measurement of the power source 109 can distinguish different states by indicating that the wearable device 100 is connected to a charger. Thus, for example, if the process of recharging raises the temperature of the temperature sensor 111, the voltage measurement of the power source 109 can be used to distinguish between an on-body state despite certain temperature information. That is, if the voltage of the power source 109 is increasing, the wearable device 100 is on a charger, and if the voltage of the power source 109 is not increasing, the wearable device 100 is not on a charger.

As discussed above, where differences between skin temperature and ambient air temperature can differentiate the on-body status of the wearable device 100 (e.g., on-body versus off-body), differences in skin temperature between body segments can also be used to determine the on-body location. Thus, provided sufficient disparity between ambient air temperature and skin temperature, temperature information alone can indicate the location of the wearable device 100. However, as the ambient air temperature increases (e.g., as shown in Table 1 above), the disparity of temperature differences between body segments decreases. The decrease can lead to an inability to determine the location of the wearable device 100 based on the temperature information alone.

Thus, the temperature information and the acceleration information can be used together to determine the location of the wearable device 100. According to some embodiments, the temperature information can be processed to determine a general location of the wearable device 100, such as located on an extremity or located on the core of the body. With the general location as a starting point, the acceleration information can then be used to determine the more specific location. Accordingly, based on the decision trees discussed above, the one or more decisions can be based initially on processing the temperature information, such as by determining a general location. Once a general location of the wearable device 100 is determined, the acceleration information can be processed according to a decision tree analysis, where the starting point of the decision tree analysis with respect to the acceleration information is based on the general location determined from the temperature information. Although discussed as providing a general location for a starting point of the acceleration information analysis with respect to the location, the temperature information can be used according to other methods with respect a decision tree analysis, such as one or more determination at nodes within the decision tree.

Alternatively, the temperature information can be processed to determine a specific location of the wearable device 100 on the user, such as based on, for example, an absolute temperature relative to the ambient air temperature based on a change in the temperature, or an absolute temperature relative to the rate in the change in temperature. The wearable device 100 can then verify the location determined from the temperature information based on the acceleration information.

Figure 8:
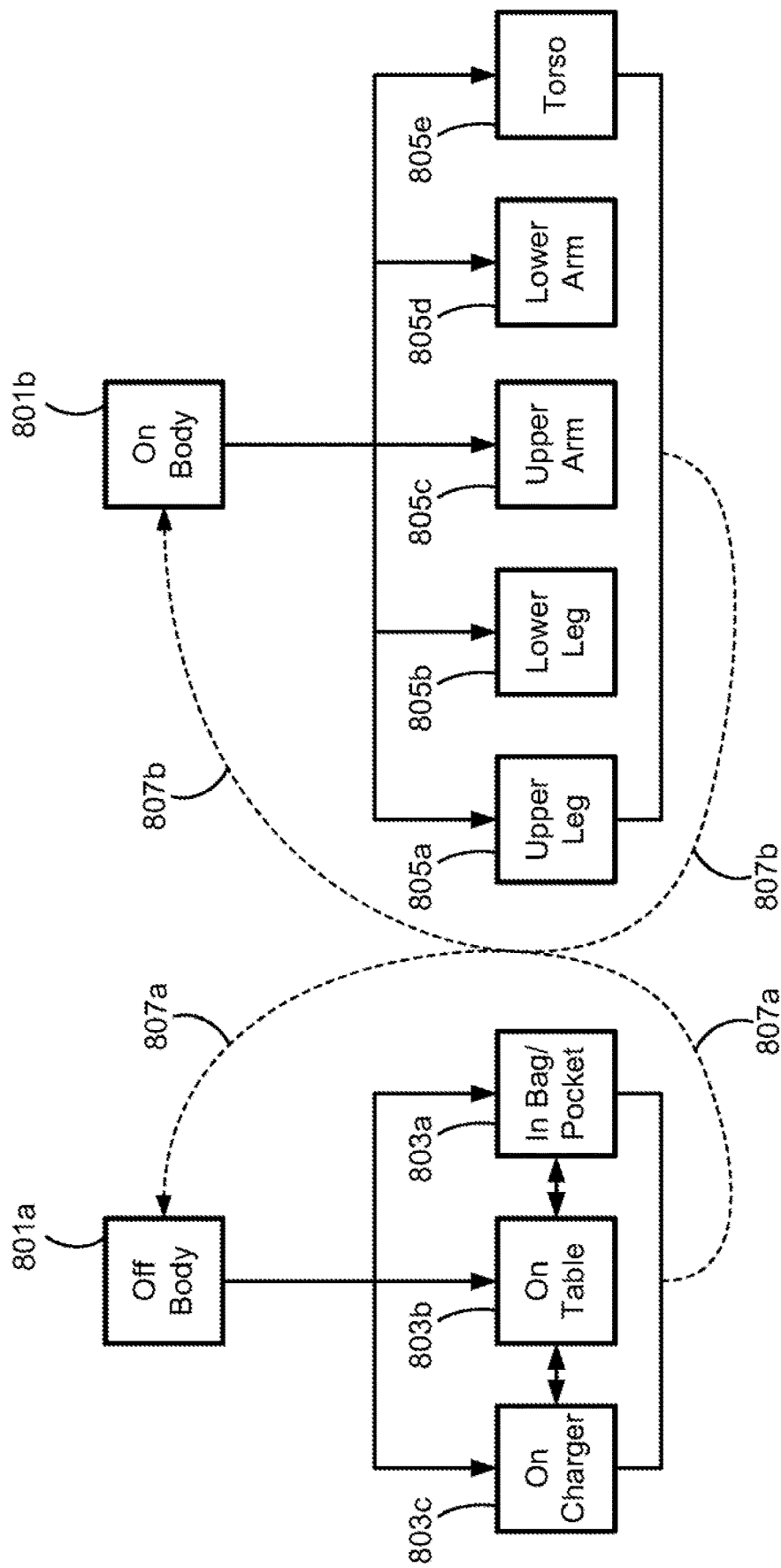
FIG. 8 illustrates a plot of acceleration information detected by a wearable device versus time in accord with aspects of the present disclosure.

FIG. 8 is a state diagram of the different on-body states and locations of a wearable device 100, and identification of transitions between the states based on acceleration information and temperature information, in accord with aspects of the present concepts. As shown, wearable device 100 can be in one of two distinct states with respect to the on-body status, either in an off-body state 801a (e.g., not coupled to the body of a user) or in an on-body state 801b (e.g., coupled to the body of a user). Upon determining the on-body status, the status of the wearable device 100 can then be decomposed further into distinct locations and/or states.

Referring to FIG. 8, the on-body status is determined initially based on one or both of acceleration information and temperature information, and can also be based on additional information generated by components of the wearable device 100, such as the voltage of the power source 109. By way of example, and without limitation, the wearable device 100 can determine the on-body status (e.g., off-body state 801a or on-body state 801) based on the acceleration information, the temperature information, or a combination of the temperature information and the acceleration information. According to some embodiments, the on-body status can also be based on one or more additional indications by components of the wearable device 100, such as the change in the charge of the power source 109 indicating the wearable device 100 is in an off-body state 801a. Upon determining the on-body status of the wearable device 100, the wearable device 100 can subsequently determine its location and/or state depending on its on-body status.

The functionality of the wearable device 100 can change according to the on-body status. According to some embodiments, with the wearable device 100 not coupled to the body (e.g., off-body state 801a), the functionality of the wearable device 100 providing measurements and/or analysis of physiological information of the user can turn off or be put into a lower power or sleep mode. Alternatively, the wearable device 100 can turn off completely. Turning the wearable device 100 off or going into a sleep mode extends the battery life for when the wearable device 100 is coupled to the user. Further, according to some embodiments, the wearable device 100 can automatically turn algorithms off when the wearable device 100 is not coupled to the body. Further, the wearable device 100 can turn off one or more components. For example, the step counter does not need to be running when the wearable device 100 is not coupled to the user and not able to counts the user's steps. Further, a sleep tracker does not need to be running if the wearable device is not coupled to a user and not able to track the user's sleep.

According to some embodiments, the wearable device 100 may be in the off-body state 801a when it should be in the on-body state 801b. In such a condition, according to some embodiments, the wearable device 100 can prompt the user to couple the wearable device 100 to the user's body. The prompt can originate from the wearable device 100 itself or from another device (e.g., from a device in communication with the wearable device 100). By way of example, and without limitation, the wearable device 100 can provide an audio, visual, and/or tactile prompt to remind the user to don the wearable device 100. Alternatively, the wearable device 100 can prompt an application running on, for example, a smart device (e.g., smart phone, laptop, etc.) in communication with the wearable device 100 to remind the user to apply the wearable device 100 or to select device features to use (e.g., running coach for a device mounted on the ankle, or posture coach for a device located on the torso). Such a condition can be determined, for example, based on differences in the on-body status as determined based on the acceleration information and the temperature information. For example, if the temperature information indicates that the wearable device 100 is not coupled to the user, but the acceleration information indicates that the wearable device 100 is experiencing acceleration (e.g., not stationary), the wearable device 100 can prompt the user to apply the wearable device 100 to the body.

Similarly, the wearable device 100 may be in the on-body state 801b when it should be in the off-body state 801a. In such a condition, according to some embodiments, the wearable device 100 can prompt the user to uncouple the wearable device 100 from the user's body. For example, the wearable device 100 can prompt a smart phone application in communication with the wearable device 100 to remind the user to remove the wearable device 100. Similar to above, such a condition can be determined, for example, based on differences in the on-body status as determined based on the acceleration information and the temperature information. For example, if the temperature information indicates that the wearable device 100 is coupled to the user, but the acceleration information indicates that the wearable device 100 is not experiencing acceleration (e.g., stationary), the wearable device 100 can cause a prompt for the user to remove the wearable device 100 from the body. The wearable device 100 can also prompt the user to place the wearable device 100 in the charger, such as to recharge the wearable device 100 when not coupled to the user.

When the wearable device 100 determines a change in the on-body status, such as a change from the off-body state 801a to the on-body state 801b, the wearable device 100 can automatically change its operation state from idle (e.g., no sensing and/or data logging) to a sensing state. The ability to automatically change general operation states from idle to not idle, as an example, improves battery performance.

With respect to the off-body state 801a, the wearable device 100 can determine whether it is at a first location 803a on the person (e.g., in a pocket, bag, purse, etc.), although not coupled to the body, at a second location 803b not on the person (e.g., stationary on a table, nightstand, etc.), or at a third location 803c on a charger. By way of example, and without limitation, the first location 803a on the person can be detected based on temperature information indicating that the wearable device 100 is not coupled to the body and acceleration information indicating that the wearable device 100 is moving. According to some embodiments, the acceleration information can further indicate that the movement corresponds to the wearable device 100 being in a bag carried by a user, in the user's pocket, etc. based on one or more extracted features from the acceleration information. The second location 803b can be detected based on temperature information indicating that the wearable device 100 is not coupled to the body and the acceleration information indicating that the wearable device 100 is not moving. The third location 803c can be detected based on the temperature information indicating that the wearable device 100 is not coupled to the body, the acceleration information indicating that the wearable device 100 is not moving, and information from the power source 109 indicating that the wearable device 100 is on the charger. However, according to some embodiments, the third location 803c can be detected based solely on the power source 109 indicating that the wearable device is on the charger.

Referring back to the on-body state 801b, the wearable device 100 can subsequently determine its location on the body of the user after determining that it is within the on-body state 801b. Exemplary locations in FIG. 8 include the upper leg 805a, the lower leg 805b, the upper arm 805c, the lower arm 805d, and the torso 805e. However, additional locations can be determined, such as any one or more of the locations shown in FIG. 3, in addition to other locations. The locations can be determined based solely on acceleration information, as described above with respect to FIGS. 4-6 and the corresponding portions of the specification. Alternatively, the locations can be determined based solely on temperature information as described above. For example, depending on the disparity between body segment temperatures and the ambient air temperature, the determination of the location of the wearable device 100 can be based solely on temperature information. Alternatively, the locations can be determined based on a combination of acceleration information and temperature information.

Upon determining the on-body state 801b and the activity and/or state of the wearable device 100, the wearable device 100 can adjust its functionality according to the determined location. According to some embodiments, the wearable device 100 can automatically toggle specific algorithms ON or OFF depending on the determined location of the device. According to some embodiments, the wearable device 100 can automatically tune algorithm parameters to different body coupling locations. The tuning can improve the accuracy of the algorithm output. According to some embodiments, the wearable device 100 can automatically adjust of a list of device features within, for example, a mobile application running on a mobile device in communication with the wearable device 100 based on the location. For example, if the wearable device 100 is located on the torso, a list of device features can be adjusted to include a posture coach. However, if the wearable device 100 is located at the ankle, the posture coach would not be included in the list. Instead, for example, a running coach can be included in the list of device features.

According to some embodiments, the wearable device 100 can automatically adjust the user experience associated with using the wearable device 100. For example, the wearable device 100 can interface with a mobile application running on a mobile device in communication with the wearable device 100 to change the steps that the user needs to go through, including calibration, etc., and provide pictures of the location of the wearable device 100 on the body based on the determined location of the wearable device 100. For example, if the wearable device 100 is located at the ankle, then the wearable device 100 will not run a posture algorithm and, therefore, the user will not be prompted to calibrate the wearable device 100 by the mobile application for the posture coach. By way of a further example, pictures within the mobile application could also then feature the wearable device 100 located at the ankle.

As indicated by arrows 807a and 807b in FIG. 8, the wearable device 100 monitors the acceleration information and/or the temperature information to determine changes in the on-body status and/or location and/or state of the wearable device 100. The wearable device 100 can continuously, periodically, or on-demand monitor the temperature information and the acceleration information.

By way of example, and without limitation, according to monitoring the temperature information from the temperature sensor 111, the wearable device 100 can determine a change in the on-body status, the activity and/or the location, or a combination thereof of the wearable device 100. The wearable device 100 can monitor the temperature, the change in temperature, and/or the rate of change in temperature. Based on the temperature information, the location and/or state of the wearable device 100 can change to another location and/or state, and/or the on-body status of the wearable device 100 can change to a different status within the state diagram of FIG. 8.

Similarly, by way of example, and without limitation, according to monitoring the acceleration information from the accelerometer 105, the wearable device 100 can determine a change in the on-body status, the activity and/or the location, or a combination thereof of the wearable device

100. Such a change can include another location and/or state, a different on-body status, or a combination thereof of the wearable device 100 within the state diagram of FIG. 8. Additionally, the monitoring can be any combination of the acceleration information and the temperature information. Upon determining the change in the on-body status, location and/or state, or a combination thereof, the wearable device 100 can again change its functionality and/or mode based on the new on-body status, location and/or state, or a combination thereof.

Figure 9:
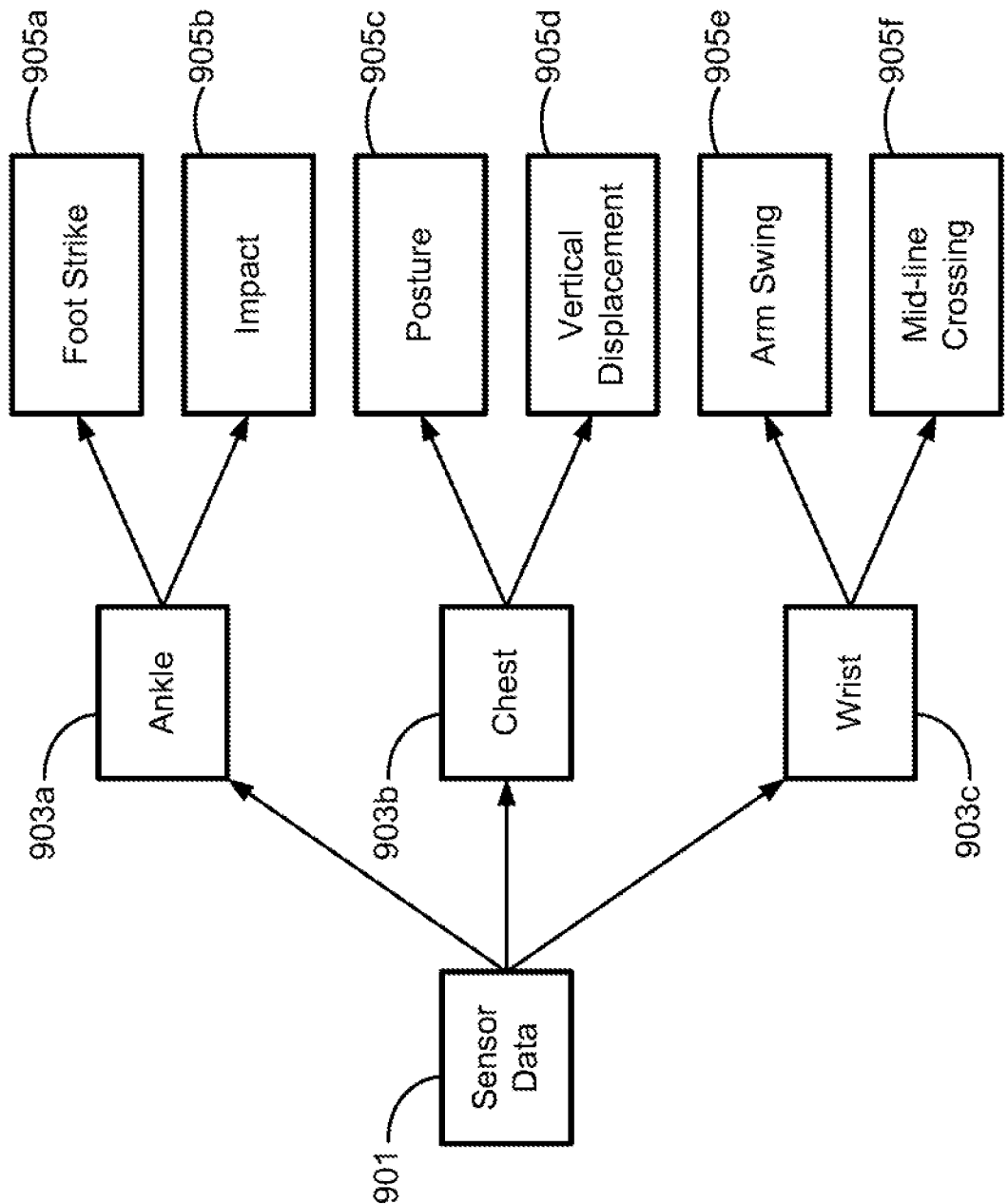
FIG. 9 illustrates a state diagram with respect to an on-body status and location of a wearable device in accord with aspects of the present disclosure.

FIG. 9 illustrates an overall process flow for determining location-specific metrics to activate on a wearable device 100 based on the determined location in accord with aspects of the present disclosure. Referring to block 901, sensor data in the form of 3-axis acceleration information from the accelerometer 105 of the wearable device 100, temperature information from the temperature sensor 111, or a combination thereof is generated and/or collected. Although not shown in FIG. 9, the wearable device 100 can initially process the acceleration information and/or the temperature information to determine its on-body status prior to determining location-specific metrics to activate.

From processing the acceleration information, the temperature information, or a combination thereof, one of three exemplary locations 903*a*-903*c* is determined as the location of the wearable device 100. The three exemplary locations 903*a*-903*c* include the ankle 903*a*, the chest 903*b*, and the wrist 903*c*. However, as discussed above, the determined location can be any location discussed herein, and is not limited to the three locations with respect to FIG. 9.

Based on the location of the wearable device 100 being one of the three exemplary locations 903*a*-903*c*, the wearable device 100 automatically configures itself according to one or more location-specific metrics 905*a*-905*f*. By way of example, such automatic configuring can include selecting computer program code, or one or more portions of computer program code, associated with predefined modes of operation and/or analysis with respect to the one or more location-specific metrics 905*a*-905*f*.

As illustrated in FIG. 9, exemplary metrics associated with the ankle 903*a* include a foot strike metric 905*a* and an impact metric 905*b*. According to the wearable device 100 automatically determining its location on the ankle 903*a*, computer program code associated with processing the acceleration information based on the foot strike metric 905*a* and the impact metric 905*b* is selected and executed by, for example, the processor 101 to automatically configure or reconfigure functionality of the wearable device 100 based on the location.

Exemplary metrics associated with the chest 903*b* include a posture metric 905*c* and a vertical displacement metric 905*d*. Thus, according to the wearable device 100 automatically determining its location on the chest 903*b*, computer program code associated with processing the acceleration information based on the posture metric 905*c* and the vertical displacement metric 905*d* is selected and executed by, for example, the processor 101 to automatically configure or reconfigure functionality of the wearable device 100 based on the location.

Exemplary metrics for the wrist 903*c* include an arm swing metric 905*e* and a mid-line crossing metric 905*f*. Thus, according to the wearable device 100 automatically determining its location on the chest 903*c*, computer program code associated with processing the acceleration information based on the swing metric 905*e* and the mid-line crossing metric 905*f* is selected and executed by, for example, the processor 101 to automatically configure or reconfigure functionality of the wearable device 100 based on the location. Accordingly, FIG. 9 illustrates an exemplary general flow for a wearable device 100 automatically configuring (or reconfiguring) itself with respect to location-specific metrics based on determining its location on a user.

Although not illustrated with respect to FIG. 9, in addition to the wearable device 100 automatically configuring itself according to the one or more location-specific metrics 905*a*-905*f*, configuring the wearable device 100 based on the determined location can further include enabling one or more other sensing modalities of the wearable device 100. By way of example, and as discussed above, the wearable device 100 can include one or more additional components for performing one or more additional sensor modalities, such as, but not limited to, heart rate measurements, electrical signal measurements (e.g., EKG, EMG, ECG), hydration level measurements, neural activity measurements, conductance measurements, and/or pressure measurements. The modes of these additional components may apply to only certain locations of the wearable device 100 on the user. For example, an EKG component may apply to the location of the user's chest and not the user's ankle or foot.

In accordance with some embodiments of the invention, the wearable device 100 can enable and/or disable one or more of these additional components based on the determined location of the wearable device 100 on the user. The additional components can be pre-defined as being associated with certain locations on the user. Upon the wearable device 100 determining its specific location, the wearable device 100 can activate the additional components associated with the specific location. Moreover, the wearable device 100 can deactivate and/or not activate other of the additional components that are not pre-defined as being associated with the specific location. Such deactivation and/or non-enablement can conserve resources of the wearable device 100, such as battery life.

The additional components that are enabled based on the determined location of the wearable device 100 may generate additional physiological and/or biometric information. In accordance with some embodiments of the invention, the wearable device 100 can automatically configure itself according to one or more location-specific metrics that analyze the additional physiological and/or biometric information. Such automatic configuring may include selecting computer program code, or one or more portions of computer program code, associated with predefined modes of operation and/or analysis with respect to additional physiological and/or biometric information and metrics specific to processing this additional information. By way of example, if an EMG component is enabled for measuring muscle activity of the user's arm, computer program code associated with a location-specific metric for analyzing the muscle activity specific to the location of the arm may also be selected and executed by the processor 101 based on the wearable device 100 determining its location on the arm. By way of another example, if an ECG component is enabled for measuring heart activity when the wearable device 100 is detected as being positioned on a user's chest, computer program code associated with a location-specific metric for analyzing the heart activity can also be selected and executed by the processor 101 based on the wearable device 100 determining its location on the chest. Accordingly, according to the automatic determination of location, the wearable device 100 can change its operating mode, such as by enabling and/or disabling additional components of the wearable device 100.

According to the present concepts disclosed above, the determination of the location of the wearable device 100 on the user with respect to processing acceleration information is substantially instantaneous and does not rely on historical information. That is, according to some embodiments, historical acceleration information is not needed for the wearable device 100 to determine its present location on a user. A single feature set is determined from the generated acceleration information and used to determine the location of the wearable device 100. As discussed above, such a feature set may be determined based on a set duration of generating the acceleration information, such as three seconds. From this acceleration information, a feature set is extracted and processed to determine the location of the wearable device 100 on a user. No historical information pertaining to before the three second duration is required for the wearable device 100 to determine its location on the user.

During normal use, the location of the wearable device 100 does not change. For example, a user may affix the wearable device 100 to their ankle, or don a sock that includes an integrated wearable device 100, and then perform an activity for several hours, such as running, walking, etc. During this time, the location of the wearable device 100 does not change. Yet, there is a possibility that erroneous information is generated, or an activity of a user briefly changes, such that the wearable device 100 may provide an erroneous determination of a location based on single feature set. While leveraging historical information is not necessary, such historical information may prevent the above-described erroneous determination of a location.

In accordance with one embodiment, historical information may be used to, for example, eliminate erroneous information from changing the determination of location by validating the determination. That is, historical acceleration information and/or historical feature sets may be used in conjunction with current acceleration information and/or a current feature set for validating the determination of the location. By way of example, the wearable device 100 may store the last L sets of features and/or the last M determinations of the location and use this information for determining or validating the current location of the wearable device 100. As non-limiting examples, L and M may be five such that the wearable device 100 uses the last five feature sets and/or determinations of the location in validating the current location of the wearable device 100 on the user. If the last L feature sets indicate that the wearable device 100 is on, for example, the ankle of the user, and the current feature set indicates that the wearable device 100 is on, for example, the chest, leveraging the last L feature sets may prevent the wearable device 100 from erroneously reconfiguring the functionality based on the chest location until a subsequent feature set indicates and/or validates that the location of the wearable device 100 is indeed now on the chest. Alternatively, an additional N feature sets and/or determinations may be used prior to reconfiguring the functionality of the wearable device 100, where N can be 2 or greater, such as L being equal to or greater than N. According to the foregoing, the wearable device 100 may use historical information to aid in validating the location of the wearable device 100 on the user.

According to some embodiments, the wearable device 100 can instead use the temperature information rather than the historical acceleration information to validate the determination of the location of the wearable device 100 based on the acceleration information. Accordingly, if, for example, the acceleration information leads to a different on-body status and/or location, the wearable device 100 can process the temperature information to validate the different on-body status, location and/or state, or a combination thereof.

According to some concepts of the present disclosure, a user can validate the determination of the location of the wearable device. Upon the wearable device 100 determining a location according to the above, the wearable device 100 can query the user to confirm the determined location. Such querying and validation can be used to decrease the likelihood of error and/or to improve the accuracy of the location detection technique by updating the technique, such as the decision tree, to improve the decision tree's performance. The wearable device 100 can query the user to confirm the location determination upon the initial determination or after a threshold number of determinations. Moreover, according to one embodiment, the wearable device 100 can use the historical information in combination with a validation by a user. By way of example, and without limitation, if a current determination of a location differs from historical information, the wearable device 100 can query the user to confirm whether the current determination of the location is correct.

The above-described query and confirmation can be performed according to one or more audio, visual, and/or tactile inputs and responses by the wearable device 100 and the user. Thus, one or more of the above-described additional components of the wearable device 100 can be a display, a speaker, a microphone, etc. that allows the wearable device 100 to query the user and receive a response from the user regarding a determined location of the wearable device 100.

According to some concepts of the present disclosure, the determination of the location of the wearable device 100 may occur continuously, periodically, and/or on demand. More specifically, any one or more steps associated with determining the location of the wearable device 100, such as generating the acceleration information, extracting the feature set(s), processing the feature set(s), generating temperature information and processing the temperature information, or a combination thereof to determine the location may occur continuously, periodically, and/or on demand.

Again, considering that, during normal use, the location of the wearable device 100 does not change, the wearable device 100 could alternatively, or in addition, use historical information to affect the timing of determining the location, such as stopping the generation of acceleration information, stopping the processing of the acceleration information, stopping the measuring of temperature information, stopping the processing of temperature information, or a combination thereof, to conserve power.

In accordance with an embodiment, a wearable device 100 may determine its location on a user during a set period of time and/or for a set number of feature sets. Upon reaching the end of the period of time or the set number of feature sets, the wearable device 100 may deactivate the accelerometer 105 and/or stop processing the acceleration information to conserve power. In one embodiment, the period of time and/or number of feature sets may be at the beginning of using the wearable device 100, or may be after a set time of using the wearable device 100.

In accordance with an embodiment, the set period of time or the set number of feature sets may continue during consecutive determinations of the same location. Upon a determination of a different location than previous locations determined during the set period of time and/or set number of feature sets, the set period of time and/or the set number of feature sets may reset to prevent the wearable device 100 from erroneously configuring the functionality prior to turning off the location determination functionality. According to the foregoing, the wearable device 100 may use historical information to reduce and/or conserve power with respect to determining the location on the user.

One application of determining the location of the wearable device 100 is to configure the wearable device 100 to generate, output, and/or process location-specific information. More specifically, upon determining the location of the wearable device 100 on the user, the wearable device 100 can activate one or more algorithms and/or one or more components to process and/or generate additional physiological and/or biometric information of the user that is specific to the determined location. Thus, the wearable device 100 is able to modify its functionality and/or operation based on the determined location.

With the accelerometer 105 already generating the acceleration information, the wearable device 100 can activate one or more algorithms to process the acceleration information according to one or more location-specific metrics to determine physiological information specific to the location. With the temperature sensor 111 already generating temperature information, the wearable device 100 can activate one or more algorithms to process the temperature information according to one or more location-specific metrics to determine physiological information specific to the location. Further, as discussed above, according to present concepts of the disclosure, the wearable device 100 may include additional components related to heart rate measurements, electrical activity measurements, hydration level measurements, neural activity measurements, conductance measurements, and/or pressure measurements. These additional components may generate additional physiological and/or biometric information regarding the user. This additional physiological and/or biometric information may also be processed by location-specific metrics.

By way of example, upon determining that a wearable device 100 is located on a user's chest, the wearable device 100 may activate one or more components and/or process information to determine physiological information regarding the user's posture, trunk rotation, and vertical displacement. By way of another example, upon determining that a wearable device 100 is located on a user's abdomen, the wearable device 100 may activate one or more components and/or process information to determine physiological information regarding the user's posture and vertical displacement and not trunk rotation. By way of another example, upon determining that a wearable device 100 is located on a user's upper leg or lower leg, the wearable device 100 may activate one or more components and/or process information to determine physiological information regarding heel/toe strike and foot contact. Specific to the lower leg, such as the wearable device 100 being on the user's ankle, the physiological information may further include heel lift/kickback and foot ground clearance. Specific to the upper leg, the physiological information may further include hip extension. By way of another example, upon determining that a wearable device 100 is located on a user's arm, the wearable device 100 may activate one or more components and/or process information to determine physiological information regarding arm swing, midline crossing, and elbow angle. This information may be used to analyze, for example, the efficiency and/or fatigue of the user.

Although described above, the foregoing provides non-limiting examples of the functionality of the wearable device 100 upon determining its location. Additional functionality may be implemented without departing from the spirit and scope of the present disclosure, such as, for example, activating an ECG component and a temperature sensor upon determining the wearable device 100 is located on a user's chest to monitor heart activity and temperature, respectively.

Figure 10A:
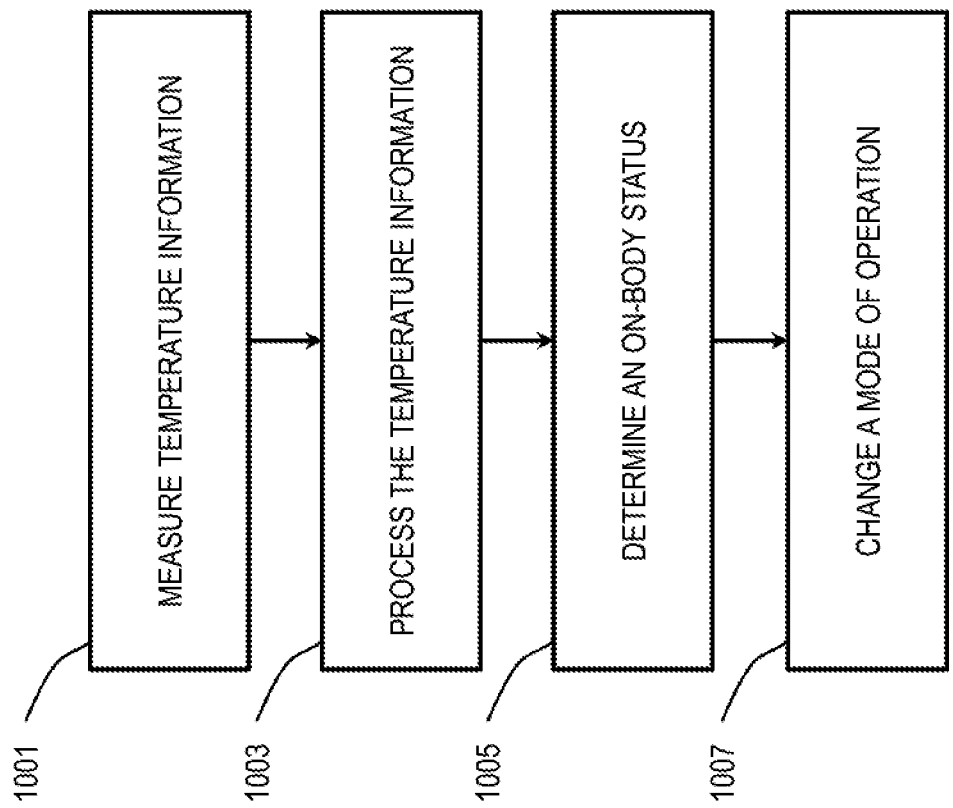
FIG. 10A is a flowchart illustrating a process for determining an on-body status of the wearable device in accord with aspects of the present disclosure.

FIG. 10A is a flowchart illustrating a process 1000 for determining an on-body status of the wearable device in accord with aspects of the present disclosure. In accordance with one embodiment, the processor 101 in conjunction with the memory storage module 103 and computer program code stored thereon, in addition to one or more components within the wearable device 100, such as the accelerometer 105 and/or the temperature sensor 111, may perform the process 1000 illustrated in FIG. 10A.

At step 1001, the wearable device 100 measures temperature information from a temperature sensor within the wearable device 100. As discussed above, the temperature sensor may be a temperature sensor embedded within a component of the wearable device 100, such as the temperature sensor 111 embedded within the accelerometer 105. Alternatively, the temperature sensor may be a separate and discrete component of the wearable device 100, such as the temperature sensor 113.

The temperature sensor measures the temperature associated with the wearable device 100 that is based on, for example, the ambient air temperature surrounding the wearable device 100, the skin temperature when the wearable device 100 is coupled to the skin of a user, or a combination thereof.

At step 1003, upon measuring the temperature information, the wearable device 100 processes the temperature information to determine a temperature, a change in temperature, a rate of change in temperature, or a combination thereof. The temperature, change in temperature, and/or the rate of change in temperature may be scaled or un-scaled.

At step 1005, the wearable device 100 determines its on-body status based, at least in part, on the temperature, the change in temperature, the rate of change in temperature, or a combination thereof. As discussed above, a single temperature may be used to indicate that the wearable device 100 is coupled to the skin on the user. Such a temperature can be above a threshold temperature, which indicates that the wearable device 100 is coupled to the user. Alternatively, the change in temperature may be used to indicate that the wearable device is coupled to the skin of the user. The change in temperature can be based on an initial temperature (e.g., ambient air temperature) and a present temperature (e.g., temperature affected by the skin of the user), which is used to indicate that the wearable device 100 is coupled to the body of a user. The rate of change in temperature can be based on an initial temperature (e.g., ambient air temperature), a present temperature (e.g., temperature affected by the skin of the user), and a period of time between the initial and present temperatures, which is used to indicate that the wearable device 100 is coupled to the body of a user and that the change in temperature is based on coupling the wearable device 100 to the user, rather than, for example, a change in ambient air temperatures.

According to some embodiments, the process 1000 can be performed with only temperature information. However, according to some embodiments, the wearable device 100 can use acceleration information in addition to the temperature information for determining the on-body status of the wearable device 100 according to the approaches described above (e.g., FIG. 8). Thus, as described above, the wearable device 100 can determine the on-body status based on acceleration information and temperature information to distinguish between, for example, the wearable device 100 being at rest in sunlight versus coupled to the user, although at the same temperature.

According to the above steps within the process 1000 of FIG. 10A, the wearable device 100 can determine whether it is coupled to the skin of a user and alter its functionality accordingly. Accordingly, according to the determined on-body status, the process 1000 can optionally include step 1007.

At step 1007, the wearable device 100 changes its mode of operation based, at least in part, on the on-body status. If, for example, the on-body status indicates that the wearable device 100 is in an off-body state, the wearable device 100 can turn off or change to a sleep mode to conserve battery life, if the wearable device 100 is not already in such a mode. Alternatively, if the on-body status indicates that the wearable device 100 is in an on-body state, the wearable device 100 can turn on, wake-up from a sleep mode, activate additional components, change to a specific mode (e.g., a cardiovascular mode, an exercise mode, etc.), if the wearable device 100 is not already in such a mode. Based on the process 1000 of FIG. 10A, a user can apply or remove the wearable device 100 and the mode of operation of the wearable device 100 can automatically update accordingly without requiring user intervention.

Figure 10B:
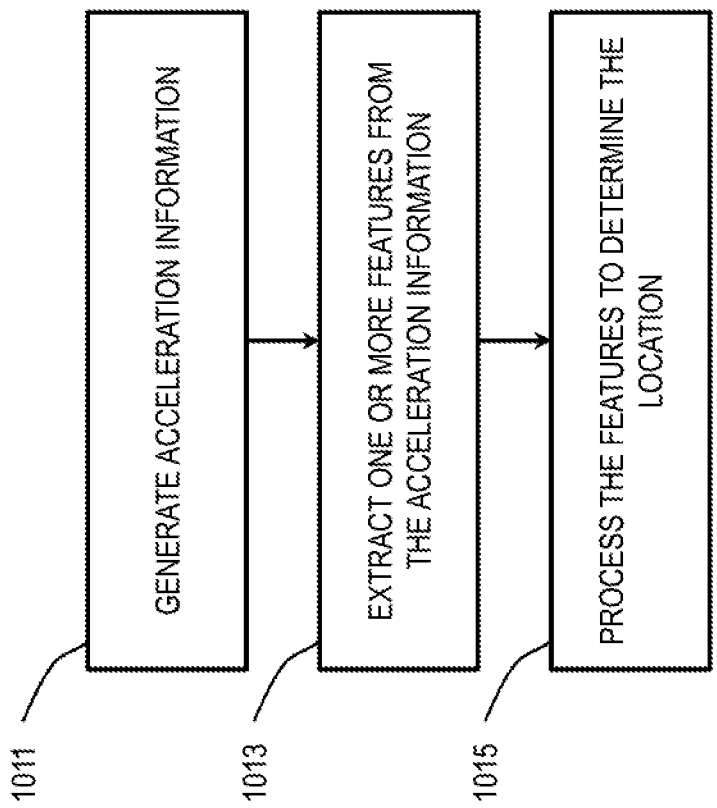
FIG. 10B is a flowchart illustrating a process for determining a location of a wearable device on a user based on acceleration information in accord with aspects of the present disclosure.

FIG. 10B is a flowchart illustrating a process 1010 for determining a location of a wearable device 100 on a user in accord with aspects of the present disclosure. In accordance with one embodiment, the processor 101 in conjunction with the memory storage module 103 and computer program code stored thereon, in addition to one or more components within the wearable device 100, such as the accelerometer 105, may perform the process 1010 illustrated in FIG. 10B.

At step 1011, acceleration information is generated based on acceleration experienced by (e.g., sensors connected to) the wearable device 100. The acceleration information can be generated by the accelerometer 105, and can be generated continuously, periodically, and/or on demand. As discussed above, the acceleration information can, for example, be along the x-axis, the y-axis, and the z-axis.

At step 1013, the acceleration information is processed to extract features from the acceleration information. The features characterize the acceleration information and may be extracted with respect to time and frequency domains. The features may comprise one or more of a dominant frequency, a frequency range, an acceleration scale, an acceleration range, an energy, and an entropy of the acceleration information. Further, the features may be extracted within feature sets that characterize the acceleration information with respect to a set period.

The processing of step 1013 can optionally include pre-processing the acceleration information, such as passing the acceleration information through one or more filters to prepare the acceleration information for feature extraction. Processing the acceleration information at step 1013 to determine the features may occur continuously, periodically, and/or on demand.

At step 1015, the features are processed to determine the location of the wearable device 100 on the user. The features may be processed based on a decision tree analysis to determine the location of the wearable device 100, or according to other classification techniques discussed above. The features may be processed to determine the location of the wearable device 100 on the user continuously, periodically, and/or on demand. According to the process 1000, a wearable device 100 may determine its location on a user automatically, and without input from the user or another user.

According to some embodiments, and as discussed above, the determination of the location of the wearable device 100 can also be based on processing the temperature information, in combination with or independent from processing the acceleration information. By way of example, the beginning of the decision tree, or one or more nodes of the decision tree, can be based on the temperature information. Alternatively, the temperature information can be processed to determine the location of the wearable device 100, independent from processing the acceleration information. As discussed above, temperature, changes in temperature, and/or a rate of change in temperature can be correlated to specific locations of wearable device 100 on the user. Such locations can be determined independent from the acceleration information or in combination with the acceleration information (e.g., to verify the acceleration information).

Figure 10C:
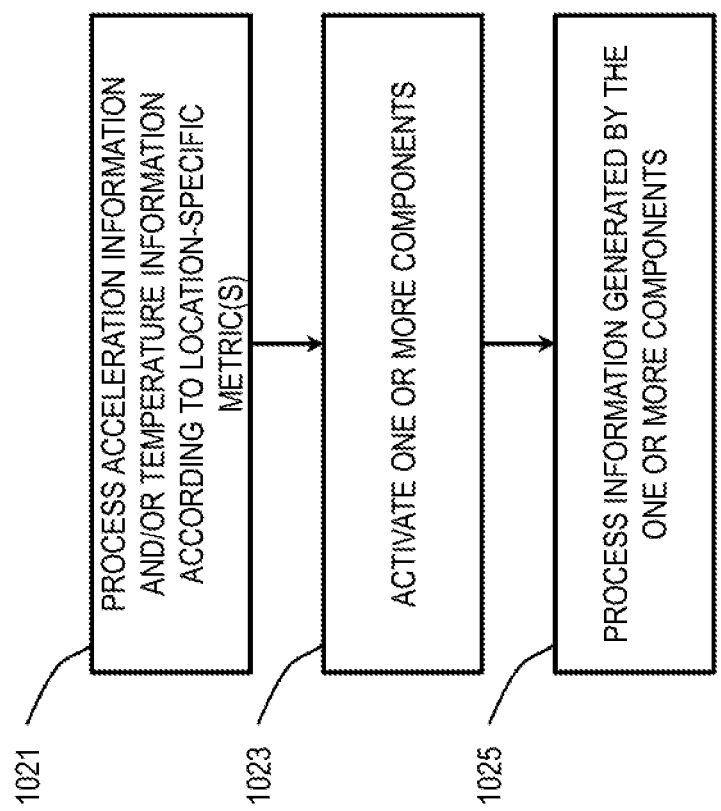
FIG. 10C is a flowchart illustrating a process for configuring functionality of a wearable device based on its location on a user in accord with aspects of the present disclosure.

FIG. 10C is a flowchart illustrating a process 1020 for configuring functionality of a wearable device 100 based on its location on a user in accord with aspects of the present disclosure. In accordance with one embodiment, the processor 101 in conjunction with the memory storage module 103 and computer program code stored thereon, in addition to one or more components within the wearable device 100 may perform the process 1020 illustrated in FIG. 10C. As discussed above, in accordance with some embodiments of the invention, the location information can be used to select a portion of the program code to execute on the wearable device 100, as well as activate additional sensing modalities. The location information can also be used to cause a remote device (e.g., a smart phone or computer) to execute a predefined program or application. Thus, in accordance with some embodiments of the invention, the wearable device 100 can configure an operating mode of the wearable device 100 or another device based on the automatic detection of the location of the wearable device 100.

At step 1021, in response to determining the location, the acceleration information and/or temperature information can be processed according to one or more location-specific metrics selected based on the location to generate location-specific information. By the wearable device 100 including the functionality of determining its location on a user, the wearable device 100 may automatically activate location-specific metrics and functionality to analyze the acceleration information and/or temperature information to generate information specific to the location. As discussed above, such specific information may pertain to posture, trunk rotation, vertical displacement, arm swing, midline crossing, elbow angle, heel/toe strike, foot contact time, hip extension, heel lift/kickback, contact time, and ground clearance of the foot. One or more of these specific types of information may not pertain to one location, which can be accounted for by the wearable device 100 by being able to determine its location on the user.

Optionally, at step 1023, in response to determining the location, the wearable device 100 may activate one or more additional components within the wearable device 100 based on the location. As discussed above, and by way of example, the wearable device 100 can activate an ECG component upon determining that the wearable device 100 is located on the chest. The wearable device 100 can alternatively, or in addition, activate a foot strike switch upon detecting that the wearable device 100 is on the foot or ankle. Thus, at step 1023, the wearable device 100 can configure the operating mode of one or more additional components of the wearable device 100 based on the determination of its location on a user.

In addition, the one or more additional components may be independent from the wearable device 100, such as one or more components in communication with the wearable device 100. By way of example, the wearable device 100 may be configured to communicate with a remote device, such as the user's smartphone or an implantable device. Upon determining its location on a user, the wearable device 100 can cause the smartphone or an implantable device to change its operating mode according to the location of, and data collected from, the wearable device 100.

By way of example, upon determining that the wearable device 100 is located on a user's chest, the wearable device 100 may communicate with the remote device to cause the remote device (e.g., an external smart phone device or an implantable device) to execute an application associated with working out, such as for lifting weights or for general exercise. Upon determining that the wearable device 100 is located on a user's leg, the wearable device 100 can communicate with the remote device to cause the remote device to reconfigure itself based on an aerobic exercise mode or a cardiovascular mode. Upon determining that the wearable device 100 is located on a user's arm, the wearable device 100 can communicate with the remote device to cause the remote device to reconfigure itself based on a throwing application, swimming application, and/or a weight lifting mode.

In accordance with some embodiments, the remote device may be an external storage device. According to the wearable device 100 determining its location on a user, such as on the chest, the wearable device 100 may activate one or more components of the wearable device 100 and log information generated by the components within the external storage device. The information can then be removed from the external storage device for later processing and/or analysis of the information, such as by another user (e.g., doctor, clinician, physician, etc.).

At step 1025, the wearable device 100 may process information generated by the activated component according to one or more location-specific metrics selected based on the location to generate location-specific information. According to the process 1020, the wearable device 100 may use its ability to determine its location on the user to gain location-specific information with respect to the location that a generic wearable device 100 would otherwise be incapable of generating, while maintaining the robustness of not relying on a user to correctly configure the wearable device 100 based on the location.

Figure 10D:
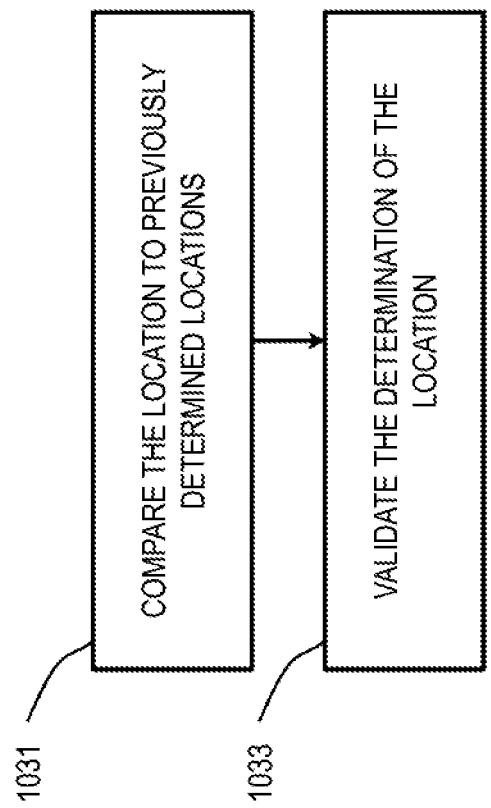
FIG. 10D is a flowchart illustrating a process for validating the determination of the location of the wearable device in accord with aspects of the present disclosure.

FIG. 10D is a flowchart illustrating a process 1030 for validating the determination of the location of the wearable device 100 in accord with aspects of the present disclosure. In accordance with one embodiment, the processor 101 in conjunction with the memory storage module 103 and computer program code stored thereon, in addition to one or more components within the wearable device 100, such as the accelerometer 105, may perform the process 1030 illustrated in FIG. 10D.

At step 1031, the determined location is compared to one or more previously determined locations of the wearable device 100 on the user. The wearable device 100 can store historical information with respect to a set number of determined locations, features, and/or acceleration information in a memory storage module 103 and use this information to determine location. By way of example, the wearable device 100 may store the last five location determinations.

At step 1033, the wearable device 100 validates the determination of the location based on the comparison. The validation may occur by determining whether the presently determined location matches the previously determined locations. If there is a match, the wearable device 100 may validate the present determination of the location. If there is no match, the wearable device 100 may activate an audio, visual, and/or tactile alarm indicating, for example, a fault. Alternatively, if there is a difference between the present location and the previously determined locations, the wearable device 100 may change the functionality without validating the determination of the comparison. In addition, or in the alternative, the validation can occur according to the wearable device 100 querying the user to confirm the determined location. Such a validation with respect to the user may optionally include leveraging the historical information prior to, in combination with, or subsequent to querying the user.

As discussed above, in combination with, or separate from, detection of the on-body status and/or location of the wearable device 100, and configuring the functionality and/or operation of a wearable device 100 based on the on-body status and/or location, according to some embodiments, the functionality and/or operation of a wearable device 100 can be configured based on the wearable device 100 determining its orientation. For certain sensing functionality, despite the location of the wearable device 100 being known (or unknown), the wearable device 100's orientation may be critical for its functionality and/or operation (e.g., to provide accurate sensor information). Alternatively, the location of the wearable device 100 on the body may be less critical than the orientation of the wearable device 100.

Detection of electrical signals related to the heart is one example where the knowing the orientation of the wearable device 100 relative to the body (e.g., relative to the heart) is important for proper functionality and operation of the wearable device 100, such as for proper functionality and operation with respect to analyzing and processing the detected heart beat signals (e.g., ECG signals).

Detecting heart beat signals is predominantly based on placing electrodes or contacts across specific areas of the chest, also known as leads or lead lines. FIGS. 11A-11C show diagrams of three leads within the electrocardiography system. Specifically, each of FIGS. 11A-11C show a lead, also known as a limb lead, within Einthoven's triangle, which is an imaginary formation of three limb leads in a triangle used in electrocardiography.

FIG. 11A shows the arrangement of the first limb lead (e.g., Lead I) within Einthoven's triangle relative to the body of a user (e.g., a human). Lead I is defined as the axis that extends between the shoulders of the body. Lead I is generally within or parallel to the coronal plane of the body (e.g., horizontal) and perpendicular to the sagittal plane of the body. Electrical signals associated with Lead I are generally measured or detected by placing a negative electrode (represented by the minus (−) symbol) on the right shoulder and placing a positive electrode (represented by the plus (+) symbol) on the left shoulder. However, placement of the negative and positive electrodes at the shoulders merely represents the preferred locations of the electrodes. The electrodes can be placed at other locations, such as other locations on the torso, while still being able to detect the electrical signals associated with Lead I of the Einthoven triangle. The important aspect is that the electrodes are positioned to define an axis that is generally parallel to the coronal plane of the body and perpendicular to the sagittal plane of the body.

FIG. 11B shows the arrangement of the second limb lead (e.g., Lead II) within Einthoven's triangle relative to the body. Lead II is defined as the axis that extends from the right should to the left leg. Lead II is about 60° off (e.g., below) of being parallel to the coronal plane of the body and about −30° off (e.g., to the left) of being parallel to the sagittal plane of the body. Electrical signals associated with Lead II are generally measured or detected by placing a negative electrode (represented by the minus (−) symbol) on the right shoulder and placing a positive electrode (represented by the plus (+) symbol) on the left leg. However, placement of the negative and positive electrodes at the right shoulder and the left leg merely represents the preferred locations of the electrodes. The electrodes can be placed at other locations, such as other locations on the torso, while still being able to detect the electrical signals associated with Lead II of the Einthoven triangle. The important aspect is that the electrodes are positioned to define an axis that is about 60° below parallel to the coronal plane of the body and about −30° off (e.g., to the left) of being parallel to the sagittal plane of the body.

FIG. 11C shows the arrangement of the third limb lead (e.g., Lead III) within Einthoven's triangle relative to the body. Lead III is defined as the axis that extends from the left shoulder to the left leg. Lead III is about 120° off (e.g., below) of being parallel to the coronal plane of the body and about 30° off (e.g., to the right) of being parallel to the sagittal plane of the body. However, because Lead III is defined based on the left shoulder, rather than the right shoulder of Lead II, Lead III is generally the mirror image of Lead II relative to the sagittal plane of the body. Electrical signals associated with Lead III are generally measured or determined by placing a negative electrode (represented by the minus (−) symbol) on the left shoulder and placing a positive electrode (represented by the plus (+) symbol) on the left leg. However, placement of the negative and positive electrodes at the left shoulder and the left leg merely represents the preferred locations of the electrodes. The electrodes can be placed at other locations, such as other locations on the torso, while still being able to detect the electrical signals associated with Lead III of the Einthoven triangle. The important aspect is that the electrodes are positioned to define an axis that is about 120° below parallel to the coronal plane of the body and about 30° off (e.g., to the right) of being parallel to the sagittal plane of the body.

With electrodes positioned according to Lead I, II, and III, the electrodes can detect characteristic waveforms associated with how the three-dimensional cardiac electrical vector propagates within the body as the heart beats. FIG. 12 shows a diagram of one period of an ECG signal or trace of a heartbeat, along with labels of the associated waves generated within the ECG signal. The first wave, the P-wave, represents depolarization of the atria of the heart. More specifically, the first half of the P-wave is the activation of the right atrium, and the second half of the P-wave is the activation of the atria septum and the left atrium. The duration of the P-wave can vary between about 0.08 and about 0.11 seconds in normal adults. The Q, R, and S-waves are generally grouped together as the QRS complex and refer to the ventricular repolarization of the heart. The T-wave represents the ventricular repolarization.

Clinical recording of the ECG waves or signals requires accurate placement of the electrodes on the body. Accurate placement consists primarily of placing the electrodes within the specific axes described above for the specific leads (e.g., Lead I, II, and III). Although the locations of the electrodes may impact the waveforms, the locations merely affect the amplitudes of the waveforms within each lead. Thus, while the preferred locations of the electrodes are shown in FIGS. 11A-11C, the electrodes can be placed on the chest.

Although it may be relatively easy for a cardiologist to correctly orient the electrodes and/or identify the orientations of the electrodes from sample ECG waveforms, an untrained user (e.g., consumer, a non-cardiologist, etc.) may have difficulty orienting the electrodes and/or identifying the electrode locations and/or orientations from the waveforms. Further, based on the potential variability of the resulting ECG waveforms, algorithms processing the ECG waveforms also may not be able to correctly identify the electrode locations and/or orientations based solely on the waveforms themselves. For example, the individual components of a standard ECG signal are affected independently by the lead type being recorded. In general, Lead I presents a positive P-wave, a negative Q-wave, a large positive R-wave, and a positive T-wave. The S-wave is generally missing for Lead I. Lead II presents a large positive P-wave, a large positive R-wave, a negative S-wave, and a positive T-wave. The Q-wave is generally missing for Lead II. Lead III presents large negative Q, R, and S-waves, a small P-wave, and a negative T-wave. Deviations from these patterns can represent incorrect electrode placement (e.g., orientation). Thus, purely using algorithms to determine the correct orientation is not possible. Further, deviations from these patterns can represent issues with the heartbeat of the user being examined. In this case, the deviations allow for a cardiologist to determine specific anatomical regions of the heart with abnormal electrophysiology. For example, an inverted or biphasic P-wave in Lead I may indicate issues with the atrial pacemaker of the heart. However, without knowing that the electrodes are placed correctly, an inverted or biphasic P-wave in Lead I may merely mean that the electrodes are placed incorrectly. Therefore, according to the concepts of the present disclosure, a wearable device (e.g., wearable device 100) can automatically determine its orientation, along with the orientation of one or more electrodes contained within the device, to automatically determine the orientation of the electrodes relative to generated ECG signals from the body.

As discussed above, the wearable device 100 discussed herein can contain electrical contacts 115 to detect the ECG waveforms generated by the body (e.g., heart). More specifically, the electrical contacts 115 can include a positive contact 115 and a negative contact 115 similar to positive and negative contacts of FIGS. 11A-11C, but contained within a single device. In some aspects, the electrical contacts 115 are either in contact with the skin of the user, or within a distance of the skin (e.g., within about 3 mm) but still able detect or sense the ECG signals. Further, the electrical contacts 115 are configured on the wearable device 100 to be a known distance apart and an a known arrangement with respect to each other.

According to the aspects of the present disclosure discussed above, the wearable devices 100 can detect its location on the body of the user. However, in the case of a heartbeat, as an example, the wearable device 100 must also know its orientation with respect to the body, such as with respect to the torso and its position relative to the Einthoven triangle (e.g., Lead I, II, or III). In accord with aspects of the present disclosure, in addition to the electrical contacts 115, the wearable device 100 also includes the accelerometer 105, discussed above. Using the accelerometer 105, and according to conventional techniques, such as those discussed in M. Pedley, Tilt Sensing Using a Three-Axis Accelerometer, Freescale Semiconductor Application Note, Document Number AN3461, Rev. 6, March 2013, the disclosure of which is hereby incorporated by reference herein in its entirety, the accelerometer 105 can detect the wearable device 100's orientation with respect to the body, particularly the orientation of the wearable device 100 relative to Lead I, II, or III. In some aspects, accelerometer information on, for example, posture, activity, and movements, discussed above, can provide further information on the position and orientation of the wearable device 100 on the torso. Further, the electrical contacts 115 of the wearable device 100 are configured in a known arrangement with respect to the accelerometer 105. By knowing the orientation of the accelerometer 105, and wearable device 100 in general, the wearable device 100 also knows the orientation of the electrical contacts 115. By knowing the orientation of the electrical contacts 115, the wearable device 100 can determine whether the electrical contacts 115 are arranged in the Lead I, II, or III orientation.

Figure 13:
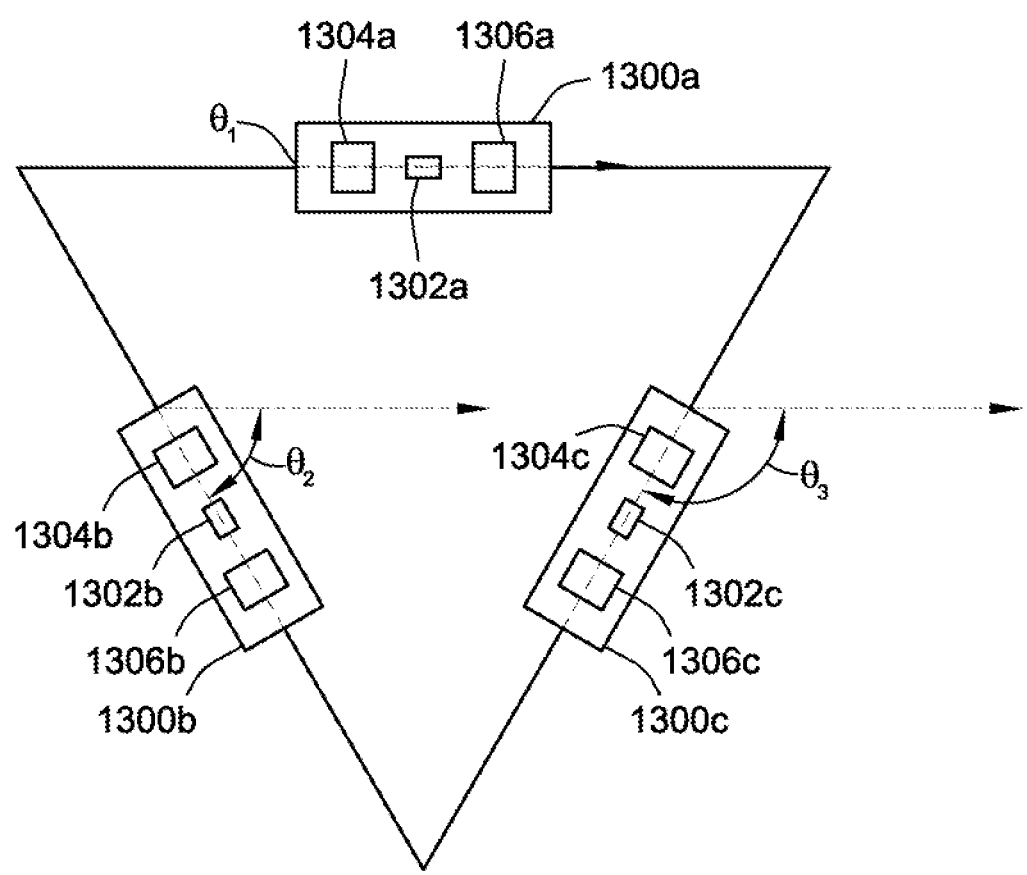
FIG. 13 shows a schematic view of wearable devices arranged for measuring electrocardiography signals in accord with aspects of the present disclosure.

FIG. 13 shows orientations of three wearable devices 1300a-1300c relative to axes of the Leads I, II, and III discussed above, in accord with aspects of the present disclosure. The wearable devices 1300a-1300c can be ECG wearable devices 100. However, in some aspects, the wearable devices 1300a-1300c may not include one or more components of the wearable device 100, such as the temperature sensor 113, depending on the overall functionality of the wearable devices 1300a-1300c.

To detect the electrical signals of the body, the wearable devices 1300a-1300c also include contacts (e.g., electrical contacts 115). Specifically, the wearable devices 1300a-1300c include negative contacts 1304a-1304c and positive contacts 1306a-1306c. The wearable devices 1300a-1300c are configured so that the positions of the accelerometers 1302a-1302c are known relative to the positions of the contacts (e.g., negative contacts 1304a-1304c and positive contacts 1306a-1306c). Based on the inclusion of the accelerometers 1302a-1302c, the wearable devices 1300a-1300c are able to determine their orientations relative to gravity and the heart of the user. Based on the orientations of the wearable devices 1300a-1300c relative to the heart, and the known orientations of the electrodes 1304a-1306c within the wearable devices 1300a-1300c, the wearable devices 1300a-1300c can determine what lead position (e.g., Lead I, II, or III) they are arranged in relative to the body.

More specifically, using the accelerometer information from the accelerometers 1302a-1302c, the wearable devices 1300a-1300c can determine their angle with respect to the axes of the body (e.g., coronal plane), otherwise referred to as their classification. Based on the angles of the wearable devices 1300a-1300c relative to the axes of the body, the wearable devices 1300a-1300c can determine what lead position they are in. For example, based on the position of wearable device 1300a being about parallel (e.g., $\theta_1=0°$) to the coronal plane of the body, the wearable device 1300a can determine that it is in the Lead I orientation. Based on the position of wearable device 1300b being about 60° below parallel (e.g., $\theta_2=60°$) being parallel to the coronal plane of the body, the wearable device 1300b can determine that it is in the Lead II orientation. Based on the position of wearable device 1300c being about 120° below parallel (e.g., $\theta_2=120°$) to the coronal plane of the body, the wearable device 1300c can determine that it is in the Lead III orientation.

In some aspects, the wearable devices 1300a-1300c can include a truth table, such as in the form of an algorithm, that is stored in, for example, memory (e.g., memory storage module 103) and processed by a processor (e.g., processor 101) for determining what position the wearable devices 1300a-1300c are in based on the determined information from the accelerometers 1302a-1302c. Specifically, the orientations of the accelerometers 1302a-1302c can be determined based on the coronal angle θ (e.g., $\theta_1$, $\theta_2$, $\theta_2$). If the coronal angle θ is determined to be about 0°, the orientation of the wearable device is determined as Lead I. If the coronal angle θ is determined to be about 60° relative to and below the coronal plane, the orientation of the wearable device is determined as Lead II. If the coronal angle θ is determined to be about 120° relative to and below the coronal plane, the orientation of the wearable device is determined as Lead III.

In some aspects, the orientations of the wearable devices 1300a-1300c based on the coronal angle θ can include a tolerance margin δ. The tolerance margin δ can accommodate for orientations of the wearable devices 1300a-1300c that are not exactly the angles discussed above but close enough (e.g., within the pre-defined tolerance margin δ) for accurate and processing sensing of the ECG waveforms by the wearable devices 1300a-1300c. In some aspects, the tolerance margin δ can be, for example, 1°, 2°, 5°, 10°, or 15°. In some aspects, the value of the tolerance margin δ can be set based on the experience level of the intended user of the wearable devices 1300a-1300c. For example, for wearable devices 1300a-1300c used in a medical setting and which may be used by a trained professional (e.g., clinician, technician, doctor, etc.), the tolerance margin δ may be lower, such as 3°. For wearable devices 1300a-1300c used by untrained users, such as laypeople, the tolerance margin δ may be higher to accommodate the greater difference from the preferred orientation based on the lack of skill of the user placing the wearable devices 1300a-1300c of the bodies. However, regardless of whether the wearable devices 1300a-1300c include tolerance margins δ with respect to determining the coronal angle θ, coronal angles θ that are determined to be outside of the values discussed above are classified as unknown or unreliable.

In some aspects, the wearable devices 1300a-1300c can include indicators (e.g., visual, audible, and/or tactile indicators) that indicate when orientations are unknown or unreliable to allow for a user to adjust the orientations. In some aspects, the indicators can provide indications for how the user should manipulate the position of the wearable devices 1300a-1300c to correct the orientation. For example, if a coronal angle is off by a known amount (e.g., 10°), the wearable devices 1300a-1300c can provide indicators that indicate the direction to move the wearable devices 1300a-1300c and the amount of movement. In some aspects, the wearable devices 1300a-1300c output an indication to a computer device in communication with the wearable devices 1300a-1300c indicating that the orientations are unknown or unreliable, and the computer device can include the indicators (e.g., visual, audible, tactile).

Figure 14:
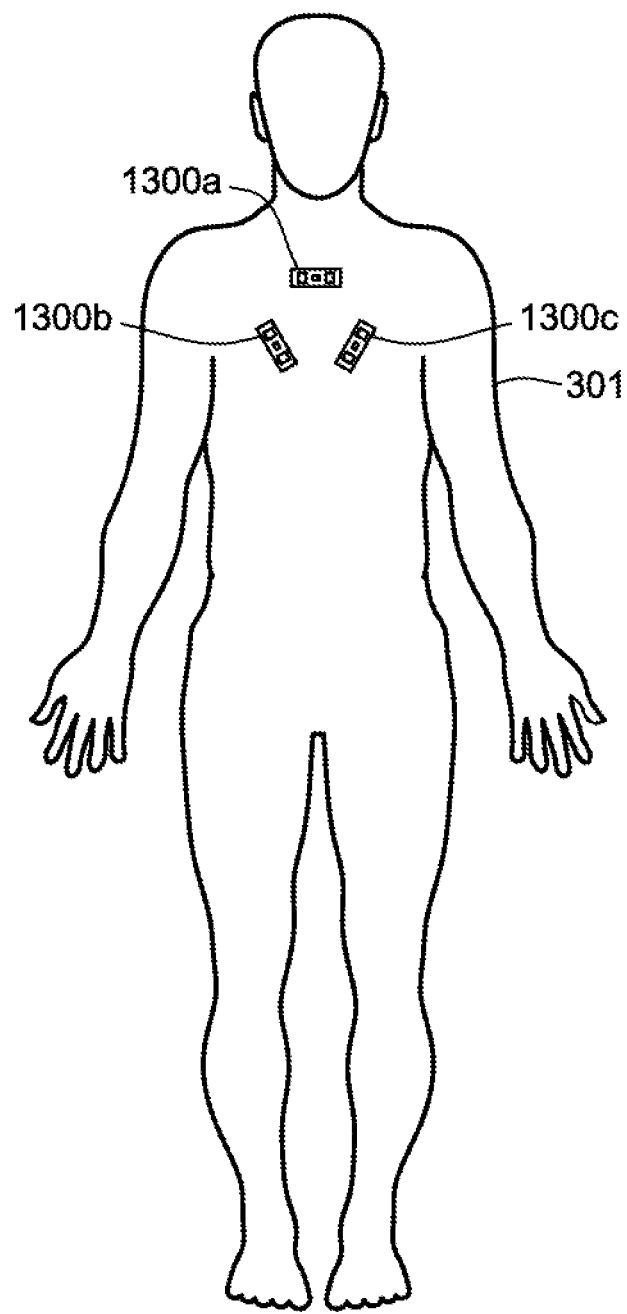
FIG. 14 shows the wearable devices of FIG. 13 arranged on the chest of a user for measuring electrocardiography signals in accord with aspects of the present disclosure.

Referring to FIG. 14, FIG. 14 shows the three ideal placements of the wearable devices 1300a-1300c relative to the body 301 of a user, such as a human user, in accord with aspects of the present concepts. As shown, wearable device 1300a is placed on the upper torso of the body 301 in the Lead I orientation. Wearable device 1300b is placed on the upper torso of the body 301, below wearable device 1300a, in the Lead II orientation. Wearable device 1300c is placed on the upper torso of the body 301, below wearable device 1300a and to the side of wearable device 1300b, in the Lead III orientation. With the wearable devices 1300a1-1300c arranged on the body 301 as shown, the wearable devices 1300a-1300c can detect the characteristic ECG waveforms of Leads I, II, and III, respectively. However, the specific positions and orientations of the wearable devices 1300a-1300c are merely for illustrative purposes, and the position and orientation of each specific wearable devices 1300a-1300c can vary as discussed above.

Figure 15:
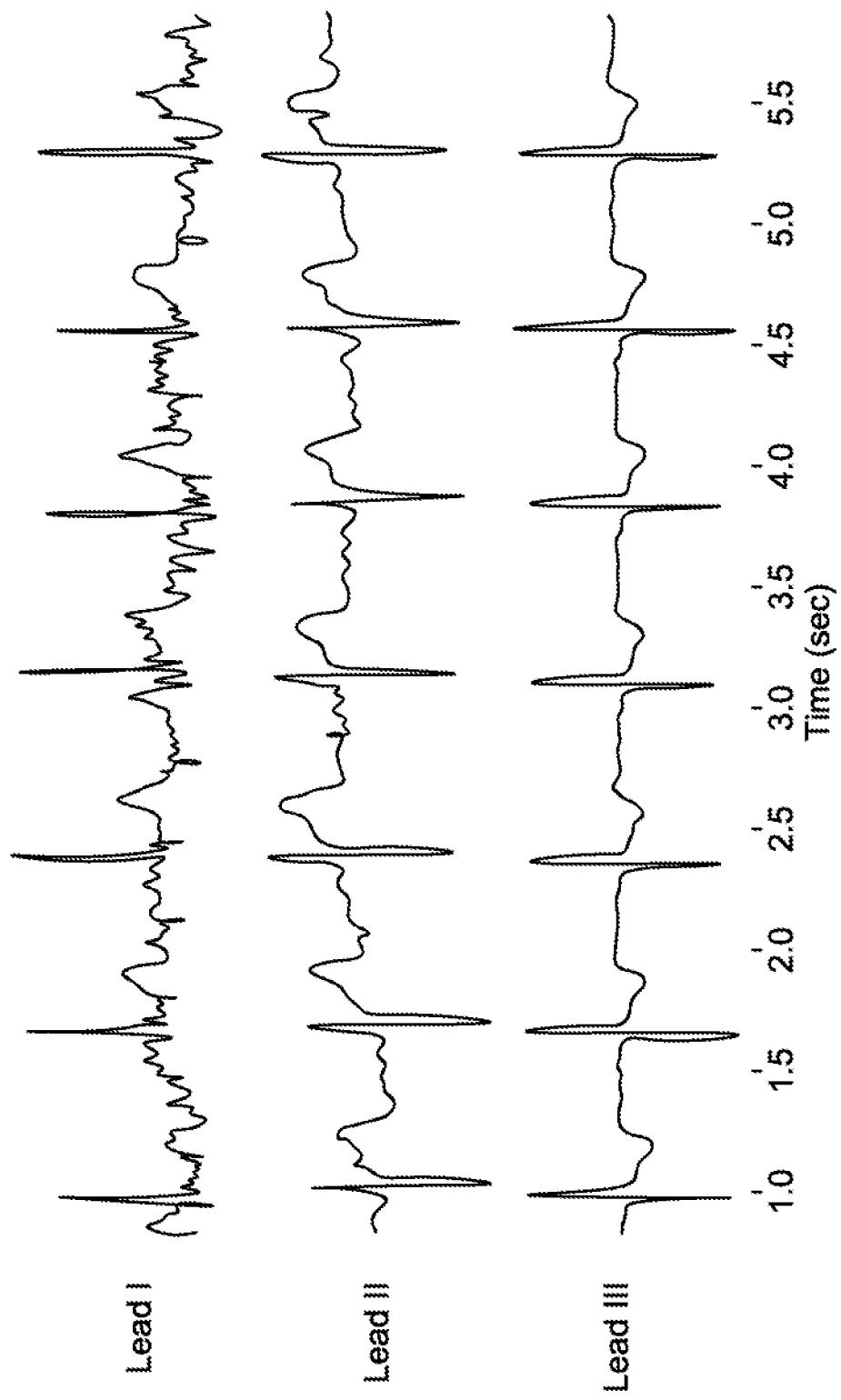
FIG. 15 shows example ECG signals measured by the wearable devices of FIG. 13 in accord with aspects of the present disclosure.

FIG. 15 shows example ECG waveforms collected from the wearable devices 1300a-1300c in the orientations and locations shown in FIG. 14, in accord with aspects of the present disclosure. For ease of illustration and explanation, the ECG waveforms for one or more certain leads (e.g., Lead I) have been scaled for comparing morphology of each lead. For example, without normalization, Lead I may have a small amplitude relative to Leads II and III, requiring amplification for visualization. In some aspects, ECG information generated by the contacts can be continuously, periodically, and/or on demand collected and/or processed by the wearable devices 1300a-1300c to extract features about the ECG waveforms, such as the P-wave, the QRS complex, and the T-wave. In some aspects, the ECG information is collected by the contacts continuously and/or periodically based on detected movement by the accelerometer 105.

Similar to configuring the functionality and/or operation of the wearable device 100 after determining the on-body status and/or location, after detecting the ECG waveforms shown in FIG. 15, the wearable devices 1300a-1300c can further process and/or analyze the ECG waveforms for various purposes. Initially, the wearable devices 1300a-1300c can characterize the waveforms to, for example, determine the elements of the waveforms (e.g., P-wave, Q-wave, R-wave, S-wave, QRS complex, T-wave, etc.) Characterization of the waveforms or determination of the waveform elements can be performed any number of ways, such as the ways disclosed in: J. Pan and W. J. Tompkins, A Real-Time QRS Detection Algorithm, IEEE Transactions on Biomedical Engineering, Vol. BME-32, No. 2, pp. 230-236 (1985); P. Laguna et al., Automatic Detection of Wave Boundaries in Multilead ECG Signals: Validation with the CSE Database, Computers and Biomedical Research, Vol. 27, No. 1, pp. 45-60 (1994); R. Jane et al., Evaluation of an Automatic Threshold Based Detector of Waveform Limits in Holter ECG with the QT Database, Computers in Cardiology, Vo. 24, pp. 295-298 (1997); and N. Boichat et al., *Wavelet-Based ECG Delineation on a Wearable Embedded Sensor Platform*, Sixth International Workshop on Wearable and Implantable Body Sensor Networks, BSN 2009, Berkeley, Calif., USA, Jun. 3-5 (2009), each of which are hereby incorporated herein by reference in its entirety. In addition, open source software is available from, for example, PhysioNet at http://www.physionet.org/physiotools/ecgpuwave/. In some aspects, the characterization and/or determination of the waveform elements can be determined based on the lead to which the wearable devices 1300a-1300c corresponds.

Upon characterizing the waveforms, the wearable devices 1300a-1300c can perform additional processing and/or analysis on the waveforms. The processing and/or analysis can be based on, at least in part, the classified lead type (e.g., Lead I, II, or III), the coronal angle θ, or a combination thereof. For example, the classified lead type and/or the coronal angle θ can be used as parameters within ECG-based algorithms. Expected ECG morphology and/or lead-derived heartbeat templates can also be used for ECG quality estimation. As a collective, the waveforms from the wearable devices 1300a-1300c can provide P/T-wave enhancements by using, for example, the Lead III waveform in conjunction with either the Lead I or Lead II waveform.

According to one embodiment, the wearable devices 1300a-1300c can be used to determine the electrical cardiac axis of the user upon which wearable devices 1300a-1300c are placed. The electrical cardiac axis is the general direction of the ventricular depolarization wave front in the plane of the Leads I, II, and III. The electrical cardiac axis can be an important clinical feature in diagnosing issues with the heart. For example, the likelihood of a user (e.g., a patient) having an abnormality typically increases as the electrical cardiac axis is beyond 90° or less than −30°. The electrical cardiac axis can be determined based on information from two of the wearable devices 1300a-1300c. As an example, the amplitude of the R-waves from two of the wearable devices 1300a-1300c, along with their orientation angles, can be used to determine the electrical cardiac axis. For Leads I and II, the calculation of the electrical cardiac axis is given by Equation 1:

$$R_{cardiac}(\phi, R_I, R_{II}) = \sqrt{R_I^2 + R_{II}^2 + R_I R_{II} \cos\phi} \qquad (1)$$

which can be written to solve for the electrical cardiac axis according to Equation 2:

$$\text{CARDIAC AXIS}(R_{cardiac}, R_I, \theta_I) = \arcsin\left(R_{cardiac} \frac{\sin\theta_I}{R_I}\right) \qquad (2)$$

where φ is the electrical cardiac axis, $R_I$ is the amplitude of the R-wave for Lead I, $R_{II}$ is the amplitude of the R-wave for Lead II, and $\theta_1$ is the coronal angle of Lead I. Based on these equations, the wearable devices 1300a-1300c can automatically calculate the electrical cardiac axis by a user placing the wearable devices 1300a-1300c on their body, and having the wearable devices detect their orientation and ECG signals. Thus, by use of accelerometer information form the accelerometers 1302a-1302c of the wearable devices 1300a-1300c for the calculation of the electrical cardiac axis, the wearable devices 1300a-1300c collectively can determine the inter-lead angle without requiring the assumption on the placement of the wearable devices 1300a-1300c or requiring the wearable devices 1300a-1300c orientated exactly for each wearable device.

In addition to, or in the alternative of, determining the electrical cardiac axis, upon determining their orientations and detecting the ECG waveforms, the wearable devices 1300a-1300c can configure heartbeat detection algorithms based on the specific lead (e.g., Lead I, II, or III). Because each waveform for each lead varies, specific algorithms can be used for each specific lead. Further, the wearable device 1300a-1300c can be in communication with each other, such as through the transceiver 107, or in communication with another device (e.g., computer device off-body, such as a smartphone, a tablet, a laptop, a computer, etc.) to perform additional analysis of the ECG signals. Such analysis includes, for example, combining the ECG waveforms from multiple wearable devices 1300a-1300c through spatial filtering to more accurately detect components of the ECG waveforms, such as the P, R, or T-waves. According to some embodiments, the wearable devices 1300a-1300c can include data (e.g., metadata) with the waveforms for automatic configuration of other devices, such as off-body computer devices that display and/or analyze the data for indicating what lead the ECG waveform applies to. For example, an off-body computer device can apply one or more filtering, amplifying, etc. processes on the waveforms based on the metadata with the waveform indicating to what lead the waveform applies. Such processes also include, for example, visually modifying the waveforms based on the detected lead. For example, Lead I can be amplified and filtered (e.g., with respect to noise) to visualizing on a display.

Based on the foregoing, wearable devices (e.g., wearable devices 1300a-1300c), after detecting their location, being informed of their location (e.g., by one or more inputs from the user), and/or based on assuming their location, can detect their orientations on the user to determine what lead of the ECG signals that the wearable devices detect applies to, and to perform additional processing and/or analysis on the ECG signals. Such analysis includes automatically calculating the electrical cardiac axis of a user, among other functionality. This provides for greater functionality and/or versatility by relying on a user to correctly orient the wearable devices.

In some embodiments, the aforementioned methods include at least those steps enumerated above. It is also within the scope and spirit of the present disclosure to omit steps, include additional steps, and/or modify the order of steps presented herein. It should be further noted that each of the foregoing methods can be representative of a single sequence of related steps; however, it is expected that each of these methods will be practiced in a systematic and repetitive manner.

The disclosure discussed herein can be applied to any wearable device 100 and/or system including the capability of determining 3-axis accelerometer information, which can enable a broad range of commercial applications. Such applications may include one that requires the user to place a sensor at different body locations to derive location-specific information. A wearable running coach, a wearable cross-fit monitor, and a wearable Parkinson's disease motor symptom monitor are but a few examples of such applications.

While particular embodiments and applications of the present disclosure have been illustrated and described, it is to be understood that the present disclosure is not limited to the precise construction and compositions disclosed herein and that various modifications, changes, and variations can be apparent from the foregoing descriptions without departing from the spirit and scope of the invention as defined in the appended claims.

What is claimed is:

1. An electronic device worn on a user, the electronic device comprising:
    one or more accelerometers configured to determine acceleration information during a first period;
    a processor;
    one or more associated memories, at least one of the associated memories including computer program code executable by the processor, the processor, configured by the computer program code, causes the electronic device to:
        extract features from the acceleration information, the features characterizing the acceleration information during the first period;
        determine a location of the wearable device on the user as one of a plurality of predefined locations based on the features; and
        configure functionality of the wearable device based on the location and one or more location-specific metrics associated with the one of the plurality of predefined locations.

2. The electronic device according to claim 1, wherein the plurality of predefined locations comprise a chest, an abdomen, an upper arm, a lower arm, a wrist, an upper leg, a lower leg, and an ankle of the user.

3. The electronic device according to claim 1, further comprising:
    one or more components configured to generate location-specification information,
    wherein the processor, configured by the computer program code, causes the electronic device to:
        selectively activate at least one of the one or more components based on the location.

4. The electronic device according to claim 1, wherein the processor, configured by the computer program code, causes the electronic device to:
    process the features based on a decision tree analysis to determine the location,
    wherein the decision tree analysis is generated based on previously determined acceleration information associated with the plurality of predefined locations.

5. A method of configuring a wearable device based on the wearable device determining its location on a user, the method comprising:
    determining acceleration information during a first period based on one or more accelerometers included within the wearable device;
    extracting features from the acceleration information, the features characterizing the acceleration information during the first period;
    determining the location of the wearable device on the user as one of a plurality of predefined locations based on the features; and
    configuring functionality of the wearable device based on the location and one or more location-specific metrics associated with the one of the plurality of predefined locations.

6. The method according to claim 5, wherein the plurality of predefined locations comprise a chest, an abdomen, an upper arm, a lower arm, a wrist, an upper leg, a lower leg, and an ankle of the user.

7. The method according to claim 5, further comprising:
    selectively activating at least one of one or more components within the wearable device configured to generate location-specification information based on the location.

8. The method according to claim 5, wherein the determining of the location comprises:
    processing the features based on a decision tree analysis to determine the location,
    wherein the decision tree analysis is generated based on previously determined acceleration information associated with the plurality of predefined locations.

9. An electronic device worn on a user, the electronic device comprising:
    one or more accelerometers and temperature sensors configured to generate acceleration information and temperature information based on acceleration and skin temperature experienced by the electronic device;
    a processor; and
    one or more associated memories, the one or more associated memories including computer program code executable by the processor, the processor, configured by the computer program code, causes the electronic device to:
        process the acceleration and skin temperature information to extract features from the acceleration information; and
        process the features to determine a location of the electronic device on the user.

10. The electronic device according to claim 9, wherein the features comprise one or more of a dominant frequency, a frequency range, an acceleration scale, an acceleration range, an energy, and an entropy of the acceleration information and skin temperature range with 0.01 C precision.

11. An electronic device wearable on a user comprising:
a temperature sensor configured to measure temperature information associated with the electronic device;
a processor; and
one or more associated memories, the one or more associated memories including computer program code executable by the processor, the processor, configured by the computer program code, causes the electronic device to:
process the temperature information to determine a temperature, a change in temperature, a rate of change in temperature, or a combination thereof;
determine an on-body status of the electronic device on the user based on the temperature, the change in temperature, the rate of the change in temperature, or a combination thereof; and
determine a location of the electronic device on the user based on the temperature, the change in temperature, the rate of change in temperature, or a combination thereof.

12. The electronic device according to claim 11, wherein the processor, configured by the computer program code, causes the electronic device to:
change a mode of operation based, at least in part, on the on-body status.

13. The electronic device according to claim 11, wherein the processor, configured by the computer program code, causes the electronic device to:
configure functionality of one or more components of the electronic device, one or more devices associated with the electronic device, or a combination thereof based, at least in part, on the location.

14. The electronic device according to claim 11, wherein the temperature sensor is a sub-component of a component of the electronic device.

15. The electronic device according to claim 14, wherein the component is a microelectromechanical system.

16. The electronic device according to claim 15, wherein the microelectromechanical system is a motion sensor.

17. The electronic device according to claim 11, wherein the temperature information is based, at least in part, on a skin temperature of the user when the electronic device is in an on-body state.

18. The electronic device according to claim 11, wherein the temperature information is based, at least in part, on ambient air temperature when the on-body status is an off-body state.

* * * * *